United States Patent
Steer et al.

(10) Patent No.: US 6,524,613 B1
(45) Date of Patent: Feb. 25, 2003

(54) HEPATOCELLULAR CHIMERAPLASTY

(75) Inventors: Clifford J. Steer, St. Paul, MN (US); Betsy T. Kren, Minneapolis, MN (US); Paramita Bandyopadhyay, Minneapolis, MN (US); Jayanta Roy-Chowdhury, New Rochelle, NY (US)

(73) Assignees: Regents of the University of Minnesota, Minneapolis, MN (US); Yeshiva University, Bronx, NY (US)

( * ) Notice: Subject to any disclaimer, the term of this patent is extended or adjusted under 35 U.S.C. 154(b) by 0 days.

(21) Appl. No.: 09/108,006

(22) Filed: Jun. 30, 1998

Related U.S. Application Data

(63) Continuation-in-part of application No. PCT/US98/08834, filed on Apr. 30, 1998.
(60) Provisional application No. 60/074,497, filed on Feb. 12, 1998, provisional application No. 60/064,996, filed on Nov. 10, 1997, provisional application No. 60/054,837, filed on Aug. 5, 1997, and provisional application No. 60/045,288, filed on Apr. 30, 1997.

(51) Int. Cl.[7] ................. A61K 9/127; A61K 31/711; A61K 31/7105; A61K 31/7125; A61K 31/712

(52) U.S. Cl. ................. 424/450; 514/44; 536/23.1; 536/24.1; 536/24.3

(58) Field of Search ................. 514/44; 536/23.1, 536/24.1, 24.3; 424/450

(56) References Cited

U.S. PATENT DOCUMENTS

| | | | |
|---|---|---|---|
| 5,166,320 A | 11/1992 | Wu et al. | 530/355 |
| 5,565,350 A | 10/1996 | Kmiec | 435/463 |
| 5,631,423 A | 5/1997 | Dzau et al. | 514/44 |
| 5,635,386 A | 6/1997 | Wu et al. | 435/458 |
| 5,683,866 A | 11/1997 | Sarkar et al. | 435/5 |
| 5,731,181 A | 3/1998 | Kmiec | 435/6 |
| 5,760,012 A | 6/1998 | Kmiec et al. | 514/44 |

FOREIGN PATENT DOCUMENTS

| | | |
|---|---|---|
| WO | WO 96/02655 | 7/1994 |
| WO | WO 93/04701 | 3/1998 |

OTHER PUBLICATIONS

Ye, Shanzhang et al., Targeted gene correction:a new strategy for molecular medicine, Molecular Medicine Today, p431–437, Oct., 1998.*
Crooke, S. T. Basic Principles of Antisense Therapeutics. Antisense Research and Application. Ed. Crooke. Springer–Verlag. pp. 1–50, 1998.*
Gura. Antisense has growing pains. Science 270 575–577, 1995.*
Abdallah, B., et al., "A Powerful Nonviral Vector for In Vivo Gene Transfer into the Adult Mammalian Brain: Polyethylenimine", 1996, Human Gene Therapy, 7, 1947–1954.
Aoki, M. et al., "Efficient In Vivo Gene Transfer into the Heart In the Rat Myocardial Infarction Model Using the HVJ (Hemagglutinating Virus of Japan)–Liposome Method", Journal of Molecular and Cellular Cardiology, 1997,29, 949–959.
Boletta, A., et al., "Nonviral Gene Delivery to the Rat Kidney with Polyethylenimine", Human Gene Therapy, 1997, 8, 1243–1251.
Boussif, O., et al., "A Versatile Vector for Gene and Oligonucleotide Transfer Into Cells in Culture and In Vivo: Polyethylenimine", Proceedings of the National Academy of the Sciences USA, 92, 1995, 7297–7301.
Cole–Strauss, A., et al., "Correction of the Mutation Responsible for Sickle Cell Anemia by an RNA–DNA Oligonucleotide", Science, 1996, 273, 1386–1389.
Dzau, V. J. et al., "Fusigenic Viral Liposome for Gene Therapy in Cardiovascular Diseases", Proceedings of the National Academy of the Sciences USA, 1996, 93, 11421–11425.
Fabrega, A. J., et al., "Cationic Lipid–Mediated Transfer of the hIL–10 Gene Prolongs Survival of Allogenic Hepatocytes in Nagase Analbuminemic Rats", 1996, Transplantation, 62, 1866–1871.
Ferrari, S., et al., "ExGen 500 is an Efficient Vector for Gene Delivery to Lung Epithelial Cells In Vitro and In Vivo", Gene Therapy, 1997, 4, 1100–1106.
Fraley, R., et al., "Liposome–Mediated Delivery of Deoxyribonucleic Acid to Cells: Enhanced Efficiency of Delivery Related to Lipid Composition and Incubation Conditions", 1981, Biochemistry, 20, 6978–6987.
Hara et al., "Receptor–Medicated Transfer of pSV2CAT DNA to Mouse Liver Cells Using Asialofetuin–Labeled Liposomes", 1995, Gene Therapy, 2, 784–788.
Hardman, D. A., et al., "Molecular and Metabolic Basis for the Metabolic Disorder Normotriglyceridemic Abetalipoproteinemia", 1991, Journal of Clinical Investigation, 88, 1722–1729.
Kaneda., et al., "Increased Expression of DNA Cointroduced with Nuclear Protein In Adult Rat Liver", 1989, Science, 243, 375–378.

(List continued on next page.)

Primary Examiner—David Guzo
(74) Attorney, Agent, or Firm—Pennie & Edmonds LLP

(57) ABSTRACT

The present invention concerns compositions and methods for the introduction of specific genetic changes in endogenous genes of the cells of an animal. The genetic changes are effected by oligonucleotides or oligonucleotide derivatives and analogs, which are generally less than about 100 nucleotides in length. The invention provides for macromolecular carriers, optionally incorporating ligands for clathrin coated pit receptors. In one embodiment the ligand is a lactose or galactose and the genetic changes are made in hepatocytes. By means of the invention up to 40% of the copies of a target gene have been changed in vitro. Repair of mutant genes having a Crigler-Najjar like phenotype and Hemophilia B phenotype were observed.

36 Claims, 6 Drawing Sheets

OTHER PUBLICATIONS

Kaneda Y., et al., "Introduction and Expression of the Human Insulin Gene in Adult Rat Liver", 1989, 264, 12126–12129.

Kircheis, R., et al., "Coupling of Cell–Binding Ligands to Polyethyleneimine for Targeted Gene Delivery", 1997, Gene Therapy, 4, 409–418.

Kren, B., et al., "Targeted Nucleotide Exchange in the Alkaline Phosphatase Gene of HuH–7 Cells Mediated by a Chimeric RNA/DNA Oligonucleotide", Jun. 1997, Hepatology, 25, 1462–1468.

Kren, B., et al., "In Vivo Site–Directed Mutagenesis of the Factor IX Gene by Chimeric RNA/DNA Oligonucleotides", Mar. 1998, Nature Medicine, 4, 285–290.

Letsinger, R. L., et al., "Control of Excimer Emission and Photochemistry of Stilbene Units by Oligonucleotide Hybridization", 1994, Journal of the American Chemical Society, 116, 811–812.

Letsinger, R. L.., et al., "Use of Stilbenedicarboxamide Bridge in Stabilizing, Monitoring, and Photochemically Altering Folded Conformation of Oligonucleotides", 1995, Juornal of the American Chemical Society, 117, 7323–7328.

Malloy et al., "Normotriglyceridemic Abetalipoproteinemia Absence of the B–100 Apolipoprotein", 1981, Journal of Clinical Investigation, 67, 1441–1450.

Nandi, P.K., et al., "Biologically Active Recombinant DNA in Clathrin–Coated Vesicles Isolated From Rat Livers After In Vivo Injection of Liposome–Encapsulated DNA", 1986, Journal of Biological Chemistry, 261, 16722–16726.

Ramani, K., et al., "Novel Gene Delivery to Liver Cells Using Engineered Virosomes", 1996, FEBS Letters, 404, 164–168.

Tang, M.K., and Szoka, F.C., "Influence of Polymer Structure on the Interactions of Cationic Polymers with DNA and Morphology of the Resulting Complexes", 1997 Gene Therapy, 4, 823–832.

Yoon, K., et al., "Targeted Gene Correction Episomal DNA in Mammalian Cells Mediated By A Chimeric RNA–DNA Oligonucleotide", Mar. 1996, Proceedings of the National Academy of the Sciences USA, 93, 2071–2076.

Zanta, et al., "In Vitro Delivery to Hepatocytes with Galactosylated Polyethyleneimine", 1997, Bioconjugate Chemistry, 8, 839–844.

Zhu, N., et al., "Systemic Gene Expression After Intravenous DNA Delivery Into Adult Mice", 1993, Science, 261, 209–211.

* cited by examiner 1    cctatccctgggggaggggggcgggacaggggggagccctataattggacaagtctggatccttgagtcctACTCAGCCCAG 83   CGGAGGTGAAGGACGTCCTTCCCCAGGAGCCGgtgagaagcgcagtcggggcacgggatgagctcagggcctctagaaa 165  gagctgggacccctgggaagccctggcctccagtagtctccaggagagctactcgggtcgggcttggggagaggaggagcgg 247  gggtgaggcaagcagcagggggactgacctggaagctgggaaggctgggcagcagagacgaccgacccgctagaagtgggggtggggg 329  agagcagctggactggatgtaagccatagcaggactccacgagttgtcactatcattatcgagcacctactggtgtcccc 411  agtgtcctcagatctccataactggggagccagggcagcgacacggtagcgtcgattggagaactttaaaatgagg 493  actgaattagctcataatgaacacgcgcttaactgtgaggttggagcttagaatgtgaaggagaatgaggaatgcgag 575  actgggactgagatggaaccggctggggagggggatggaatttgaaccccggagaggagaagatggaatttct 657  atggagccgacctgggatggggagataagagaagaccaggagggagttaaataggaatgggttgggggcggcttggtaa 739  atgtgctgggattaggctgttgcagataatgcaacaaggcttgaaggctaacctgggtgaggccggttggggcgctgg

FIG.2A

```
821   gggtggggaggagtcctcactgcggttgattgacagtttctccttcccagACTGGCCAATCACAGGCAGGAAGATGAAGGT
                                                                        M  K  V
903   TCTGTGGGCTGCGTTGCTGGTCACATTCTGGCAGgtatgggggcggggcttgctcgttccccgctcctcccctctca
       L  W  A  L  L  V  T  F  L  A
985   tcctcacctcaacctcctgccccattcagacagaccctgggccccctcttctgaggcttctgtgctgcttcctgctctga
1067  acagcgatttgacgctctctggcctcggtttccccatccttgagataggagttagaagttgttttgttgttgtttgt
1149  tgttgttgttgttttttttgagatgaagtctcgctctgtcgccaggctgagtgcagtggcgggatctcggctcactgca
1231  agctccgcctcccagttccacgccattctcctgcctcagctcccaagtagctgggactacaggcacatgccaccacccg
1313  actaacttttttgtattttcagtagagacggggttttcaccatgttggccaggctggtctgaactcctgacctcaggtgatc
1395  tgcccgtttcgatctcccaaagtgctgggattacaggcgtgagccaccgcacctggctgggagttagaggtttctaatgcat
1477  tgcaggcagatagtgaataccagacacggggcagctgtgatctttattctccatcaccccacacagccctgctgggcac
1559  acaaggacactcaatacatgtctttccgctggccggtggctcaccctgtaatcccagcactttggaggccaaggtggga
```

FIG. 2B

```
1641  ggatcacttgagcccaggagttcaacaccagcctgggcaacatagtgagacccctgtctctactaaaaatacaaaaattagcc 1723  aggcatggtgccacacacctgtgtctcagctactcaggaggctgaggcaggaggatcgcttgagcccagaaggtcaaggtt 1805  gcagtgaaccatgttcaggccgctgcactccagcctgggtgacagagcaagacccctgtttataaatacataatgctttccaa 1887  gtgattaaaccgactccccctcacccgtgccaccatgctccaagaagcatttgtggagcaccttctgtgtgccctagg 1969  tagctagatgcctgacggggtcagaaggacccctgacccgacttgttccacacagGATGCCAGGCCAAGGTGGAG
                                                             G  C  Q  A  K  V  E 2051  CAAGCGGTGGAGACAGAGCCGGAGCCCGAGCTGCGCCAGAGACCGAGTGGCAGAGCGGCCAGCGCTGGAACTGGCACTGG
      Q  A  V  E  T  E  P  P  E  L  R  Q  Q  T  E  W  Q  S  G  Q  R  W  E  L  A  L 2133  GTCGCTTTTGGGATTACCTGCTGGGTGCAGACACTGTCTGAGCAGGTGCAGGAGGAGCTGCTCAGTCCCAGTCACCA
      G  R  F  W  D  Y  L  R  W  V  Q  T  L  S  E  Q  V  Q  E  E  L  L  S  S  Q  V  T  Q 2215  GGAACTGAGgtgagtgtcccatcctggccctgacctcctggtgggcggctatacctcccaggtccaggtttcattctg
      E  L  R 2297  cccctgtcgctaagtcttggggggcctggtctctgctgttctagcttcctgcttcctcatttctgactcctgctttagctc 2379  tctggaattctctctctcagctttgtctctctcttcctgactcagtcctcacactgtctgctctgtctctgt
```

FIG.2C 2461 ccttcccctagctcttttatatagagacagagagatggggtctcactgtgttgccaggctggtcttgaacttctggctcaa 2543 gcgatcctcccgcctctggcctcccaaagtgctgggattagaggcatgagcaccttgcccggcctcctagctccttcttgtc 2625 tctgccctctgccctctgcatctgtctctgtcctcttctctgccttctgcctctgccgttcctctctccctc 2707 ttgggtctctctgctcatcccatctgcccgccccatcccagcccttctccccgctccccactgtgcgacacctccc 2789 gccctctcggccgcagGGCGCTGATGGACGAGACCATGAAGGAGTTGAAGGCCTACAAATCGGAGCTGGAAGAACAACTGAC
              A  L  M  D  E  T  M  K  E  L  K  A  Y  K  S  E  L  E  E  Q  L  T 2871 CCCGGTGGCGGAGGAGACGCGGGCACGGCTGTCCAAGGAGCTGCAGGCGGCAGCCCGGCTGGGCGCGGACATGGAGGAC
     P  V  A  E  E  T  R  A  R  L  S  K  E  L  Q  A  A  Q  A  R  L  G  A  D  M  E  D 2953 GTGTGCGGGCGGCTGGTGCAGTACCGCGGCGAGGTGCAGGCCATGCTCGGCCAGAGCACCGAGGAGCTGCGGGTGCGCCTG
     V  C  G  R  L  V  Q  Y  R  G  E  V  Q  A  M  L  G  Q  S  T  E  E  L  R  V  R  L 3035 CCTCCCACCTGCGCAAGCTGCGTAAGCGGCTCCTCCGCGATGCCGATGACCTGCAGAAGCGCCTGGCAGTGTACCAGGCCGG
     A  S  H  L  R  K  L  R  K  R  L  L  R  D  A  D  D  L  Q  K  R  L  A  V  Y  Q  A  G 3117 GGCCGCGAGGGCGCGAGCGCGGCCTCAGCGCGCCATCCGCGAGCGCCTGGGCCCCCTGGTTGAACAGGGCCGTGCGGGCC
     A  R  E  G  A  E  R  G  L  S  A  I  R  E  R  L  G  P  L  V  E  Q  G  R  V  R  A 3199 GCCACTGTGGGCTCCCTGGCCGGCCAGCCGCTACAGGAGGCGCAGGCCCAGGCCTGGGGCGAGCGGCTGCGCGCGGATGGAGG
     A  T  V  G  S  L  A  G  Q  P  L  Q  E  R  A  Q  A  W  G  E  R  L  R  A  R  M  E

FIG. 2D

3281 AGATGGGCAGCCGGACCCGGCGACCGCTGGACGAGCAGGTGAAGGAGCAGGTGGCGGAGGTGGCGGAGGTGCGCAAGCTGGAGGAGCAGGC
E   M   G   S   R   T   R   D   R   L   D   E   V   K   E   Q   V   A   E   V   R   A   K   L   E   E   Q   A

3363 CCAGCAGATACGCCTGCAGGCCGAGGCCTTCCAGGCCCGCCTCAAGAGCTGGTTCGAGCCCCTGGTTGAGGACATGCAGCGC
Q   Q   I   R   L   Q   A   E   A   F   Q   A   R   L   K   S   W   F   E   P   L   V   E   D   M   Q   R

3445 CAGTGGGCCGGGCTGGTGGAGAAGGTGCAGGCTGCCGTGGGGCACCCCTGTGCCAGGCGCGACAATCACTGAACGC
Q   W   A   G   L   V   E   K   V   Q   A   A   V   G   N   S   A   A   P   V   P   S   D   N   H

3527 CGAAGCCTGCAGCCATGCGACCCCACGCCACCCCGTGCTCCTGCCTCCGGCAGCTGCAGCGGGAGACCCTGTCCCGCC

3609 CCAGCCGTCCTCCTGGGGTGGACCCTAGTTTAATAAAGATTCACCAAGTTTCACGCatctgctggcctcccctgtgatttc 3691 ctctaagcccagctcagttttctcttttctgccacatactgccacacaattctcagccccctcctctctccatctgtgtctgt 3773 gtgtatctttctctgccctttttttttttt

FIG. 2E

HEPATOCELLULAR CHIMERAPLASTY

This application is a continuation-in-part of PCT/US 98/08834, filed Apr. 30, 1998, which claims benefit of the priority of U.S. patent application Ser. No. 60/045,288, filed Apr. 30, 1997, now abandoned, and application Ser. No. 60/054,837, filed Aug. 5, 1997, and application Ser. No. 60/064,996, filed Nov. 10, 1997, each of which are hereby incorporated by reference in their entirety. This application also claims benefit of the priority of application Ser. No. 60/074,497, filed Feb. 12, 1998.

1. FIELD OF THE INVENTION

The invention concerns methods and compositions for the use of recombinagenic oligonucleobases in vivo for the correction of disease causing genetic defects and the prevention of disease by introducing genetic modifications into the genes that encode Apolipoprotein B (Apo B) and Apolipoprotein E (Apo E)

2. BACKGROUND TO THE INVENTION

2.1 The Use of Chimeric Mutational Vectors to Effect Genetic Changes in Cultured Cells The inclusion of a publication or patent application in this specification is not an admission that the publication or the invention, if any, of the application occurred prior to the present invention or resulted from the conception of a person other than the present inventors.

The published examples of recombinagenic oligonucleobases are termed Chimeric Mutational Vectors (CMV) or chimeraplasts because they contain both 2'-O-modified ribonucleotides and deoxyribonucleotides.

An oligonucleotide having complementary deoxyribonucleotides and ribonucleotides and containing a sequence homologous to a fragment of the bacteriophage M13mp19, was described in Kmiec, E. B., et al., November 1994, Mol. and Cell. Biol. 14, 7163–7172. The oligonucleotide had a single contiguous segment of ribonucleotides. Kmiec et al. showed that the oligonucleotide was a substrate for the REC2 homologous pairing enzyme from Ustilago maydis.

Patent publication WO 95/15972, published Jun. 15, 1995, and counterpart U.S. Pat. No. 5,565,350 (the '350 patent) described duplex CMV for the introduction of genetic changes in eukaryotic cells. Examples in a Ustilago maydis gene and in the murine ras gene were reported. The latter example was designed to introduce a transforming mutation into the ras gene so that the successful mutation of the ras gene in NIH 3T3 cells would cause the growth in soft agar of a colony of cells ("transformation"). The '350 patent reported that the maximum rate of transformation of NIH 3T3 was less than 0.1%, i.e., about 100 transformants per $10^6$ cells exposed to the ras duplex CMV. In the Ustilago maydis system the rate of transformants was about 600 per $10^6$. A chimeric vector designed to introduce a mutation into a human bcl-2 gene was described in Kmiec, E. B., February 1996, Seminars in Oncology 23, 188.

A duplex CMV designed to repair the mutation in codon 12 of K-ras was described in Kmiec, E. B., December 1995, Advanced Drug Delivery Reviews 17, 333–40. The duplex CMV was tested in Capan 2, a cell line derived from a human pancreatic adenocarcinoma, using LIPOFECTIN™ to introduce the duplex CMV into the Capan 2 cells. Twenty four hours after the duplex CMV was introduced, the cells were harvested and genomic DNA was extracted; a fragment containing codon 12 of K-ras was amplified by PCR and the rate of conversion estimated by hybridization with allele specific probes. The rate of repair was reported to be approximately 18%.

A duplex CMV designed to repair a mutation in the gene encoding liver/bone/kidney type alkaline phosphatase was reported in Yoon, K., et al., March 1996, Proc. Natl. Acad. Sci. 93, 2071. The alkaline phosphatase gene was transiently introduced into CHO cells by a plasmid. Six hours later the duplex CMV was introduced. The plasmid was recovered at 24 hours after introduction of the duplex CMV and analyzed. The results showed that approximately 30 to 38% of the alkaline phosphatase genes were repaired by the duplex CMV.

WO 97/41411 and counterpart U.S. Pat. No. 5,760,012 to E. B. Kmiec, A. Cole-Strauss and K. Yoon, and the publication Cole-Strauss, A., et al., September 1996, SCIENCE 273, 1386 disclose duplex CMV that are used in the treatment of genetic diseases of hematopoietic cells, e.g., Sickle Cell Disease, Thalassemia and Gaucher Disease. U.S. Pat. No. 5,731,181 to E. B. Kmiec describes duplex CMV having non-natural nucleotides for use in specific, site-directed mutagenesis. The duplex CMV described in the applications and certain of the publications of Kmiec and his colleagues contain a central segment of DNA:DNA homoduplex and flanking segments of RNA:DNA hybrid-duplex or 2'-OMe-RNA:DNA hybrid-duplex.

The work of Kmiec and his colleagues concerned cells that are mitotically active, i.e., proliferating cells, at the time they are exposed to CMV. Kmiec and colleagues used a CMV/liposomal macromolecular carrier complex in which the CMV were mixed with a pre-formed liposome or lipid vesicle. In such a complex the CMV are believed to adhere to the surface of the liposome.

Kren et al., June 1997, Hepatology 25, 1462–1468, reported the successful use of a CMV in non-replicating, primary tissue-cultured rat hepatocytes to mutate the coagulation factor IX gene. Kren et al., March 1998, Nature Medicine 4, 285 reported the use of a CMV in vivo to introduce a genetic defect in the same gene.

2.2 The Use of a Polyethylenimine Macromolecular Carrier for In Vivo and In Vitro Transfection Branched chain polyethylenimine has been used as a carrier to introduce nucleic acids into eukaryotic cells both in vivo and in vitro. Boussif, O., et al., 1995, Proc. Natl. Acad. Sci. 92, 7297; Abdallah, B. et al., 1996, Human Gene Therapy 7, 1947. Boletta, A., et al., 1997, 8, 1243–1251. The in vitro use of galactosylated polyethylenimine to introduce DNA into cultured HepG2 hepatocarcinoma cell lines is reported by Zanta, et al., Oct. 1, 1997, Bioconjugate Chemistry 8, 839–844. The coupling of a protein ligand, transferrin, to polyethylenimine and its use to introduce a test gene into cultured cells by use of the transferrin receptor is described in Kircheis, R., et al., 1997, Gene Therapy 4, 409–4–18. Branched chain polyethylenimines contain secondary and tertiary amino groups having a broad range of pK's and, consequently these polyethylenimines have a substantial buffering capacity at a pH where polylysine has little or no capacity, i.e., less than about 8. Tang, M. K., & Szoka, F. C., 1997, Gene Therapy 4, 823–832. The use of branched chain polyalkanylimines, including polyethylenimine as carriers for the introduction of nucleic acids into cells is described in WO 96/02655 to J-P. Behr et al.

The successful in vivo and in vitro use of linear polyethylenimine to transfect a gene is reported by Ferrari, S., et al., 1997, Gene Therapy 4, 1100–1106. Compositions comprising a linear polyalkanylimine and a nucleic acid as disclosed in patent publication WO 93/20090 to S. Stein et al.

2.3 The Use of a Liposomal Carrier for In Vivo Transfection

The use of liposomes or lipid vesicles to introduce DNA encoding a foreign protein into cells has been described. The most frequently used techniques adhere the DNA to the surface of a positively charged liposome, rather than encapsulating the DNA, although encapsulated DNA techniques were known. U.S. Pat. Nos. 4,235,871 and 4,394,448 are relevant. The field is reviewed by Smith, J. G., et al., 1993, Biochim. Biophy. Acta 1154, 327–340 and Staubinger, R. M., et al., 1987, Methods in Enzymology 185, 512. The use of DOTAP, a cationic lipid in a liposome to transfect hepatic cells in vivo is described in Fabrega, A. J., et al., 1996, Transplantation 62, 1866–1871. The use of cationic lipid-containing liposomes to transfect a variety of cells of adult mice is described in Zhu, N., et al., 1993, Science 261, 209. The use of phosphatidylserine containing lipids to form DNA encapsulating liposomes for transfection is described in Fraley, R., et al., 1981, Biochemistry 20, 6978–87.

2.4 The Use of the Asialoglycoprotein Receptor for Hepatoceelular Specific Transfection U.S. Pat. Nos. 5,166,320 and 5,635,383 disclose the transfection of hepatocytes by forming a complex of a DNA, a polycationic macromolecular carrier and a ligand for the asialoglycoprotein receptor. In one embodiment, the macromolecular carrier was polylysine. The use of a lactosyl-cerebroside containing liposome to transfect a hepatocyte in vivo is described by Nandi, P. K., et al., 1986, J. Biol. Chem. 261, 16722–16722. The use of asialofetuin-labeled liposomes to transfect liver cells with a reporter plasmid is described in Hara et al., 1995, Gene Therapy 2, 764–788. The use of galactosylated poyethyleneimine to transfect cultured hepatocytes is described in Zanta M-A., et al. abst. pub. Oct. 1, 1997, Bioconjugate Chem., 8, 839–844.

2.5 Apo B100, Apo B48 and the Reduction of Serum LDL

Hepatic and Intestinal Lipoprotein Secretion: Both the liver and the intestines make and export lipoproteins for the transport of lipids. The lipoproteins are termed very low density lipoproteins (VLDL) and chylomicrons, respectively. VLDL and chylomicrons differ in size and in their major protein components. The major protein of VLDL is Apo B100, consisting of 4536 amino acids; the major protein of chylomicrons is Apo B48, which consists of the N-terminal 2152 amino acids of Apo B100. Apo B48 and Apo B100 are encoded by a single gene, the transcript of which is modified at nucleotide 6666 (codon 2179) by a sequence specific cytidine deaminase, termed apolipoprotein B mRNA editing enzyme (APOBE). The action of this enzyme converts a C to U and results in a stop codon.

Both VLDL, which contain Apo B100, and chylomicrons, which contain Apo B48 transport triglycerides in the vascular system to a delivery site. However, after triglyceride hydrolysis and delivery VLDL are transformed into LDL, while chylomicrons are not. High levels of circulating LDL per se and a high LDL:HDL ratio increase the risk of arterial atherosclerosis. Hence, it has been suggested that increasing the ratio of Apo B48 to Apo B100 would have a beneficial effect.

In many species of mammals, e.g., rats and mice, a high percentage of the lipid secretions of both liver and intestine contain Apo B48. Such species have markedly lower ratios of LDL:HDL. Greve J., et al., 1995, Proc. Zool. Soc., Calcutta, 47, 93–100. In others, such as humans and rabbits, hepatocytes lack APOBE and the hepatocytes consequently produce only VLDL.

One strategy to reduce the atherosclerosis in humans has been to introduce the gene for the catalytic component of the apolipoprotein B editing enzyme (APOBEC-1) under the control of a constitutive promoter to convert Apo B100 transcripts into Apo B48 transcripts. The transient expression of APOBEC-1 in the hepatocytes of normal and genetically hyperlipidemic Watanabe rabbit does cause a transient reduction in the levels of LDL. Greeve, J., et al., 1996, J. Lipid Res. 37, 2001–17. However, the uncontrolled production of APOBEC-1 is mutagenic and may cause hepatocellular hyperplasia and hepatocellular carcinoma. Yamanaka, S., et al., 1995, Proc. Natl. Acad. Sci. 92, 8483–8487.

Individuals who are homozygous or mixed heterozygotes for genes encoding truncated Apo B100 have been observed. Malloy et al., 1981, J. Clin. Invest. 67, 1441; Hardman, D. A., et al., 1991, J. Clin. Invest. 88, 1722. These individuals have low or absent LDL. For example, deletion of nucleotides 5391–5394 results in a frame shift mutation and a shortened Apo B (B37). These patients are most often asymptomatic. Steinberg, D., et al., 1979, J. Clin. Invest. 64, 292; Young, S. G., et al., 1988, Science 241, 591; Young, S. G., 1987, J. Clin. Invest. 79, 1831. Reviewed Linton, M. F., 1993, J. Lipid. Res. 34, 521; Kane, J. P. & Havel, R. J., 1995, Chapt. 57, *The Metabolic Basis of Inherited Disease*, ed. Scriver et al. (McGraw Hill, New York). Similarly, as many as 1 in every 3,000 persons has a serum cholesterol level of 100 mg/dl or less because the individual is heterozygous for a truncated Apo B gene. Ibid., p. 1866.

Truncations that result in an Apo B that are shorter than Apo B 31 do not circulate. Truncated Apo B 86, 87 and 90 have been observed. Apo B 86 and Apo B 87, are not associated with LDL while Apo B 90 is. Each mutation is associated with hypobetalipoproteinemia. Linton, M. L., et al., 1990, Clin. Res. 38, 286A (abstr.); Tennyson, G. E., et al., 1990, Clin. Res. 38, 482A (abstr.); Kruhl, E. S., et al., 1989, Arteriosclerosis 9, 856.

2.6 Apo E Polymorphism and Type III Hyperlipidemia

Apolipoprotein E is the major ligand for the LDL receptor for lipoproteins that contain Apo B48. There are three allelic forms of human Apo E that differ from each other by one or two amino acids: Apo E2 ($Cys^{112}$ $Cys^{158}$); Apo E3 ($Cys^{112}$ $Arg^{158}$); and Apo E4 ($Arg^{112}$ $Arg^{158}$). There is considerable geographical variation in the prevalences of the alleles. Excluding Africa, E2 ranges between 4% and 12%, E3 between 70% and 85% and E4 between 7.5 and 25%. In the Sudan, the prevalences are 8.1%, 61.9% and 29.10%, respectively. Mahley, R. W. & Rall, S. C., Jr., 1995, Chapt. 61, *The Metabolic Basis of Inherited Disease*, ed. Scriver et al. (McGraw Hill, New York). Thus approximately 1% of the North American and European population are Apo E 2/2 homozygotes. Of these homozygotes approximately between 2% and 10% display type III hyperlipidemia. Paradoxically, however, Apo E 2/2 homozygotes that have not developed overt Type III hyperlipidemia display lower than average LDL associated cholesterol. Davignon, J., 1988, Arteriosclerosis 8, 1.

The E4 allele is also associated with increased incidence of a major disease, Alzheimer's Disease, and with increased risk of coronary artery disease. Roses, A. D., 1996, Ann. NY Acad. Sci. 802, 50–57; Okumoto, K., & Fujiki, Y., 1997, Nature Genetics 17, 263; Kuusi, T., et al., 1989, Arteriosclerosis 9, 237. A polymorphism in the region 491 nt 5' to the transcription start site of the Apo E gene is also and independently associated with increased risk of Alzheimer's disease. Individuals homozygous for the −491-A genotype have an increased risk of Alzheimer's, while individuals homozygous or heterozygous for the −491 T genotype have no increased risk. Bullido, M. J., 1998, et al., Nature Genetics 18, 69–71.

The E2 allele in most individuals is associated with the lowest levels of serum cholesterol and LDL. However, about 5% of E2/E2 homozygous persons who are subject to environmental or genetic stress develop type III hyperlipidemia. The most common stressors are hypothyroidism, untreated diabetes mellitus, alcoholism and marked weight gain. Removal of the stressor usually results in control of the hyperlipidemia. Rare patients with type III hyperlipidemia have mutant Apo I genes. Mahley & Rail, ibid. Table 61-5.

3. SUMMARY OF THE INVENTION

The present invention concerns methods of treatment and/or prophylaxis which consists of the introduction of specific genetic alterations in genes of a subject individual. In one embodiment, the specific genetic alteration blocks the synthesis of Apo B100 and thereby reduces the level of LDL cholesterol. In an alternative embodiment, the specific alteration converts an Apo E4 allele to an Apo E3 or Apo E2 allele, which is associated with decreased risk of atherosclerosis and Alzheimer's Disease. In further alternative embodiments, the invention concerns the correction of inherited genetic defects in the genes of hepatocytes of individuals having a disease caused by such defects.

The invention can be practiced using any oligonucleotide or analog or derivative thereof, now known or hereafter developed, that can cause specific genetic alterations in the genome of the hepatocytes of the subject individual (hereafter a "recombinagenic oligonucleobase"), for example a chimeric mutational vector (CMV) as, for example, described in U.S. Pat. No. 5,565,350, No. 5,731,181, and No. 5,760,012. Alternatively, the recombinagenic oligonucleobase can be a heteroduplex mutational vector or a non-chimeric mutational vector as described in U.S. Pat. Nos. 6,004,804 and 6,010,907, each of which is hereby incorporated by reference.

In a preferred embodiment the recombinagenic oligonucleobase is complexed with a macromolecular carrier to which is attached a specific ligand. The ligand is selected to bind to a cell-surface receptor that is internalized into hepatocytes through clathrin-coated pits into endosomes. The cell surface receptors that bind such ligands are termed herein "clathrin-coated pit receptors". Examples of hepatic clathrin-coated pit receptors include the low density lipoprotein (LDL) receptor and the asialoglycoprotein receptor.

In specific embodiments the macromolecular carrier can be 1) an aqueous-cored lipid vesicle of between 25 nm and 400 nm diameter, wherein the aqueous core contains the CMV; 2) a lipid nanosphere of between 25 nm and 400 nm diameter, having a lipid core, wherein the lipid core contains a lipophilic salt of the CMV; or 3) a polycationic salt of the CMV. Examples of polycations for such salts include polyethylenimine, polylysine and histone H1. In one embodiment the polycation is a linear polyethylenimine (PEI) salt having a mass average molecular weight greater than 500 daltons and less than 1.3 Md. Alternatively the polycation can be a branched-chain polyethylenimine.

4. BRIEF DESCRIPTION OF THE FIGURES

FIGS. 2A–2E show the genomic sequence of human APO E gene with translation of exons (SEQ ID NOS:3, 60, 61 and 62). Introns are in lower case and exons are in upper case.

5. DEFINITIONS

Figure 1:
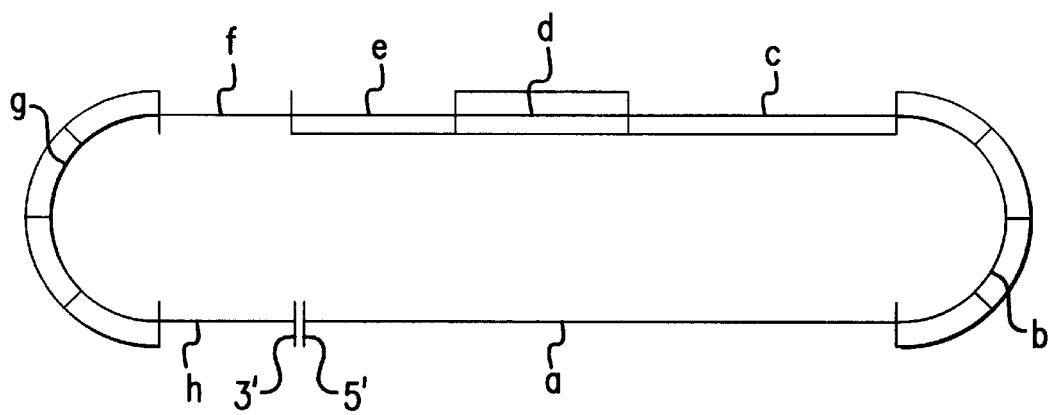
FIG. 1 is a schematic of one embodiment of CMV useful in the invention.

The invention is to be understood in accordance with the following definitions.

An oligonucleobase is a polymer of nucleobases, which polymer can hybridize by Watson-Crick base pairing to a DNA having the complementary sequence.

Nucleobases comprise a base, which is a purine, pyrimidine, or a derivative or analog thereof. Nucleobases include peptide nucleobases, the subunits of peptide nucleic acids, and morpholine nucleobases as well as nucleosides and nucleotides. Nucleosides are nucleobases that contain a pentosefuranosyl moiety, e.g., an optionally substituted riboside or 2'-deoxyriboside. Nucleosides can be linked by one of several linkage moieties, which may or may not contain a phosphorus. Nucleosides that are linked by unsubstituted phosphodiester linkages are termed nucleotides.

An oligonucleobase chain has a single 5' and 3' terminus, which are the ultimate nucleobases of the polymer. A particular oligonucleobase chain can contain nucleobases of all types. An oligonucleobase compound is a compound comprising one or more oligonucleobase chains that are complementary and hybridized by Watson-Crick base pairing. Nucleobases are either deoxyribo-type or ribo-type. Ribo-type nucleobases are pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

An oligonucleobase strand generically includes both oligonucleobase chains and segments or regions of oligonucleobase chains. An oligonucleobase strand has a 3' end and a 5' end. When a oligonucleobase strand is coextensive with a chain, the 3' and 5' ends of the strand are also 3' and 5' termini of the chain.

A region is a portion of an oligonucleobase, the sequence of which is derived from some particular source, e.g., a CMV having a region of at least 15 nucleotides having the sequence of a fragment of the human β-globin gene. A segment is a portion of a CMV having some characteristic structural feature. A given segment or a given region can contain both 2'-deoxynucleotides and ribonucleotides. However, a ribo-type segment or a 2'-deoxyribo-type segment contain only ribo-type and 2'-deoxyribo-type nucleobases, respectively.

6. DETAILED DESCRIPTION OF THE INVENTION 6.1 The Structure of the Chimeric Mutational Vector The Chimeric Mutational Vectors (CMV) are comprised of oligonucleobases, i.e., polymers of nucleobases, which polymers form Watson-Crick base pairs of purines and pyrimidines (hybridize), to DNA having the appropriate sequence. Each CMV is divided into a first and a second strand of at least 15 nucleobases each that are complementary to each other. The strands can be, but need not be, covalently linked. Nucleobases contain a base, which is either a purine or a pyrimidine or analog or derivative thereof. There are two types of nucleobases. Ribo-type nucleobases are ribonucleosides having a 2'-hydroxyl, substituted 2'-hydroxyl or 2'-halo-substituted ribose. All nucleobases other than ribo-type nucleobases are deoxyribo-type nucleobases. Thus, deoxy-type nucleobases include peptide nucleobases. As used herein, only a recombinagenic oligonucleobase that contains at least three contiguous ribo-type nucleobases that are hybridized to deoxyribo-type nucleobases are considered CMV.

The sequence of the first and second strands consists of at least two regions that are homologous to the target gene, i.e., have the same sequence as fragments of the target gene, and one or more regions (the "mutator regions") that differ from the target gene and introduce the genetic change into the target gene. The mutator region is located between homologous regions. In certain embodiments of the invention, each of the flanking homologous regions contains a ribo-type segment of at least three ribo-type nucleobases, that form a hybrid duplex, preferably at least six ribo-type nucleobases and more preferably at least ten ribo-type nucleobases in length, but not more than 25 and preferably not more than 20, more preferably not more than 15 ribo-type nucleobases. The hybrid-duplex-forming ribo-type oligonucleobase segments need not be adjacent to the mutator region. In certain embodiments of the invention the ribo-type oligonucleobase segments are separated from the mutator region by a portion of the homologous region comprising deoxyribo-type nucleobases. In these embodiments the mutator region is also composed of deoxyribo-type nucleobases. Accordingly, the mutator region and a portion of one or both homologous regions form an intervening segment of homo-duplex, which separates the two segments of hybrid-duplex.

The total length of all homologous regions is preferably at least 16 nucleobases and is more preferably from about 20 nucleobases to about 60 nucleobases in length.

Preferably, the mutator region consists of 20 or fewer bases, more preferably 6 or fewer bases and most preferably 3 or fewer bases. The mutator region can be of a length different than the length of the sequence that separates the regions of the target gene homology with the homologous regions of the CMV so that an insertion or deletion of the target gene results. When the CMV is used to introduce a deletion in the target gene there is no base identifiable as within the mutator region. Rather, the mutation is effected by the juxtaposition of the two homologous regions that are separated in the target gene. For the purposes of the invention, the length of the mutator region of a CMV that introduces a deletion in the target gene is deemed to be the length of the deletion. In one embodiment the mutator region is a deletion of from 6 to 1 bases or more preferably from 3 to 1 bases. Multiple separated mutations can be introduced by a single CMV, in which case there are multiple mutator regions in the same CMV. Alternatively multiple CMV can be used simultaneously to introduce multiple genetic changes in a single gene or, alternatively to introduce genetic changes in multiple genes of the same cell. Herein the mutator region is also termed the heterologous region.

In one embodiment the CMV is a single oligonucleobase chain of between 40 and 100 nucleobases. In an alternative embodiment, the CMV comprises a first and a second oligonucleobase chain, each of between 20 and 100 bases; wherein the first chain comprises the first strand and the second chain comprises the second strand. The first and second chains can be linked covalently by other than nucleobases or, alternatively, can be associated only by Watson-Crick base pairings. In an alternative embodiment the CMV is a first strand which is a single oligonucleobase chain and a second strand, complementary to the first which consists of two oligonucleobase chains, which are linked to the first strand chain by linkers. The combined length of the two chains of the second strand is the length of the first strand.

Linkers: Covalent linkage of the first and second strands can be made by oligo-alkanediols such as polyethyleneglycol, poly-1,3-propanediol or poly-1,4-butanediol. The length of various linkers suitable for connecting two hybridized nucleic acid strands is understood by those skilled in the art. A polyethylene glycol linker having from six to three ethylene units and terminal phosphoryl moieties is suitable. Durand, M. et al., 1990, Nucleic Acid Research 18, 6353; Ma, M. Y-X., et al., 1993, Nucleic Acids Res. 21, 2585–2589. A preferred alternative linker is bis-phosphorylpropyl-trans-4,4'-stilbenedicarboxamide.

Letsinger, R. L., et alia, 1994, J. Am. Chem. Soc. 116, 811–812; Letsinger, R. L. et alia, 1995, J. Am. Chem. Soc. 117, 7323–7328, which are hereby incorporated by reference. Such linkers can be inserted into the DMV using conventional solid phase synthesis. Alternatively, the strands of the DMV can be separately synthesized and then hybridized and the interstrand linkage formed using a thiophoryl-containing stilbenedicarboxamide as described in patent publication WO 97/05284, Feb. 13, 1997, to Letsinger R. L. et alia.

In a further alternative embodiment the linker can be a single strand oligonucleobase comprised of nuclease resistant nucleobases, e.g., a 2'-O-methyl, 2'-O-allyl or 2'-F-ribonucleotides. The tetranucleotide sequences TTTT, UUUU and UUCG and the trinucleotide sequences TTT, UUU, or UCG are particularly preferred nucleotide linkers.

Nucleotides: In an alternative embodiment the invention can be practiced using CMV comprising deoxynucleotides or deoxynucleosides and 2'-O substituted ribonucleotides or ribonucleosides. Suitable substituents include the substituents taught by the Kmiec Application, $C_{1-6}$ alkane. Alternative substituents include the substituents taught by U.S. Pat. No. 5,334,711 (Sproat) and the substituents taught by patent publications EP 629 387 and EP 679657 (collectively, the Martin Applications), which are hereby incorporated by reference. As used herein a 2' fluoro, chloro or bromo derivative of a ribonucleotide or a ribonucleotide having a substituted 2'-O as described in the Martin Applications or Sproat is termed a '2'-Substituted Ribonucleotide."Particular preferred embodiments of 2'-Substituted Ribonucleotides are 2'-fluoro, 2'-methoxy, 2'-propyloxy, 2'-allyloxy, 2'-hydroxylethyloxy, 2'-methoxyethyloxy, 2'-fluoropropyloxy and 2'-trifluoropropyloxy substituted ribonucleotides. In more preferred embodiments the 2'-Substituted Ribonucleotides are 2'-fluoro, 2'-methoxy, 2'-methoxyethyloxy, and 2'-allyloxy substituted nucleotides.

2'-Substituted Ribonucleosides are defined analogously. Particular preferred embodiments of 2'-Substituted Ribonucleosides are 2'-fluoro, 2'-methoxy, 2'-propyloxy, 2'-allyloxy, 2'-hydroxylethyloxy, 2'-methoxyethyloxy, 2'-fluoropropyloxy and 2'-trifluoropropyloxy substituted ribonucleotides. In more preferred embodiment on the 2'-Substituted Ribonucleosides are 2'-fluoro, 2'-methoxy, 2'-methoxyethyloxy, and 2'-allyloxy substituted nucleotides.

The term "nuclease resistant ribonucleoside" encompasses 2'-Substituted Ribonucleosides, including 2'-Substituted Ribonucleotides and also all 2'-hydroxyl ribonucleosides other than ribonucleotides. In a preferred embodiment, the CMV preferably includes at least three and more preferably six nuclease resistant ribonucleosides. In one preferred embodiment the CMV contains no nuclease sensitive ribonucleosides. In an alternative preferred embodiment, every other ribonucleoside is nuclease resistant. Certain 2'-blocking groups can be more readily synthesized for purines or pyrimidines. In one embodiment of the CMV only the ribonucleoside purines or only the ribonucleoside pyrimdines are nuclease resistant.

Recombinagenic oligonucleobases, including non-chimeric mutational oligonucleobases and improved CMV and their use in eukaryotic cells and cell-free systems are described in U.S. Pat. Nos. 6,004804 and 6,010,804, which are each hereby incorporated in their entirety. These mutational oligonucleobases can be used in the same manner as the CMV described in this application.

6.2 The Gene-Specific Structure of the Chimeric Mutational Vector

FIG. 1 shows a diagram of a CMV according to one embodiment of the invention. In the Figure segments "a"

and "c–e" are target gene specific segments of the CMV. The sequence of segment "a" and "c–e" are complements of each other. The sequence of segments "f" and "h" are also complements of each other but are unrelated to the specific target gene and are selected merely to ensure the stability of hybridization in order to protect the 3' and 5' ends. Additional protection of the 3' and 5' ends can be accomplished by making the 5' and 3' most internucleotide bonds a phosphorothioate, phosphonate or any other nuclease resistant bond. The sequence of segments "f" and "h" can be 5'-GCGCG-3' or permutations thereof. Segments "g" and "b" can be any linker that covalently connects the two strands, e.g., four unpaired nucleotides or an alkoxy oligomer such as polyethylene glycol. When segments "g" and "b" are composed of other than nucleobases, then segments "a", c–f" and "h" are each an oligonucleobase chain.

The ribo-type nucleobase segments are segments "c" and "e," which form hybrid-duplexes by Watson-Crick base pairing to the complementary portions of segment "a." The segment "a" can have the sequence of either the coding or non-coding strand of the gene.

Table I contains SEQ ID No. 4–No. 24, which are examples of the sequences that can be used to practice the invention. The mutator region in each case is underlined and in bold. CMV having a segment "a" with a sequence selected from the sequences of Table I can be used to practice the invention. Alternatively, segment "a" may have the sequence of the complement of a sequence of Table I. As used herein, a CMV or other type of recombinagenic oligonucleobase comprises a sequence if either strand of the CMV or recombinagenic oligonucleobase comprises the sequence or comprises a sequence containing ribo-type nucleobases with uracil bases replacing thymine bases. Thus, for example, a CMV having the sequence 5'-agucuggaugGGTAAgccgcccuca-3' (SEQ ID No. 26) is considered to have the sequence of SEQ ID No: 4, wherein the lower case letters denote ribo-type nucleobases and the UPPER CASE letters denote deoxyribo-type nucleobases.

Subjects can be treated with a recombinagenic oligonucleobase specific for Apo B or Apo E according to the guidance of the Factor IX example below. More particularly the recombinagenic oligonucleobase can be given in divided doses at intervals that permit determining of the phenotypic effect of the dose, i.e., evaluation of the extent of the decline in LDL cholesterol and observation for adverse reactions. A reduction of the subject's fasting LDL serum cholesterol to below the level of the 5th percentile of the age-matched population (80–90 mg/dl) can be used as a therapeutic end point; alternatively reduction of fasting LDL serum cholesterol to below the average age-matched normal value (100–140) can be used. The number and size of the dose(s) can be modified to control the extent of the phenotypic effects. In the event that reversal of the specific genetic changes appear desirable, a recombinagenic oligonucleobase having a sequence appropriate to reverse of the specific changes can be administered so that the fraction of unmodified Apo B or Apo E genes can be increased. Modification of the dose size and number and the administration of a reversing recombinagenic oligonucleobase permits the adjustment of the number of altered genes in the subject so that a predetermined amount of the phenotypic change can be effected.

6.2.1 Specific Alterations of the Apo B Gene

SEQ ID No. 1 contains the Apo B amino acid sequence and SEQ ID No. 2 contains the Apo B cDNA sequence.

The level of serum cholesterol and particularly of LDL-associated cholesterol can be reduced in a subject by introducing mutations into the subject's hepatic Apo B genes. The mutation can be any mutation that causes termination of the Apo B translation product between amino acid 1433 (Apo B 31) and amino acid 3974 (Apo B 87). (The amino acid numbering for Apo B in this specification refers to the 4553 amino acid primary translation product, i.e., mature Apo B100 plus the 27 amino acid leader sequence. Mature Apo B 100 consists of 4536 amino acids and mature Apo B 48 consists of 2152 amino acids.) Preferably the translation product is terminated between amino acids 1841 (Apo B 40) and 2975 (Apo 65). The translation product can be terminated by introducing a frameshift mutation, i.e., by adding or deleting one or two nucleotides from the gene, or by introducing a stop codon (a TAA, TAG or TGA). The preferred stop codon is TAA. To monitor the introduction of the mutation it is preferred to have the mutation introduce or remove a palindromic sequence, which is the substrate of a restriction enzyme.

The sequence of the CMV is selected to have two homologous regions of at least 10 nucleobases and preferably at least 12 nucleobases each with a fragment of the Apo B gene located between nucleotides encoding amino acid 1433 (nt 4425) and 3974 (nt 12,048) and preferably located between the nucleotides encoding amino acids 1841 (nt 5649) and 2975 (nt 9051). In this specification, nt 6666 is the first nucleotide of codon 2180, the nucleotide that is converted by APOBE. In a preferred embodiment, the two homologous regions are separated by a single nucleobase in the sequence of the Apo B gene, where the CMV introduces a base substitution in the Apo B gene. Alternatively, the two homology regions can be adjacent in the Apo B gene and separated by a single or double nucleobase in the CMV, such that a one or two base insertion results from the action of the CMV on the Apo B gene. Alternatively, the homologous regions can be separated in the Apo B gene by one or two nucleotides that are deleted from the sequence of the CMV, such that the action of the CMV results in a one or two base deletion in the gene.

Nucleotides 4425–12,048 of the Apo B cDNA are encoded by exon 26 (nt 4342–11913), exon 27 (nt 11914–12028) and exon 28 (nt 12029–12212); see Table I, and GENBANK Accession No.19828, which is hereby incorporated by reference. When an alteration is to be made at a position 3' of nt 11913, attention must be paid to the exon/intron boundary. Mutations that are located within 10–15 nucleotides of the exon/intron boundary must be identified so that the homology region of the CMV continues with the sequence of the intron and not the exon.

The homologous regions can be each from 10 to about 15 nucleobases in length; the two regions need not be of the same length. The fraction of nucleobases that contain a guanine or cytosine base is a design consideration (the GC fraction). It is preferred that when the homologous region contains 12 or fewer nucleobases, the GC fraction be at least 33% and preferably at least 50%. When the GC fraction is less than 33% the length of the homologous regions is preferably 13, 14 or 15 nucleobases.

Table I contains 17 exemplary embodiments, SEQ ID No. 4–20, of CMV sufficient for the practice of the embodiments of the invention described in this section. Suitable CMV can be made using nt 3–23 of SEQ ID No. 4–10, 12, and 16–20. SEQ ID NO. 11 and 13–15 have a lower GC fraction; CMV sufficient for the practice of the invention can be made containing residues 3–25 of SEQ ID NO. 11 and 13–15.

6.2.2 Specific Alterations of the Apo E Gene

In a further embodiment, the invention consists of introducing specific alterations to the Apo E gene. E4 homozygous individuals are at increased risk for atherosclerosis, particularly coronary artery disease, and Alzheimer's disease. Therefore, one embodiment of the present invention is the introduction of the substitution ArgCys at residues 112, to convert an E4 allele to an E3 allele, and optionally at residue 158 to convert an E3 or E4 allele into an E2 allele of an Apo E gene of an hepatocyte of a subject. The substitutions can be introduced using an oligonucleobase containing the sequence of nt 3–23 of SEQ ID No. 22 and No. 23 or complement thereof and more preferably of an oligonucleobase containing SEQ ID No. 22 and No. 23 or complement thereof. In addition, in individuals lacking genetic or environment stressors, the E2 allele results in a lowered LDL level and a decreased risk of atherosclerosis and coronary artery disease. Thus, these risks in an E3/E3 individual can be reduced by introduction of the (Arg→Cys)$^{158}$ substitution to convert the individual Apo E genes to E2 alleles.

Apo E2/E2 homozygous individuals who are suffering from Type III hyperlipidemia can be treated by converting E2 alleles to E3 alleles by making a Cys→Arg$^{158}$ substitution. Such a substitution can be made using an oligonucleobase containing the sequence of nt 3–23 of SEQ ID No. 24 or complement thereof and more preferably of an oligonucleobase containing SEQ ID No. 24 or complement thereof.

Independent of the Apo E allele, individuals who are homozygous for −491-A are at increased risk to develop Alzheimer's Disease. Bullido, M. J., 1998, et al., Nature Genetics 18, 69–71. These individuals can be advantageously treated with an oligonucleobase containing the sequence of nt 3–23 of SEQ ID No. 25.

6.2.3 Repair of Mutations of the Apo B and Apo E Gene

SEQ ID No. 3 contains the Apo E genomic DNA sequence.

A further embodiment of the invention concerns the use of CMV to repair mutations in the Apo B and Apo E genes that cause hypobetalipoproteinemia and dysbetal iproteinemia, respectively. Mutations that are located within 10–15 nucleotides of the exon/intron boundary must be identified so that the homology region of the CMV continues with the sequence of the intron and not the exon. The genomic sequence of Apo E4 indicating the exon and intron boundaries is given in Paik et al., 1985, Proc. Natl. Acad. Sci. 82, 3445, which is hereby incorporated by reference. The exon/intron boundaries of the Apo B gene are given in Table 11 along with the GENBANK accession numbers for the genomic sequence of Apo B.

6.3 Formulations Suitable for In Vivo Use

The prior art formulations of CMV and a macromolecular carrier are of limited utility for in vivo use because of their low capacity for CMV and because the CMV is not protected from extracellular enzymes. The invention provides three alternative macromolecular carriers that overcome the limitations of the prior art. The carriers are polyethylenimine (PEI), aqueous-cored lipid vesicles, which are also termed unilamellar liposomes and lipid nanospheres.

Each of the carriers can be further provided with a ligand that is complementary to a cell-surface protein of the target cell. Such ligands are useful to increase both the amount and specificity of the uptake of CMV into the targeted cell. In one embodiment of the invention the target cell is a hepatocyte and the ligand is a galactose saccharide or lactose disaccharide that binds to the asialoglycoprotein receptor.

6.3.1 Polycationic Carriers

The invention can be practiced using any polycation that is non-toxic when administered to cells in vitro or to subjects in vivo. Suitable examples include polybasic amino acids such as polylysine, polyarginine, basic proteins such as histone H1, and synthetic polymers such as the branched-chain polyethylenimine:

(—NHCH$_2$CH$_2$—)$_x$[—N(CH$_2$CH$_2$NH$_2$)CH$_2$CH$_2$—]$_y$.

The invention can be practiced with any branched chain polyethylenimine (PEI) having an average molecular weight of greater than about 500 daltons, preferably greater than between about 10 Kd and more preferably about 25 Kd (mass average molecular weight determined by light scattering) The upper limit of suitability is determined by the toxicity and solubility of the PEI. Toxicity and insolubility of molecular weights greater than about 1.3 Md makes such PEI material less suitable. The use of high molecular weight PEI as a carrier to transfect a cell with DNA is described in Boussif, O. et al., 1995, Proc. Natl. Acad. Sci. 92, 7297, which is hereby incorporated by reference. PEI solutions can be prepared according to the procedure of Boussif et al.

The CMV carrier complex is formed by mixing an aqueous solution of CMV and a neutral aqueous solution of PEI at a ratio of between 9 and 4 PEI nitrogens per CMV phosphate. In a preferred embodiment the ratio is 6. The complex can be formed, for example, by mixing a 10 mM solution of PEI, at pH 7.0 in 0.15 M NaCl with CMV to form a final CMV concentration of between 100 and 500 nM.

In addition a ligand for a clathrin-coated pit receptor can be attached to the polycation or to a fraction of the polycations. In one embodiment the ligand is a saccharide or disaccharide that binds to the asialoglycoprotein receptor, such as lactose, galactose, or N-acetylgalactosamine. Any technique can be used to attach the ligands. The optimal ratio of ligand to polyethylene subunit can be determined by fluorescently labeling the CMV and injecting fluorescent CMV/molecular carrier/ligand complexes directly into the tissue of interest and determining the extent of fluorescent uptake according to the method of Kren et al., 1997, Hepatology 25, 1462–1468.

Good results can be obtained using a 1:1 mixture of lactosylated PEI having a ratio of 0.4–0.8 lactosyl moieties per nitrogen and unmodified PEI. The mixture is used in a ratio of between 4 and 9 PEI nitrogens per CMV phosphate. A preferred ratio of oligonucleotide phosphate to nitrogen is 1:6. Good results can be obtained with PEIs having a mass average molecular weight of 25 Kd and 800 Kd which are commercially available from Aldrich Chemical Co., Catalog No. 40,872–7 and 18,197–8, respectively. Linear PEI such as that described in Ferrarri, S., et al., 1997, Gene Thereapy 4, 1100–1106 and sold under the trademenark EXGEN 500™ is particularly suitable for the practice of the invention because of its lower toxicity compared to branched-chain PEI.

In an alternative embodiment the polycationic carrier can be a basic protein such as histone H1, which can be substituted with a ligand for a clathrin-coated pit receptor. A 1:1 (w/w) mixture of histone and CMV can be used to practice the invention.

6.3.2 Lipids that are Useful in Carriers

The selection of lipids for incorporation into the lipid vesicle and lipid nanosphere carriers of the invention is not critical. Lipid nanospheres can be constructed using semi-purified lipid biological preparations, e.g., soybean oil (Sigma Chem. Co.) and egg phosphatidyl choline (EPC) (Avanti Polar Lipids). Other lipids that are useful in the preparation of lipid nanospheres and/or lipid vesicles include neutral lipids, e.g., dioleoyl phosphatidylcholine (DOPC), and dioleoyl phosphatidyl ethanolamine (DOPE), anionic lipids, e.g., dioleoyl phosphatidyl serine (DOPS)

and cationic lipids, e.g., dioleoyl trimethyl ammonium propane (DOTAP), dioctadecyldiamidoglycyl spermine (DOGS), dioleoyl trimethyl ammonium (DOTMA) and DOSPER (1,3-di-oleoyloxy-2-(6-carboxy-spermyl)-propylamide tetraacetate, commercially available from Boehringer-Mannheim). Additional examples of lipids that can be used in the invention can be found in Gao, X. and Huany, L., 1995, Gene Therapy 2, 710. Saccharide ligands can be added in the form of saccharide cerebrosides, e.g., lactosylcerebroside or galactocerebroside (Avanti Polar Lipids).

The particular choice of lipid is not critical. Hydrogenated EPC or lysolecithin can be used in place of EPC. DPPC (dipalmitoyl phosphatidylcholine), can be incorporated to improve the efficacy and/or stability of the delivery system.

6.3.3 The Construction of Lipid Nanosphere Carriers

Lipid nanospheres can be constructed by the following process. A methanol or chloroform methanol solution of phospholipids is added to a small test tube and the solvent removed by a nitrogen stream to leave a lipid film. A lipophilic salt of CMV is formed by mixing an aqueous saline solution of CMV with an ethanolic solution of a cationic lipid. Good results can be obtained when the cationic species are in about a 4 fold molar excess relative to the CMV anions (phosphates). The lipophilic CMV salt solution is added to the lipid film, vortexed gently followed by the addition of an amount of neutral lipid equal in weight to the phospholipids. The concentration of CMV can be up to about 3% (w/w) of the total amount of lipid.

After addition of the neutral lipid, the emulsion is sonicated at 4° C. for about 1 hour until the formation of a milky suspension with no obvious signs of separation. The suspension is extruded through polycarbonate filters until a final diameter of about 50 nm is achieved. When the target cell is a reticuloendothelial cell the preferred diameter of the lipid nanospheres is about 100–200 nm. The CMV-carrying lipid nanospheres can then be washed and placed into a pharmaceutically acceptable carrier or tissue culture medium. The capacity of lipid nanospheres is about 2.5 mg CMV/500 $\mu$l of a nanosphere suspension.

6.3.4 The Construction of Lipid Vesicles

A lipid film is formed by placing a chloroform methanol solution of lipid in a tube and removing the solvent by a nitrogen stream. An aqueous saline solution of CMV is added such that the amount of CMV is between 20% and 50% (w/w) of the amount of lipid, and the amount of aqueous solvent is about 80% (w/w) of the amount of lipid in the final mixture. After gentle vortexing the liposome-containing liquid is forced through successively finer polycarbonate filter membranes until a final diameter of about 50 nm is achieved. The passage through the successively finer polycarbonate filter results in the conversion of polylamellar liposomes into unilamellar liposomes, i.e., vesicles. When the target cell is a reticuloendothelial cell the preferred diameter of the lipid nanospheres is about 100–200 nm. The CMV-carrying lipid nanospheres can then be washed and placed into a pharmaceutically acceptable carrier or tissue culture medium.

The CMV are entrapped in the aqueous core of the vesicles. About 50% of the added CMV is entrapped.

A variation of the basic procedure comprises the formation of an aqueous solution containing a PEI/CMV condensate at a ratio of about 4 PEI imines per CMV phosphate. The condensate can be particularly useful when the liposomes are positively charged, i.e., the lipid vesicle contains a concentration of cations of cationic lipids such as DOTAP, DOTMA or DOSPER, greater than the concentration of anions of anionic lipids such as DOPS. The capacity of lipid vesicles is about 150 $\mu$g CMV per 500 $\mu$l of a lipid vesicle suspension.

In a preferred embodiment the lipid vesicles contain a mixture of the anionic phospholipid, DOPS, and a neutral lipid such as DOPE or DOPC. Other negatively charged phospholipids that can be used to make lipid vesicles include dioleoyl phosphatidic acid (DOPA) and dioleoyl phosphatidyl glycerol (DOPG). In a more preferred embodiment the neutral lipid is DOPC and the ratio of DOPS:DOPC is between 2:1 and 1:2 and is preferably about 1:1. The ratio of negatively charged to neutral lipid should be greater than 1:9 because the presence of less than 10% charged lipid results in instability of the lipid vesicles because of vesicle fusion.

A particular lipid vesicle formulation can be tested by using the formulation to transfect a target cell population with a plasmid of about 5.0 kb in length that expresses some readily detectable product in the transfected target cell. Lipid vesicles can be used to transfect a cell with the plasmid if the plasmid is condensed with PEI at an imine:phosphate ratio of about 9–4:1. The capacity of the lipid vesicle formulation to transfect a cell with a plasmid is indicative of the formulation's capacity to introduce a CMV into a cell and effect a transmutation.

Certain lipids, particularly the polycationic lipids, can be toxic to certain cell lines and primary cell cultures. The formulation of the lipid vesicles should be adjusted to avoid such toxic lipids.

Ligands for clathrin-coated pit receptors can be introduced into the lipid vescicles by a variety of means. Cerebrosides, such as lactocerebroside or galactocerebroside can be intorduced into the lipid mixture and are incorporated into the vesicle to produce a ligand for the asialoglycoprotein receptor.

In an alternative embodiment the lipid vesicle further comprise an integral membrane protein that inserts itself into the lipid bilayer of the vesicle. In a specific embodiment the protein is a fusigenic (F-protein) from the virus alternatively termed Sendai Virus or Hemagglutinating Virus of Japan (HVJ). The preparation and use of F-protein containing lipid vesicles to introduce DNA into liver, myocardial and endothelial cells have been reported. See, e.g., U.S. Pat. No. 5,683,866, International Application PCT JP97/00612 (published as WO 97/31656). See also, Ramani, K., et al., 1996, FEBS Letters 404, 164–168; Kaneda, Y., et al., 1989, J. Biol. Chem. 264, 121126–12129; Kenada, Y., et al., 1989, Science 243, 375; Dzau, V. J., et al., Proc. Natl. Acad. Sci. 93, 11421–11425; Aoki, M., et al., 1997, J.Mol.Cardiol. 29, 949–959.

6.4 Diseases and Disease-Specific CMV

The invention can be used to correct any disease-causing mutation, in which the mutation results in the change of one or more nucleotides or in the insertion or deletion of from one to about 30 nucleotides. In a preferred embodiment, the deletion or insertion is of from one to about six nucleotides. The disease-causing mutation is corrected by administering a CMV containing the sequence of the wild type gene that is homologous to the locus of the mutation. The CMV is constructed so that there are regions of homology with the mutant DNA sequence flanking the heterologous region, i.e, the region of the CMV that contains the portion of the wild-type sequence that is absent from the mutant. When the mutation consists of an insertion, the heterologous region of the CMV is considered to be the point which is homologous to the site of the insertion. Accordingly, the length of the heterologous region of the CMV is deemed to be the length of the insertion in the mutant sequence. Note that the sequence of the CMV is determined by the location of the mutation, however, the sequence of the mutation is not important. Rather, the sequence of a CMV is always the sequence of the wild type gene or a desired related sequence. In each of the sequences that follow the heterologous region is underlined.

A first embodiment of the invention is a CMV that can be used to correct the mutation that causes the von Willebrand's Disease. A CMV to correct this mutation contains the sequence 5'-CTC GGA GAG C CCC CTC GCA-3' (SEQ ID No. 27), the sequence of a mixed ribo-deoxyribo oligonucleobase having the same sequence of bases or a sequence that differs by the substitution of the thymine by uracil, or the sequence of the complement thereof. The tissue in which the von Willebrand's factor gene needs to be corrected is the vascular endothelium.

A further embodiment of the invention is a CMV that can be used to correct the mutation that causes Hemophilia B, which is an A→C substitution at nt 1234 of the human coagulation Factor IX gene. CMV to correct this mutation contains the sequence 5'-CAA GGA GAT AGT GGG GGA C-3' (SEQ ID No. 28), the sequence of a mixed ribo-deoxyribo oligonucleobase having the same sequence of bases or a sequence that differs by the substitution of the thymine by uracil, or the sequence of the complement thereof. The invention can be used to correct other mutations in the human coagulation Factor IX gene, the sequence of which is given in Kurachi, K., et al., 1982, Proc. Natl. Acad. Sci. U.S.A. 79, 6461–6464, which is hereby incorporated by reference. The tissue in which the factor IX gene needs to be corrected is the hepatocellular liver.

A further embodiment of the invention is a CMV that can be used to correct the Z-mutation that causes α1-antitrypsin deficiency. The Z mutation is a G→A substitution located at nt 1145 of the human α1-antitrypsin gene. CMV to correct this mutation contains the sequence 5'-ACC ATC GAC GAG AAA GGG A-3' (SEQ ID No. 29), the sequence of a mixed ribo-deoxyribo oligonucleobase having the same sequence of bases or a sequence that differs by the substitution of the thymine by uracil, or the sequence of the complement thereof. The invention can be used to correct other mutations in the α1-antitrypsin gene, the sequence of which is given in Long, G. L., et al., 1984, Biochemistry 23, 4828–4837, which is hereby incorporated by reference. The tissue in which the α1-antitrypsin gene needs to be corrected is the hepatocellular liver.

A further embodiment of the invention is a CMV that can be used to correct a mutation in the low density lipoprotein receptor (LDLR) that causes familial hypercholesterolemia (FH). There is no single mutation that causes the majority of FH cases. Surveys of the more than 105 point mutations or insertions or deletions of 25 nt or fewer that cause FH can be found in Hobbs, H. H., et al., 1992, Hum. Mutat. 1, 445466 and Leren, T. P., et al., Hum. Genet. 95, 671–676, which are hereby incorporated by reference in their entirety. The complete sequence of the human LDLR cDNA is published in Yamamoto, T., et al., 1984, CELL 39, 27–38. The tissue in which the LDLR can be corrected to obtain amelioration of FH is the hepatocellular liver.

A further embodiment of the invention is a CMV that can be used to correct a mutation in the glucocerebrosidase gene that causes Gaucher Disease. The structure of CMV that can be used to correct a Gaucher Disease mutation can be found in commonly licensed U.S. application Ser. No. 08/640,517, now U.S. Pat. No. 5,760,012. The tissue in which the glucocerebrosidase mutation can be corrected to obtain amelioration of Gaucher Disease is the reticuloendothelial (Kupffer Cell) liver.

A further embodiment of the invention is a CMV that can be used to correct a mutation in the glucose-6-phosphatase (G-6-P) gene that causes type 1 Glycogen Storage Disease (GSD). The complete sequence of the human G-6-P is given in Lei, K.-J., et al., SCIENCE 262, 580, which is hereby incorporated by reference. The two most common mutations that cause type 1 GSD are C→T at nt 326, C→T at nt 1118, and an insertion of TA at nt 459, as described in Lei, K.-J., et al., J. Clin. Investigation 95, 234–240, which is hereby incorporated by reference. CMV to correct the two most common mutations contain the sequence 5'-TTT GGA CAG CGT CCA TAC T-3' (SEQ ID No. 30), or 5'-TGC CTC GCC CAG GTC CTG G-3' (SEQ ID No. 31), the sequence of a mixed ribo-deoxyribo oligonucleobase having the same sequence of bases or a sequence that differs by the substitution of the thymine by uracil, or the sequence of the complement thereof.

A further embodiment of the invention is a CMV that can be used to correct a mutation in the Ornithine Transcarbamylase (OTC) gene an X-linked gene that catalyzes the condensation of ornithine and carbamyl phosphate to yield citruline and phosphate. The complete sequence of the human OTC cDNA is given in Horwich, A. L., et al., 1984, Science 224, 1068, which is hereby incorporated by reference. The structure of OTC gene and a review of the structure of identified mutants is reviewed in Tuchman, M., 1992, Human Mutation 2, 174.

A further embodiment of the invention is a CMV that can be used to correct a mutation in the human UDP-glucuronosyltransferase gene that causes Crigler-Najjar syndrome. The sequence of the human UDP-glucuronosyltransferase gene is given in Bosma, P. J., et al., 1992, Hepatology, 15, 941–7, which is hereby incorporated by reference. The tissue in which the UDP-glucuronosyltransferase gene can be corrected to obtain amelioration of Crigler-Najjar syndrome is the hepatocellular liver.

A further embodiment of the invention is a CMV that can be used to correct a mutation in a galactose-1-phosphate uridyltransferase gene that cause galactosemia. The sequence of the human galactose-1-phosphate uridyltransferase gene is described in Flack, J. E., et al., 1990 Mol. Biol. Med. 7, 365, and the molecular biology and population genetics of galactosemia are described in Reichert, J. K. V., et al., 1991, Proc. Natl. Acad. Sci. 88, 2633–37 and Reichert, J. K. V., et al., 1991, Am. J. Hum. Gen. 49, 860, which are hereby incorporated by reference. The most common mutation that causes galactosemia is Q→R at amino acid 188. The CMV to correct this mutation contains the sequence 5'-CC CAC TGC CAG GTA TGG GC-3' (SEQ ID No. 32), the sequence of a mixed ribo-deoxyribo oligonucleobase having the same sequence of bases or a sequence that differs by the substitution of the thymine by uracil, or the sequence of the complement thereof.

A further embodiment of the invention is a CMV that can be used to correct a mutation in the phenylalanine hydroxylase (PAH, phenylalanine 4-monooxygenase, EC 1.14.16.1) that cause phenylketonuria (PKU) or hyperphenylalaninemia. The molecular and population genetics of phenylketonuria are described in Woo, SLC, 1989, Biochemistry 28, 1–7, the sequence of human PAH is described in Kowk, S. C. M., et al., 1985, Biochemistry 28, 556–561, which are hereby incorporated by reference. Further examples of PKU-causing mutations can be found in Sworniczak, B., et al., 1992, Hum. Mutat. 1, 138–146.

6.5 The Use of the Formulations In Vivo

The CMV of the invention can be parenterally administered directly to the target organ at a dose of between 50 and 250 µg/gm. When the target organ is the liver muscle or kidney, the CMV/macromolecular carrier complex can be injected directly into the organ. When the target organ is the liver, intravenous injection into the hepatic or portal veins of a liver, having temporarily obstructed circulation can be used. Alternatively the CMV/macromolecular complex can further comprise a hepatic targeting ligand, such as a lactosyl or galactosyl saccharide, which allows for administration of the CMV/macromolecular complex intravenously into the general circulation.

When the target organ is the lung or a tissue thereof, e.g., the bronchiolar epithelium CMV/macromolecular complex can be administered by aerosol. Small particle aerosol delivery of liposomal/DNA complexes is described in Schwarz L. A., et al., 1996, Human Gene Therapy 7, 731–741.

When the target organ is the vascular endothelium, as for example in von Willebrand's Disease, the CMV/macromolecular complex can be delivered directly into the systemic circulation. Other organs can be targeted by use of liposomes that are provided with ligands that enable the liposome to be extravasated through the endothelial cells of the circulatory system.

For enzymatic defects, therapeutic effects can be obtained by correcting the genes of about 1% of the cells of the affected tissue. In a tissue in which the parenchymal cells have an extended life, such as the liver, treatments with CMV can be repeatedly performed to obtain an increased therapeutic effect.

7. EXAMPLES

7.1 CMV/Macromolecular Carrier Complexes

7.1.1 Lipid Nanospheres

Materials

Egg phosphatidylcholine (EPC), DOTAP and galactocerebroside (Cc) (Avanti Polar Lipids); soybean oil (Sigma Chemical Co.); dioctadecyldiamidoglycyl spermine (DOGS®) (Promega).

Methods

EPC, DOTAP and Gc were previously dissolved at defined concentrations in chloroform or anhydrous methanol and stored in small glass vials in desiccated containers at −20° C. until use. EPC (40–45 mg), DOTAP (200 µg) and Gc (43 µg) solutions were aliquoted into a small 10×75 mm borosilicate tube and solvents removed under a stream of nitrogen. CMV were diluted in 0.15 M NaCl (~80–125 µg/250–300 µl); DOGS (as a 10 mg/ml solution in ethanol) was diluted into 250–300 µl 0.15 M NaCl at 3–5 times the weight of added CMV. The two solutions were mildly vortexed to mix contents and then CMV solution was added slowly to the DOGS solution. The contents were mixed by gentle tapping and inverting the tube a few times. The DOGS-complex solution was added to the dried lipids followed by soybean oil (40–45 mg), the mixture was vortexed on high for a few seconds and bath sonicated in a FS-15 (Fisher Scientific) bath sonicator for ~1 hr in a 4° C. temperature controlled room. Occasionally, the tube was removed from the bath and vortexed. When a uniform looking, milky suspension was formed (with no obvious separation of oil droplets), it was extruded through a series of polycarbonate membranes down to a pore size of 50 nm. Preparations were stored at 4° C. until use and vortexed before use.

7.1.2 Negatively Charged Targeted Lipid Vesicles

Materials

Dioleoyl phosphatidylcholine (DOPC), dioleoyl phosphatidylserine (DOPS), galactocerebroside (Gc) or lactosylcerebroside, (Avanti Polar Lipids).

Methods

DOPS, DOPC and Gc at a molar ratio of 1:1:0.16 (500 μg total lipid) were dissolved in chloroform:methanol (1:1 v/v) and then dried under a stream of nitrogen to obtain a uniform lipid film. The CMV were diluted in 500 μl of 0.15 M NaCl (approximately 100–250 μg/500 μl). The solution was added to the lipid film at room temperature. Lipids were dispersed entirely by alternate mild vortexing and warming (in a water bath at 37–42° C.). After a uniform milky suspension was formed, it was extruded through a series of polycarbonate membranes (pore sizes 0.8, 0.4, 0.2, 0.1 and 0.05 μm) using a Liposofast® mini-extruder. Extrusion was done 5 to 7 times through each pore size. After preparation, lipid vesicles were stored at 4° C. until use. Under these conditions the lipid vesicles were stable for at least one month. The final product can be lyophilized.

7.1.3 Neutral Targeted Lipid Vesicles

Materials

Dioleoyl phosphatidylcholine (DOPC), dioleoyl phosphatidylethanolamine (DOPE), galactocerebroside (Gc) or lactosylcerebroside, (Avanti Polar Lipids).

Methods

DOPC, DOPE and Gc (1:1:0.16 molar ratio) or DOPC:Gc (1:0.08) were dissolved in chloroform:methanol (1:1 v/v) and then dried under a stream of nitrogen to obtain a uniform lipid film. The oligonucleotides (or chimeric molecules) were diluted in 500 μl of 0.15 M NaCl (approximately 100–250 μg/500 μl). The solution was added to the lipid film at room temperature. Lipids were dispersed entirely by alternate mild vortexing and warming (in a water bath at 37–42° C.). After a uniform milky suspension was formed, it was extruded through a series of polycarbonate membranes (pore sizes 0.8, 0.4, 0.2, 0.1 and 0.05 μm) using a Liposofast® mini-extruder. Extrusion was done 5 to 7 times through each pore size. After preparation, lipid vesicles were stored at 4° C. until use. The size of the lipid vesicles of the preparation was stable for about 5 days.

7.1.4 Positively Charged Targeted Lipid Vesicles

Materials

Dioleoyl phosphatidylcholine (DOPC), dioleoyl trimethylammonium propane (DOTAP), galactocerebroside (Gc) or lactosylcerebroside, (Avanti Polar Lipids). Polyethylenimine (PEI) (M.W. 800 Kd), Fluka Chemicals.

Methods

DOPC, DOTAP and Gc (6:1:0.56 molar ratio) (500 μg total lipid) were dissolved in chloroform:methanol (1:1 v/v) and then dried under a stream of nitrogen to obtain a uniform lipid film. PEI was diluted to a concentration of 45 mg/100 ml using water. pH of the solution was adjusted to ~7.6 using HCl. This PEI stock solution was prepared fresh each time and was equivalent to approximately 50 nmol amine/μl. CMV were diluted into 0.15 M NaCl at a concentration of ~125 μg in 250 μl. PEI was further diluted into 250 μl 0.15 M NaCl so that approximately 4 moles of PEI amine were present per mole of oligonucleotide/chimeric phosphate. PEI solution was added drop-wise to the CMV solution (both at room temperature) and vortexed for 5–10 minutes. The PEI-complex solution was then added to the lipid film and the lipids dispersed as described above. After a uniform milky suspension was formed, it was extruded through a series of polycarbonate membranes (pore sizes 0.8, 0.4, 0.2, 0.1 and 0.05 μm) using a Liposofast® mini-extruder. Extrusion was done 5 to 7 times through each pore size. After preparation lipid vesicles were stored at 4° C. until use. Under these conditions the lipid vesicles were stable for at least one month. For longer and improved stability the final product can be lyophilized.

7.1.5 Lactosylated-PEI/PEI Complexes

PEI (25 kDa) was purchased from Aldrich Chemical (Milwaukee, Wis.). PEI (800 kDa) was purchased from Fluka chemicals (Ronkonkoma, N.Y., USA). Lactosylation of the PEI was carried out by modification of a previously described method for the conjugation of oligosaccharides to proteins. Briefly, 3 to 5 ml of PEI (0.1 to 1.2 $M_{monomer}$) in ammonium acetate (0.2 M) or Tris buffer (0.2 M) (pH 7.6) solution was incubated with 7 to 8 mg of sodium cyanoborohydride (Sigma Chemical Co., St. Louis, Mo.) and approximately 30 mg of lactose monohydrate (Sigma Chemical Co., St. Louis, Mo.). Reaction was carried out in polypropylene tubes, tightly capped in a 37° C. shaking water bath. After 10 days the reaction mixture was dialyzed against distilled water (500 ml) for 48 h with 1 to 2 changes of water. The purified complex was sterile filtered through 0.2 μm filter and stored at 4° C. The amount of sugar (as galactose) associated with PEI was determined by the phenol-sulphuric acid method.

The number of moles of free amine (primary+secondary) in the lactosylated PEI was determined as follows: a standard curve was set up using a 0.02M stock solution of PEI; several aliquots of the stock were diluted to 1 ml using deionized water in glass tubes, then 50 μl of Ninhydrin reagent (Sigma Chemical Co., St. Louis, Mo.) was added to each tube and vortexed vigorously for 10 sec. Color development was allowed to proceed at room temperature for 10 to 12 min. and then O.D. was read (within 4 minutes) at 485 nm on a Beckman DU-64 spectrophotometer. 20 to 50 μl aliquots of the L-PEI samples were treated as above and the number of moles of free amine was determined from the standard curve. Lactosylated-PEI (L-PEI) complexes were prepared as follows: an equivalent of 3 mmol of amine as L-PEI and 3 mmol of amine as PEI, per mmol of RNA/DNA phosphate, were mixed together and diluted in 0.15M NaCl as required; the mixture was added dropwise to a solution of the chimeric and vortexed for 5 min.

To verify complete association of the chimeric oligonucleotides with PEI or L-PEI, gel analysis (4% LMP agarose) of the uncomplexed and complexed chimerics was performed. To determine the degree of protection against nuclease degradation provided by complexation of the chimerics, samples were treated with RNAse and DNAse. After a chloroform phenol extraction, the complexes were dissociated using heparin (50 units/μg nucleic acid) and the products analyzed on a 4% LMP agarose gel.

7.2 Demonstration of PEI/CMV Mediated Alteration of Rat and Human Factor IX

Materials. Fetal bovine serum was obtained from Atlanta Biologicals, Inc. (Atlanta, Ga.). The terminal transferase, fluorescein-12-dUTP, Expand™ high fidelity PCR system, dNTPs and high pure PCR template preparation kit were obtained from Boehringer Mannheim Corp. (Indianapolis, Ind.). Reflection™ NEF-496 autoradiography film and Reflection™ NEF-491 intensifying screens were from DuPont NEN® Research Products (Boston, Mass.). Polyethylenimine (PEI) 800 kDa was obtained from Fluka Chemical Corp. (Ronkonkoma, N.Y.). The [γ-$^{32}$P]ATP was obtained from ICN Biochemicals, Inc. (Costa Mesa, Calif.). pCR™2.1 was obtained from Invitrogen (San Diego, Calif.). OPTIMEM™, Dulbecco's modified Eagle's medium, William's E medium and oligonucleotides 365-A and 365-C were from Life Technologies, Inc. (Gaithersburg, Md.). Spin filters of 30,000 mol wt cutoff were purchased from Millipore Corp. (Bedford, Mass.). DiI and SlowFade™ antifade mounting medium were obtained from Molecular Probes, Inc. (Eugene, Oreg.). T4 polynucleotide kinase was purchased from New England Biolabs, Inc. (Beverly, Mass.). MSI MagnaGraph membrane was purchased from Micron Separations, Inc. (Westboro, Mass.). The primers used for PCR amplification were obtained from Oligos Etc., Inc. (Wilsonville, Oreg.). Tetramethylammonium chloride was purchased from Sigma Chemical Company (St. Louis, Mo.). All other chemicals were molecular biology or reagent grade and purchased from Aldrich Chemical Company (Milwaukee, Wis.), Curtin Matheson Scientific, Inc. (Eden Prairie, Minn.), and Fisher Scientific (Itasca, Ill.).

Oligonucleotide synthesis. Chimeric RNA/DNA oligonucleotides HIXF, RIXF and RIXR were synthesized. The CMV were prepared with DNA and 2'-O-methyl RNA phosphoramidite nucleoside monomers on an ABI 394 synthesizer. The DNA phosphoramidite exocyclic amine groups were protected with benzoyl (adenosine and cytidine) and isobutyryl (guanosine). The protective groups on the 2'-O-methyl RNA phosphoramidites were phenoxyacetyl for adenosine, isobutyryl for cytidine, and dimethylformamide for guanosine. The base protecting groups were removed following synthesis by heating in ethanol/concentrated ammonium hydroxide for 20 h at 55° C. The crude oligonucleotides were electrophoresed on 15% polyacrylamide gels containing 7 M urea, and the DNA visualized using UV shadowing. The chimeric molecules were eluted from the gel slices, concentrated by precipitation and desalted using G-25 spin columns. Greater than 95% of the purified oligonucleotides were full length.

The sequence of the wild type and "mutant" rat Factor IX are

```
(SEQ ID No. 33)              365
wt  AAA GAT TCA TGT GAA GGA GAT AGT GGG GGA CCC CAT GTT
    Lys Asp Ser Cys Glu Gly Asp Ser Gly Gly Pro His Val
(SEQ ID No. 34)

(SEQ ID No. 35)
mt  AAA GAT TCA TGT GAA GGA GAT CGT GGG GGA CCC CAT GTT
                                    Arg
```

The structure of the RIXR, RIXF and HIXR CMV is as follows:
Chimeric Oligonucleotides

```
            RIXR                    (SEQ ID No. 36)
      TGCGCG-ccccaggggGTGCTAgaggaaguguT
    T                                     T
    T                                     T
      TCGCGC GGGGTCCCCCACGATCTCCTTCACAT
          3'5'
```

-continued

```
  RIXR_C                         (SEQ ID No. 37)
TGCGCG-acacuuccucTAGCAccccugqggT
T                                             T
T                                             T
  TCGCGC TGTGAAGGAGATCGTGGGGGACCCCT
       3'5'

RIXF                           (SEQ ID No. 38)
TGCGCG-acacuuccucTAGCAccccugqggT
T                                             T
T                                             T
  TCGCGC TGTGAAGGAGATCGTGGGGGACCCCT
       3'5'

HIXF                           (SEQ ID No. 39)
TGCGCG-acaguuccucTAGCAccccugqggT
T                                             T
T                                             T
  TCGCGC TGTCAAGGAGATCGTGGGGGACCCCT
       3'5'
```

Uppercase letters are deoxyribonucleotides, lower case letters are 2'OMe-ribonucleotides. The nucleotide of the heterologous region is underlined.

Cell Culture, transfections and hepatocyte isolation. HuH-7 cells were maintained in Dulbecco's modified Eagle's medium containing 10% (vol/vol) heat inactivated fetal bovine serum in a humidified $CO_2$ atmosphere at 37° C. Twenty four hours prior to transfection $1 \times 10^5$ cells were plated per 35 mm culture dish. At the time of transfection, the cells were rinsed twice with OPTIMEM™ media and transfections were performed in 1 ml of the same media. Eighteen hours after transfection, 2 ml of Dulbecco's modified Eagle's medium containing 20% (vol/vol) heat inactivated fetal bovine serum was added to each 35 mm dish and the cells maintained for an additional 30 h prior to harvesting for DNA isolation. A PEI (800 kDa) 10 mM stock solution, pH 7.0, was prepared. Briefly, the chimeric oligonucleotides were transfected with 10 mM PEI at 9 equivalents of PEI nitrogen per chimeric phosphate in 100 µl of 0.15 M NaCl at final concentrations of either 150 nM (4 µg), 300 nM (8 µg) and 450 nM (12 µg). After 18 h, an additional 2 ml of medium was added and reduced the chimeric concentrations to 50 nM, 100 nM, and 150 nM, respectively, for the remaining 30 h of culture. HuH-7 vehicle control transfections utilized the same amount of PEI as was used in the HuIXF transfections, but substituted an equal volume of 10 mM Tris-HCl pH 7.6 for the oligonucleotides.

Primary rat hepatocytes were isolated from 250 g male Sprague-Dawley rats (Harlan Sprague-Dawley, Inc., Indianapolis, Ind.) by a two step collagenase perfusion as previously described (Fan et al., Oncogene 12:1909–1919, 1996, which is hereby incorporated by reference) and plated on Primaria™ plates at a density of $4 \times 10^5$ cells per 35 mm dish. The cultures were maintained in William's E medium supplemented with 10% heat inactivated FBS, 26 mM sodium bicarbonate, 23 mM HEPES, 0.01 U/ml insulin, 2 mM L-glutamine, 10 nM dexamethasone, 5.5 mM glucose, 100 U/ml penicillin and 100 U/ml streptomycin. Twenty four hours after plating, the hepatocytes were washed twice with the same medium and 1 ml of fresh medium added and the cells transfected using PEI/chimeric oligonucleotide complexes at the identical concentrations as for the HuH-7 cells. After 18 h, an additional 2 ml of the medium was added and the cells harvested 6 or 30 h later.

Direct injection of chimeric oligonucleotides into liver. Male Sprague-Dawley rats (~175 g) were maintained on a standard 12 h light-dark cycle and fed ad libitum standard laboratory chow. The rats were anesthetized, a midline incision made the liver exposed. A clamp was placed on the hepatic and portal veins as they enter the caudate lobe, and 75 µg of the 1:9 chimeric/PEI complex was injected in a final volume of 250–300 µl directly into the caudate lobe. The lobe remained ligated for 15 min and then blood flow was restored by removing the clamp. After suturing the incision the animals were allowed to recover from the anesthesia and given food and water ad libitum. Vehicle controls were done substituting an equal volume of Tris-HCl pH 7.6 for the chimeric oligonucleotides. Twenty-four and 48 h post-injection the animals were sacrificed, the caudate lobe removed and the tissue around the injection site dissected for DNA isolation. DNA was isolated and the terminal exon of the rat factor IX gene was amplified by PCR.

Nuclear uptake of the chimeric molecules. Chimeric duplexes were 3' end-labeled using terminal transferase and fluorescein-12-dUTP according to the manufacturer's recommendation, and were then mixed with unlabeled oligonucleotides at a 2:3 ratio. Transfections were performed as described above and after 24 h the cells were fixed in phosphate buffered saline, pH 7.4, containing 4% paraformaldehyde (wt/vol) for 10 min at room temperature. Following fixation, the cells were counterstained using a 5 µM solution of DiI in 0.32 M sucrose for 10 min according to the manufacturer's recommendation. After washing with 0.32 M sucrose and then phosphate buffered saline, pH 7.4, the cells were coversliped using SlowFade™ antifade mounting medium in phosphate buffered saline and examined using a MRC1000 confocal microscope (BioRad, Inc., Hercules, Calif.). The caudate lobes of liver in situ were injected with fluorescently-labeled chimerics as described above and harvested 24 h post-injection. The lobes were bisected longitudinally, embedded using OCT and frozen. Cryosections were cut ~10 µm thick, fixed for 10 min at room temperature using phosphate buffered saline, pH 7.4, containing 4% paraformaldehyde (wt/vol). Following fixation, the cells were counterstained using a 5 µM solution of DiI in 0.32 M sucrose for 10 min according to the manufacturer's recommendation. After washing with 0.32 M sucrose and then phosphate buffered saline, pH 7.4, the sections were coversliped using SlowFade™ antifade mounting medium and examined using a MRC1000 confocal microscope (BioRad, Inc.). The collection series for the fixed cells and sectioned tissue were made at 1 µm steps to establish the presence of the chimeric in the nucleus.

DNA isolation and cloning. The cells were harvested by scrapping 24 and 48 h after transfection. Genomic DNA larger than 100–150 base pairs was isolated using the high pure PCR template preparation kit according to the manufacturer's recommendation. PCR amplification of a 317-nt fragment of the eighth exon in the human liver factor IX gene was performed with 500 ng of the isolated DNA. The primers used were 5'-CATTGCTGACAAGGAATACACGAAC-3' (SEQ ID No. 40) and 5'-ATTTGCCTTTCATTGCACACTCTTC-3' (SEQ ID No. 41) corresponding to nucleotides 1008–1032 and 1300–1324, respectively, of the human factor IX cDNA. Primers were annealed at 58° C. for 20 sec, elongation was for 45 sec at 72° C. and denaturation proceeded for 45 sec at 94° C. The sample was amplified for 30 cycles using Expand Hi-fidelity™ polymerase. PCR amplification of a 374-nt fragment of the rat factor IX gene was performed with 500 ng of the isolated DNA from either the primary hepatocytes or liver caudate lobe. The primers used were 5'-ATTGCCTTGCTGGAACTGGATAAC-3' (SEQ ID No. 42) and 5'-TTGCCTTTCATTGCACATTCTTCAC-3' (SEQ ID No. 43) corresponding to nucleotides 433–457 and 782–806, respectively, of the rat factor IX cDNA. Primers were annealed at 59° C. for 20 sec, elongation was for 45 sec at 72° C. and denaturation proceeded for 45 sec at 94° C. The sample was amplified for 30 cycles using Expand Hi-fidelity™ polymerase. The PCR amplification products from both the human and rat factor IX genes were subcloned into the TA cloning vector pCR™2.1 according to the manufacturer's recommendations, and the ligated material used to transform frozen competent *Escherichia coli.*

Colony hybridization and sequencing. Eighteen to 20 h after plating, the colonies were lifted onto MSI MagnaGraph nylon filters, replicated and processed for hybridization according to the manufacturer's recommendation. The filters were hybridized for 24 h with 17 mer oligonucleotide probes 365-A (5'-AAGGAGATAGTGGGGGA-3') (SEQ ID No. 44) or 365-C (5'AAGGAGATCGTGGGGGA-3') (SEQ ID No. 45), where the underlined nucleotide is the target of the mutagenesis. The probes were $^{32}$P-end-labeled using [$\gamma$-$^{32}$] ATP (>7,000 Ci/mmol) and T4 polynucleotide kinase according to the manufacturer's recommendations. Hybridizations were preformed at 37° C. in 2×sodium chloride sodium citrate containing 1% SDS, 5×Denhardt's and 200 μg/ml denatured sonicated fish sperm DNA. After hybridization, the filters were rinsed in 1×sodium chloride phosphate EDTA, 0.5% SDS and then washed at 54° C. for 1 h in 50 mM Tris-HCl, pH 8.0 containing 3 M tetramethylammonium chloride, 2 mM EDTA, pH 8.0, 0.10% SDS. Autoradiography was performed with NEN® Reflection film at −70° C. using an intensifying screen. Plasmid DNA was prepared from colonies identified as hybridizing with 365-A or 365-C using Qiagen minprep kit (Chatsworth, Calif.) and subjected to automatic sequencing using the mp13 reverse primer on an ABI 370A sequencer (Perkin-Elmer, Corp., Foster City, Calif.).

Results In Vivo

Chimeric oligonucleotides were fluorescein-labeled and used to determine whether direct injection into the caudate lobe of the liver was feasible. The results indicated that the hepatocytes adjacent to the injection site within the caudate lobe showed uptake of the fluorescently-labeled chimeric molecules similar to that observed in isolated primary hepatocytes and HuH-7 cells. Although some punctate material was present in the cytoplasm, the labeled material was detected primarily in the nucleus. In fact, only nuclear labeling was observed in hepatocytes farthest from the injection site. The unlabeled PEI/RIXF chimeric complexes and vehicle controls were injected directly into the caudate lobe using the same protocol and the animals sacrificed 24 and 48 h post-injection. Liver DNA was isolated as described in Methods, subjected to PCR amplification of a 374 nt sequence spanning the targeted nt exchange site. Following subcloning and transformation of *Escherichia coli* with the PCR amplified material, duplicate filter lifts of the transformed colonies were performed. The filters were hybridized with $^{32}$-labeled 17-mer oligonucleotides specific for either 365-A (wild-type) or 365-C (factor IX mutation) and processed post-hybridization as described in Methods. Rats which received direct hepatic injection of the RIXF chimeric molecules exhibited a A→C conversion frequency of ~10% at both 24 and 48 h. In contrast, the vehicle controls showed no hybridization with the 365-C probe. Colonies that hybridized with the 365-C probe from the RIXF treated animals were cultured, the plasmid DNA isolated and subjected to sequencing to confirm the A→C conversion. The ends of the amplified 374-nt fragment correspond exactly with the primers and the only nucleotide change observed was an A→C at the targeted exchange site.

7.3 Demonstration of Lactosylated-PEI/CMV Mediated Alteration of Rat Factor IX 7.3.1 Results CMV complexed to a mixture of lactosylated-PEI and PEI was prepared using the RIXR oligonucleotide as described in Section 6.1.5 above. A CMV directed to the complementary strand of the same region of the factor IX was also constructed (RIXR$_C$).

Conversion of the Targeted Nucleotide at Ser$^{365}$ by the Chimeric Oligonucleotides The nuclear localization of the fluorescently-labeled chimeric molecules indicated efficient transfection in the isolated rat hepatocytes. The cultured hepatocytes were then transfected with the unlabeled chimeric molecules factor RIXR$_C$ and RIXR at comparable concentrations using 800 kDa PEI as the carrier. Additionally, vehicle control transfections were performed simultaneously. Forty eight hours after transfection, the cells were harvested and the DNA isolated and processed for hybridization as described in Section 6.1.5. The A→C targeted nucleotide conversion at Ser$^{365}$ was determined by hybridization of duplicate colony lifts of the PCR-amplified and cloned 374-nt stretch of exon 8 of the factor IX gene (Sarkar, B., Koeberl, D. D. & Somer, S. S., "Direct Sequencing of the activation peptide and the catalytic domain of the factor IX gene in six species," *Genomics*, 6, 133–143, 1990.) The 17 mer oligonucleotide probes used to distinguish between the wild-type 365-A (5'-AAGGAGATAGTGGGGGA-3') (SEQ ID No. 46) or converted 365-C (5'-AAGGAGATCGTGGGGGA-3') (SEQ ID No. 47) corresponded to nucleotides 710 through 726 of the cDNA sequence.

The overall frequency of conversion of the targeted nucleotide was calculated by dividing the number of clones hybridizing with the 365-C oligonucleotide by the total number of clones hybridizing with both oligonucleotide probes. The results are summarized in Table III for RIXR$_C$. A→C conversion at Ser$^{365}$ was observed only in primary hepatocytes transfected with the RIXR or RIXR$_C$. Similar conversion frequencies were observed in hepatocytes transfected with RIXR or RIXR$_C$. Neither vehicle transfected cells nor those transfected with other chimeric oligonucleotides yielded any clones hybridizing with the 365-C oligonucleotide probe (unpublished observations). Additionally, no hybridization of the 365-C oligonucleotide probe was observed to clones derived from DNA isolated from untreated hepatocytes and PCR-amplified in the presence of 0.5 to 1.5 μg of the oligonucleotides. The A→C conversion rate in the isolated hepatocytes was also dose dependent using lactosylated PEI derivatives as described in Section 6.1.5 and was as high as 19%. RT-PCR and hybridization analysis of RNA isolated from cultured cells transfected in parallel with lactosylated PEIs demonstrated A→C conversion frequencies ranging from 11.9 to 22.3%.

Site-directed Nucleotide Exchange by Chimeric Oligonucleotides in Intact Liver

The fluorescein-labeled oligonucleotides were also used to determine cellular uptake of the chimeric molecules after direct injection into the caudate lobe of the liver. The results indicated that hepatocytes adjacent to the injection site in the caudate lobe showed uptake of the fluorescently-labeled chimerics similar to that observed in the isolated rat hepatocytes. Although some punctate material was present in the cytoplasm of the hepatocytes, the labeled material was primarily present in the nucleus. In fact, only nuclear labeling was observed in those areas farthest from the injection site. The unlabeled RIXR chimeric oligonucleotides and vehicle controls were then administered in vivo by tail vein injection of the 25 kDa PEI and liver tissue harvested 5 days post-injection. Liver DNA was isolated and subjected to PCR amplification of a 374-nt sequence spanning the targeted nucleotide exchange site, using the same primers as those used with the primary hepatocytes. Following subcloning and transformation of E. coli with the PCR-amplified material, duplicate filter lifts of the transformed colonies were done. The filters were hybridized with the same $^{32}$P-labeled 17-mer oligonucleotides specific for either 365-A (wild-type) or 365-C (mutant) and processed post-hybridization. Rats treated with 100 µg of the RIXR chimeric oligonucleotides exhibited an A→C conversion frequency ranging from 13.9% to 18.9%, while those that received a total of 350 µg in two injections showed 40% conversion. In contrast, the vehicle controls showed no hybridization with the 365-C probe. RT-PCR hybridization of isolated RNA indicated A→C conversion frequencies of 26.4% to 28.4% in the high dose livers. The APTT for vehicle-treated rats ranged from 89.7% to 181.9% of control values (131.84%±32.89%), while the APTT for the oligonucleotide-treated animals ranged from 48.9% to 61.7% (53.8%±4.8%).

The APTT times for a 1/10 dilution of rat test plasma in Hepes buffer (50 mM Hepes/100 mM NaCl/0.02% NaN$_3$ pH 7.4) were determined for both normal (n=9) and the double injected animals (n=3). The factor IX activity of duplicate samples was determined from a log—log standard curve that was constructed from the APTT results for dilution (1:10 to 1:80) of pooled plasma from 12 normal male rats, 6–8 weeks old. The APTT results for the normal rats ranged from 89.7% to 181.9% of the control values (mean= 131.84%±32.89%), while the APTT results for the double injected animals ranged from 49.0% to 61.7% (mean 53.8%±5.8%). The APTT clotting time in seconds for the normal rats ranged from 60.9 seconds to 81.6 seconds (mean=71.3±7.3 seconds) while the APTT times ranged from 92.3 seconds to 98.6 seconds (mean=96.3±2.9 seconds) for the double-infected rats.

Sequence Analysis of the Mutated Factor IX Gene in Isolated Hepatocytes and Intact Liver Direct sequencing of the wild-type and mutated genes was performed to confirm the results from the filter hybridizations in both the in vitro and in vivo studies. At least 10 independent clones hybridizing to either 365-A or 365-C from the intact liver or isolated hepatocytes were analyzed. The results of the sequencing indicated that colonies hybridizing to 365-A exhibited the wild-type IX sequence, i.e. and A at Ser$^{365}$ of the reported cDNA sequence. In contrast, those colonies derived from the factor RIXR$_C$ transfected primary hepatocytes hybridizing to the 365-C oligonucleotide probe converted to a C at Ser$^{365}$. The same A→C conversion at Ser$^{365}$ was observed in the clones derived from the transfected rat liver that hybridized with the 17 mer 365-C oligonucleotide probe. The entire 374-nt PCR amplified region of the factor IX gene was sequenced for all the clones and no alteration other than the indicated changes at Ser$^{365}$ was detected. Finally, the start and end points of the 374-nt PCR amplified genomic DNA derived from both the primary hepatocytes and the intact liver corresponded exactly to those of the primers used for the amplification process, indicating that the cloned and sequenced DNA was derived from genomic DNA rather than nondegraded chimeric oligonucleotides.

TABLE III

Percent A→C conversion at Ser$^{365}$ of rat factor IX genomic DNA by colony lift hybridizations

| PEI Deliver System | | 365-C clones | Total clones | A→C (%) |
|---|---|---|---|---|
| PEI 800 kDa[1] | Concentration | | | |
| In vitro | 150 nM | 24 | 572 | 4.2 |
| | 300 | 31 | 367 | 8.5 |
| | 450 | 63 | 502 | 12.5 |
| Lac-PEI 800 kDa | | | | |
| In vitro | 90 | 18 | 337 | 5.3 |
| | 180 | 34 | 300 | 11.3 |
| | 270 | 47 | 253 | 18.6 |
| Lac-PEI 25 kDa | | | | |
| In vitro | 90 | 28 | 527 | 5.3 |
| | 180 | 53 | 417 | 12.7 |
| | 270 | 60 | 305 | 19.7 |
| Lac-PEI 25 kDa[2] | Dose | | | |
| In vivo x1 | 100 vg | 24 | 166 | 14:5 |
| | | 71 | 386 | 18.4 |
| | | 50 | 360 | 13.9 |
| Lac-PEI 25 kDa | | | | |
| In vivo x2 | 350 vg | 237 | 601 | 39.4 |
| | | 228 | 563 | 40.5 |
| | | 271 | 678 | 40.0 |

[1]The data shown for the primary hepatocyte transfections represents a mean of two experiments.
[2]The in vivo chimeric/PEI complexes were administered in a volume of 300 vl of 5% dextrose by tail vein injection. The results of three animals at each dose are shown individually.

7.3.2 Materials and Methods

In vivo delivery of the chimeric oligonucleotides. Male Sprague-Dawley rats (Harlan Sprague-Dawley, Inc.) (~50 g) were maintained on a standard 12 h light-dark cycle and fed ad libitum standard laboratory chow. Vehicle controls and lactosylated 25 kDa PEI at a ratio of 6 equivalents of PEI nitrogen per chimeric phosphate were administered in 300 µl of 5% dextrose (Abdallah, B. et al., "A powerful nonviral vector for in vivo gene transfer into the adult mammalian brain: polyethylenimine:, Human Gene Therapy, 7, 1947–1954, 1996.). The aliquots were administered by tail vein injection either as a single dose of 100 µg or divided dose of 150 µg and 200 µg on consecutive days. Five days post-injection, liver tissue was removed for DNA and RNA isolation. DNA was isolated as previously described (Kren, B. T., Trembley, J. H. & Steer, C. J., "Alterations in mRNA stability during rat liver regeneration," Am. J. Physiol., 270, G763–G777, 1996) for PCR amplification of exon 8 of the rat factor IX gene. RNA was isolated for RT-PCR amplification of the same region as the genomic DNA using RNAexol and RNAmate (Intermountian Scientific Corp., Kaysville, Utah) according to the manufacturer's protocol.

Factor IX activity assay. Blood samples from vehicle (n=9) and oligonucleotide-treated (n=3) rats were collected 20 days after the second tail vein injection in 0.1 vol. of 0.105 M sodium citrate/citric acid. After centrifugation at 2,500×g and then 15,000×g the resulting plasma was stored at −70° C. The factor IX activity was determined from activated partial thromboplastin time (APTT) assays. Briefly, 50 μl of APTT reagent (DADE, Miami, Fla.), 50 μl of human factor IX-deficient plasma (George King Biomedical, Overland, Kans.), and 50 μl of 1/10 dilution of rat test plasma in Hepes buffer (50 mM Hepes/100 mM NaCl/0.02% NaN$_3$, pH 7.4) were incubated at 37° C. for 3 min in an ST4 coagulometer (American Bioproducts, Parsippany, N.J.). Clotting was initiated by addition of 50 μl of 33 mM CaCl$_2$ in Hepes buffer. Factor IX activity of duplicate samples was determined from a log—log standard curve constructed from the APTT results for dilution (1:10 to 1:80) of pooled plasma from normal male rats (n=12).

DNA/RNA isolation and cloning. The cells were harvested by scrapping 48 h after transfection. Genomic DNA larger than 100–150 base pairs was isolated using the high pure PCR template preparation kit (Boehringer Mannheim, Corp., Indianapolis, Ind.). RNA was isolated using RNAzol™ B (Tel-Test, Inc., Friendswood, Tex.), according to the manufacturer's protocol. PCR amplification of a 374-nt fragment of the rat factor IX gene was performed with 300 ng of the isolated DNA from either the primary hepatocytes or liver tissue. The primers were designed as 5'-ATTGCCTTGCTGGAACTGGATAAAC-3' (SEQ ID No. 48) and 5'TTGCCTTTCATTGCACATTCTTCAC-3' (SEQ ID No. 49) (Oligos Etc., Wilsonville, Oreg.) corresponding to nucleotides 433–457 and 782–806, respectively, of the rat factor IX cDNA. Primers were annealed at 59° C. for 20 sec, elongation was for 45 sec at 72° C. and denaturation proceeded for 45 sec at 94° C. The sample was amplified for 30 cycles using Expand Hi-fidelity™ polymerase (Boehringer Mannheim, Corp.). The PCR amplification products from both the hepatocytes and intact liver factor IX genes were subcloned into the TA cloning vector pCR™2.1 (Invitrogen, San Diego, Calif.), and the ligated material used to transform frozen competent *E. coli*. To rule out PCR artifacts 300 ng of control DNA was incubated with 0.5, 1.0 and 1.5 μg of the oligonucleotide prior to the PCR-amplification reaction. Additionally, 1.0 μg of the chimeric alone was used as the "template" for the PCR amplification.

RT-PCR amplification was done utilizing the Titian one tube RT-PCR system (Boehringer Mannheim, Corp.) According to the manufacturer's protocol using the same primers as those used for the DNA PCR amplification. To rule out DNA contamination, the RNA samples were treated with RQ1 DNase free RNase (Promega Corp., Madison, Wis.) and RT-PCR negative controls of RNased RNA samples were performed in parallel with the RT-PCR reaction. Each of the PCR reactions were ligated into the same TA cloning vector and transformed into frozen competent *E. coli*.

Colony hybridization and sequencing. Eighteen to 20 h after plating, the colonies were lifted onto MSI MagnaGraph nylon filters, replicated and processed for hybridization according to the manufacturer's recommendation. The filters were hybridized for 24 h with 17 mer oligonucleotide probes 365-A (5'AAGGAGAT<u>A</u>GTGGGGGA-3') (SEQ ID No. 50) OR 365-C (5'-AAGGAGAT<u>C</u>GTGGGGGA-3') (SEQ ID No. 51) (Life technologies, Inc., Gaithersburg, Md.), where the underlined nucleotide is the target for mutagenesis. The probes were $^{32}$P-end-labeled using ($\gamma$-$^{32}$P) ATP (>7,000 Ci/mmol) and T4 polynucleotide kinase (New England Biolabs, Inc., Beverly Mass.). Hybridizations were performed at 37° C. in 2×sodium chloride sodium citrate containing 1% SDS, 5×Denhardt's and 200 μg/ml denatured sonicated fish sperm DNA. After hybridization, the filters were rinsed in 1×sodium chloride sodium phosphate EDTA, 0.5% SDS and then washed at 54° C. for 1 h in 50 mM Tris-HCl, pH 8.0 containing 3 M tetramethylammonium chloride, 2 mM EDTA, pH 8.0, 0.1% SDS (Melchior, W. B. & Von Hippel, P. H. "Alteration of the relative stability of dA.dT and dG.dC base pairs in DNA," Proc. Natl. Acad. Sci. USA, 70, 298–302, 1973.). Autoradiography was performed with NEN®Reflection film at −70° C. using an intensifying screen. Plasmid DNA was prepared from colonies identified as hybridizing with 365-A or 365C using Qiagen miniprep kit (Chatsworth, Calif.) and subjected to automatic sequencing using the mp13 forward and reverse primers as well as a gene specific primer, 5'GTTGACCGAGCCACATGCCTTAG-3' (SEQ ID No. 52) corresponding to nucleotides 616 to 638 of the rat factor IX cDNA using an ABI 370A sequencer (Perkin-Elmer, Corp., Foster City, Calif.).

7.4 Examples of CMV Useful for the Reduction of LDL Levels in Humans

A CMV suitable for the modification of Apo B having a sequence comprising the sequence of SEQ ID No: 5 is given below.

```
Apo B 41/UR (mut→WT)              (SEQ ID No. 53)
 u GCGCG gac ccg acc gaa uuc ggu aac ugu au
u                                          u
u                                          u
 u CGCGC CTG GGC TGG CTT AAG CCA TTG ACA Tu
       3'5'
```

A CMV suitable for the modification of Apo B having a sequence comprising the sequence of SEQ ID No: 12 is given below.

```
Apo B 5/U88 (mut→WT)                       (SEQ ID No. 54)
 u GCGCG cug.uuc aaa gug uaC GGA TCC ucu uug acu gac gau
u                                                       u
u                                                       u
 u CGCGC GAC AAG TTT CAC ATG CCT AGG AGA AAC TGA CTG CTu
       3'5'
```

7.5 Correction of a Crigler-Najjar-like Mutation in the Gunn Rat

Mutant rats with hyperbilirubinemia, termed Gunn rats, have a single nucleotide deletion in the gene encoding bilirubin-uridinediphosphoglucuronate glucuronosyltransferase (UGT1A1). Roy Chowdhury, J., et al., 1991, J. Biol. Chem. 266, 18294. Human patients with Crigler-Najjar syndrome type I also have mutations of the UGT1A1 gene, resulting in life-long hyperbilirubinemia and consequent brain damage. Bosma, P. J., et al., 1992, FASEB J. 6, 2859; Jansen, P. L. M., et al., Progress In Liver Diseases, XIII, Boyer, J. L., & Ockner, R. K., editors (W. B. Saunders, Phil. 1995), pp 125–150. The structure of CN3, a CMV designed to correct the Gunn rat mutation is given below.

```
CN3 (mut→WT)                              (SEQ ID No. 55)
  T GCGCG gg gac uua caG GAC CTT TAC uga ctt cua T
  T                                                T
  T                                                T
  T CGCGC CC CTG AAT GTC CTG GAA ATG ACT GCC GAT T
        3'5'
```

Gunn rat primary cultured hepatocytes were treated with 150 nM CN3 according to the above protocol except that the carrier was either the negatively charged glycosylated lipid vesicles of section 6.2.2 or a lactosylated-PEI carrier at a ratio of oligonucleotide phosphate to imine of 1:4. The results were 8.5% conversion with the negatively charged liposome and 3.6% conversion with lactosylated-PEI carrier.

Gunn rats were injected with 1 mg/Kg of CN3 complexed with either 25 kDa Lac-PEI or complexed with negatively charged Gc lipid vesicles (Gc-NLV) as described above. The rate of gene conversion was determined by cloning and hybridization according to the procedure described for factor IX. The results shown below indicate that between about 15% and 25% of the copies of the UGT1A1 gene were converted.

Frequency of Insertion of G at nucleotide 1239 of the UGT-1 Gene (In Gunn Rats)

| Vehicle | Dosage | CG Clones/Total Clones | Frequency (%) |
|---|---|---|---|
| Gc-NLV | 1 mg | 112/815 | 15.4 |
|  |  | 208/761 | 27.3 |
|  |  | 185/974 | 18.9 |
|  |  | 39/273 | 14.6[1] |
|  |  | 78/403 | 19.3[2] |
| 25 kDa PEI (Lactosylated) | 1 mg | 188/838 | 22.4 |
|  |  | 254/1150 | 22.1 |
|  |  | 245/997 | 24.6 |

[1]Initial conversion frequency determined.
[2]Conversion frequency determined 7 days after 70% partial hepatectomy.

A Gunn rat was injected on five successive days with 1 mg/Kg of CN3 complexed with 25 kDa Lac-PEI as above. Twenty five days after the final injection the serum bilirubin had declined from 6.2 mg/dl to 3.5 mg/dl and remained at that level for a further 25 days.

7.6 Correction of a Factor IX Mutation in Dog

The Chapel Hill strain of dogs, which has a $(G \rightarrow A)^{1477}$ mutation that results in hemophilia in the animals, was used to obtain primary cultured hepatocytes. Four CMV to correct this mutation have been synthesized.

```
DIX1 (mut→WT)                             (SEQ ID No. 56)
  T gcgcg auu caa aga aTT GAC CCT AAT AAT cga ccc cT
  T                                                T
  T                                                T
  T CGCGC TAA GTT TCT TAA CTG GGA TTA TTA GCT GGG GT
        3'5'

DIX2 (mut→WT)                             (SEQ ID No. 57)
  T gcgcg caa aga auu gAC CCT AAT aau cga cT
  T                                        T
  T                                        T
  T CGCGC GTT TCT TAA CTG GGA TTA TTA GCT GT
        3'5'

DIX3 (mut→WT)                             (SEQ ID No. 58)
  u gcgcg auu caa aga auu gac ccu aau aau cga ccc cu
  u                                                u
  u                                                u
  u CGCGC TAA GTT TCT TAA CTG GGA TTA TTA GCT GGG Gu
        3'5'

DIX4 (mut→WT)                             (SEQ ID No. 59)
  u gcgcg auu caa aga auu gac ucu aau aau cga ccc cu
  u                                                u
  u                                                u
  u CGCGC TAA GTT TCT TAA CTG GGA TTA TTA GCT GGG Gu
        3'5'
```

DIX1 differs from DIX3 by the replacement of the intervening DNA segment with 2'-O-methyl RNA and replacement of the tetrathymidine linkers with tetrauracil. DIX4 differs from DIX3 in that the mutational vector contains a mismatch in the mutator region. In DIX4 the 5' (lower) strand encodes the desired (wild-type) sequence while the 3' (upper) strand has the sequence of the target, i.e., the mutant sequence.

The hepatocytes were treated with 360 nM DIX1 complexed in either 25 kDa Lac-PEI or galactocerebroside-containing aqueous-cored, negatively charged lipid vesicles (Gc-NLV). The results are given in the table below.

Frequency of conversion of A to G at nucleotide 1477 of the Factor IX Gene
(Primary Hepatocytes from the Chapel Hill Strain of Hemophilia B Dogs)

| Vehicle | Number of Times Transfected | Concentration | G Clones/Total Clones | Frequency (%) |
|---|---|---|---|---|
| Gc-NLV | Once | 360 nM | 30/195 | 15.44 |
|  |  |  | 30/218 | 13.76 |
|  | Twice |  | 30/118 | 25.4 |
| Lac-PEI 25 kDa | Once* | 360 nM | 20/141 | 14.2 |
|  |  |  | 48/348 | 13.3 |
|  | Twice |  | 21/107 | 19.6 |

*RT-PCR on parallel transfected cultures gave an A to G conversion frequency of 11.1%

Each of the DIX2–DIX4 were also tested on primary cultured dog hepatocytes as above. The results showed that DIX2 worked poorly, possibly due to the low (25%) GC percentage. The subsequent experiments the results of DIX3 were about 16% conversion, while a parallel experiments DIX1 gave 10% conversion and the results of DIX4 were about as good as DIX1.

GenBank Sequences References for the Exons of the Human Apolipoprotein B-100 Gene

TABLE II

| Exon No. | cDNA Boundary | GenBank Accession No. Sequence Reference |
|---|---|---|
| 1 | 126 to 207 | M19808 |
| 2 | 208 to 246 | M19808 |
| 3 | 247 to 362 | M19809 |
| 4 | 363 to 508 | M19810 |
| 5 | 509 to 662 | M19811 |
| 6 | 663 to 818 | M19812 |
| 7 | 819 to 943 | M19813 |
| 8 | 944 to 1029 | M19813 |
| 9 | 1030 to 1249 | M19815 |
| 1o | 1250 to 1477 | M19816 |
| 11 | 1478 to 1595 | M19818 |
| 12 | 1596 to 1742 | M19818 |
| 13 | 1743 to 1954 | M19820 |
| 14 | 1955 to 2192 | M19820 |
| 15 | 2193 to 2359 | M19821 |
| 16 | 2360 to 2561 | M19823 |
| 17 | 2562 to 2729 | M19824 |
| 18 | 2730 to 2941 | M19824 |
| 19 | 2942 to 3124 | M19825 |
| 20 | 3125 to 3246 | M19825 |
| 21 | 3247 to 3457 | M19827 |
| 22 | 3458 to 3633 | M19828 |
| 23 | 3634 to 3821 | M19828 |
| 24 | 3822 to 3967 | M19828 |
| 25 | 3968 to 4341 | M19828 |
| 26 | 4342 to 11913 | M19828 |
| 27 | 11944 to 12028 | M19828 |
| 28 | 12029 to 12212 | M19828 |
| 29 | 12213 to 13816 | M19828 |

TABLE I

| SEQ ID. No. | Sequence (5'→3') | G/C# | NA Change | AA Change | AA | % APOB100 | Restriction Site |
|---|---|---|---|---|---|---|---|
| 4 | AGTCTGGATGGGTAAGCCGCCCTCA | 15 | A→T | K→Stop | 1701 | 36.9 | None |
| 5 | CTGGGCTGGCTTAAGCCATTGACAT | 13 | C→A | S→TAA | 1876 | 40.8 | +CTTAAG |
| 6 | GCTCTCTGGGGATAACATACTGGGC | 14 | G→T | E→Stop | 1921 | 41.8 | None |
| 7 | GATGCCGTTGAGTAGCCCCAAGAAT | 13 | A→T | K→Stop | 2047 | 44.5 | None |
| 8 | GAGAGGAATCGATAAACCATTATAG | 10 | C→T | Q→Stop | 2085 | 45.4 | +ATCGAT |
| 9 | TGTAAGAAAATAAAGAGCAGCCCTG | 10 | C→A | Y→Stop | 2110 | 45.9 | None |
| 10 | GCAGCCCTGGGATAACTCCCACAGC | 16 | A→T | K→Stop | 2116 | 46.0 | None |
| 11 | GCAAGCTAATGATTAGCTGAATTCATTCAAT | 8 | T→G | Y→Stop | 2124 | 46.2 | +AGCT |
| 12 | CAAGTTTCACATGCCTAGGAGAAACTGACTG | 11 | A→T | K→Stop | 2138 | 46.5 | +CCTAGG |
| 13 | ATATACAAATTGCATGAGATGATGCCAAAAT | 9 | T→G | L→Stop | 2159 | 47.0 | +CATG |
| 14 | AAACTATCTCAACTGTAGACATATATGATAC | 8 | C→T | Q→Stop | 2174 | 47.3 | -CTGCAG |
| 15 | GCTAATATTATTGATTAAATCATTGAAATTA | 3 | G→T | E→Stop | 2204 | 48.0 | +TTAA |
| 16 | TGATGAGCACTAGCATATCCGTGTA | 11 | T→G | Y→Stop | 2216 | 48.3 | +CTAG |
| 17 | CTGCAGCAGCTTTAGAGACACATAC | 12 | A→T | K→Stop | 2270 | 49.4 | -CTTAAG |
| 18 | AACAGTGAGCTGTAGTGGCCCGTTC | 14 | C→T | Q→Stop | 2684 | 58.6 | None |
| 19 | CAGACTTCCGTTAACCAGAAATCGC | 12 | T→A | L→Stop | 2712 | 59.2 | +GTTAAC |
| 20 | AAAGGGTCATGGTAATGGGCCTGCC | 14 | A→T | K→Stop | 2930 | 64.0 | None |
| 21 | ACATATATGATATAATTTGATCAGT | 5 | C→T | Q→Stop | 2180 | 47.5 | Physiologic |
| 22 | ATGGAGGACGTGTGCGGCCGCCTGG | 18 | C→T | R→C | 112 | Apo E | None |
| 23 | GACCTGCAGAAGTGCCTGGCAGTGT | 15 | C→T | R→C | 158 | Apo E | None |
| 24 | GACCTGCAGAAGCGCCTGGCAGTGT | 16 | T→C | C→R | 159 | Apo E | None |
| 25 | TAAGGTCAGGAGTTTGAGACCAGCC | 13 | A→T | NA | -491 | Apo E | None |

SEQUENCE LISTING (1) GENERAL INFORMATION:

(iii) NUMBER OF SEQUENCES: 62

(2) INFORMATION FOR SEQ ID NO: 1:

(i) SEQUENCE CHARACTERISTICS:
       (A) LENGTH: 4563 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 1:

```
Met Asp Pro Pro Arg Pro Ala Leu Leu Ala Leu Leu Ala Leu Pro Ala
1               5                   10                  15

Leu Leu Leu Leu Leu Ala Gly Ala Arg Ala Glu Glu Met Leu
            20                  25                  30

Glu Asn Val Ser Leu Val Cys Pro Lys Asp Ala Thr Arg Phe Lys His
            35                  40                  45

Leu Arg Lys Tyr Thr Tyr Asn Tyr Glu Ala Glu Ser Ser Ser Gly Val
    50                  55                  60

Pro Gly Thr Ala Asp Ser Arg Ser Ala Thr Arg Ile Asn Cys Lys Val
65                  70                  75                  80

Glu Leu Glu Val Pro Gln Leu Cys Ser Phe Ile Leu Lys Thr Ser Gln
                85                  90                  95

Cys Ile Leu Lys Glu Val Tyr Gly Phe Asn Pro Glu Gly Lys Ala Leu
            100                 105                 110

Leu Lys Lys Thr Lys Asn Ser Glu Glu Phe Ala Ala Met Ser Arg
        115                 120                 125

Tyr Glu Leu Lys Leu Ala Ile Pro Glu Gly Lys Gln Val Phe Leu Tyr
    130                 135                 140

Pro Glu Lys Asp Glu Pro Thr Tyr Ile Leu Asn Ile Lys Arg Gly Ile
145                 150                 155                 160

Ile Ser Ala Leu Leu Val Pro Pro Glu Thr Glu Glu Ala Lys Gln Val
                165                 170                 175

Leu Phe Leu Asp Thr Val Tyr Gly Asn Cys Ser Thr His Phe Thr Val
            180                 185                 190

Lys Thr Arg Lys Gly Asn Val Ala Thr Glu Ile Ser Thr Glu Arg Asp
        195                 200                 205

Leu Gly Gln Cys Asp Arg Phe Lys Pro Ile Arg Thr Gly Ile Ser Pro
    210                 215                 220

Leu Ala Leu Ile Lys Gly Met Thr Arg Pro Leu Ser Thr Leu Ile Ser
225                 230                 235                 240

Ser Ser Gln Ser Cys Gln Tyr Thr Leu Asp Ala Lys Arg Lys His Val
                245                 250                 255

Ala Glu Ala Ile Cys Lys Glu Gln His Leu Phe Leu Pro Phe Ser Tyr
            260                 265                 270

Lys Asn Lys Tyr Gly Met Val Ala Gln Val Thr Gln Thr Leu Lys Leu
        275                 280                 285

Glu Asp Thr Pro Lys Ile Asn Ser Arg Phe Phe Gly Glu Gly Thr Lys
    290                 295                 300

Lys Met Gly Leu Ala Phe Glu Ser Thr Lys Ser Thr Ser Pro Pro Lys
305                 310                 315                 320
```

-continued

Gln Ala Glu Ala Val Leu Lys Thr Val Gln Glu Leu Lys Lys Leu Thr
                325                 330                 335

Ile Ser Glu Gln Asn Ile Gln Arg Ala Asn Leu Phe Asn Lys Leu Val
                340                 345                 350

Thr Glu Leu Arg Gly Leu Ser Asp Glu Ala Val Thr Ser Leu Leu Pro
                355                 360                 365

Gln Leu Ile Glu Val Ser Ser Pro Ile Thr Leu Gln Ala Leu Val Gln
                370                 375                 380

Cys Gly Gln Pro Gln Cys Ser Thr His Ile Leu Gln Trp Leu Lys Arg
385                 390                 395                 400

Val His Ala Asn Pro Leu Leu Ile Asp Val Val Thr Tyr Leu Val Ala
                405                 410                 415

Leu Ile Pro Glu Pro Ser Ala Gln Gln Leu Arg Glu Ile Phe Asn Met
                420                 425                 430

Ala Arg Asp Gln Arg Ser Arg Ala Thr Leu Tyr Ala Leu Ser His Ala
                435                 440                 445

Val Asn Asn Tyr His Lys Thr Asn Pro Thr Gly Thr Gln Glu Leu Leu
                450                 455                 460

Asp Ile Ala Asn Tyr Leu Met Glu Gln Ile Gln Asp Cys Thr Gly
465                 470                 475                 480

Asp Glu Asp Tyr Thr Tyr Leu Ile Leu Arg Val Ile Gly Asn Met Gly
                485                 490                 495

Gln Thr Met Glu Gln Leu Thr Pro Glu Leu Lys Ser Ser Ile Leu Lys
                500                 505                 510

Cys Val Gln Ser Thr Lys Pro Ser Leu Met Ile Gln Lys Ala Ala Ile
                515                 520                 525

Gln Ala Leu Arg Lys Met Glu Pro Lys Asp Lys Asp Gln Glu Val Leu
                530                 535                 540

Leu Gln Thr Phe Leu Asp Asp Ala Ser Pro Gly Asp Lys Arg Leu Ala
545                 550                 555                 560

Ala Tyr Leu Met Leu Met Arg Ser Pro Ser Gln Ala Asp Ile Asn Lys
                565                 570                 575

Ile Val Gln Ile Leu Pro Trp Glu Gln Asn Glu Gln Val Lys Asn Phe
                580                 585                 590

Val Ala Ser His Ile Ala Asn Ile Leu Asn Ser Glu Glu Leu Asp Ile
                595                 600                 605

Gln Asp Leu Lys Lys Leu Val Lys Glu Val Leu Lys Glu Ser Gln Leu
                610                 615                 620

Pro Thr Val Met Asp Phe Arg Lys Phe Ser Arg Asn Tyr Gln Leu Tyr
625                 630                 635                 640

Lys Ser Val Ser Ile Pro Ser Leu Asp Pro Ala Ser Ala Lys Ile Glu
                645                 650                 655

Gly Asn Leu Ile Phe Asp Pro Asn Asn Tyr Leu Pro Lys Glu Ser Met
                660                 665                 670

Leu Lys Thr Thr Leu Thr Ala Phe Gly Phe Ala Ser Ala Asp Leu Ile
                675                 680                 685

Glu Ile Gly Leu Glu Gly Lys Gly Phe Glu Pro Thr Leu Glu Ala Leu
                690                 695                 700

Phe Gly Lys Gln Gly Phe Phe Pro Asp Ser Val Asn Lys Ala Leu Tyr
705                 710                 715                 720

Trp Val Asn Gly Gln Val Pro Asp Gly Val Ser Lys Val Leu Val Asp
                725                 730                 735

```
His Phe Gly Tyr Thr Lys Asp Asp Lys His Glu Gln Asp Met Val Asn
            740                 745                 750

Gly Ile Met Leu Ser Val Glu Lys Leu Ile Lys Asp Leu Lys Ser Lys
            755                 760                 765

Glu Val Pro Glu Ala Arg Ala Tyr Leu Arg Ile Leu Gly Glu Glu Leu
            770                 775                 780

Gly Phe Ala Ser Leu His Asp Leu Gln Leu Leu Gly Lys Leu Leu Leu
785                 790                 795                 800

Met Gly Ala Arg Thr Leu Gln Gly Ile Pro Gln Met Ile Gly Glu Val
                805                 810                 815

Ile Arg Lys Gly Ser Lys Asn Asp Phe Phe Leu His Tyr Ile Phe Met
            820                 825                 830

Glu Asn Ala Phe Glu Leu Pro Thr Gly Ala Gly Leu Gln Leu Gln Ile
            835                 840                 845

Ser Ser Ser Gly Val Ile Ala Pro Gly Ala Lys Ala Gly Val Lys Leu
            850                 855                 860

Glu Val Ala Asn Met Gln Ala Glu Leu Val Ala Lys Pro Ser Val Ser
865                 870                 875                 880

Val Glu Phe Val Thr Asn Met Gly Ile Ile Pro Asp Phe Ala Arg
                885                 890                 895

Ser Gly Val Gln Met Asn Thr Asn Phe Phe His Glu Ser Gly Leu Glu
            900                 905                 910

Ala His Val Ala Leu Lys Pro Gly Lys Leu Lys Phe Ile Ile Pro Ser
            915                 920                 925

Pro Lys Arg Pro Val Lys Leu Leu Ser Gly Gly Asn Thr Leu His Leu
            930                 935                 940

Val Ser Thr Thr Lys Thr Glu Val Ile Pro Pro Leu Ile Glu Asn Arg
945                 950                 955                 960

Gln Ser Trp Ser Val Cys Lys Gln Val Phe Pro Gly Leu Asn Tyr Cys
                965                 970                 975

Thr Ser Gly Ala Tyr Ser Asn Ala Ser Ser Thr Asp Ser Ala Ser Tyr
            980                 985                 990

Tyr Pro Leu Thr Gly Asp Thr Arg Leu Glu Leu Glu Leu Arg Pro Thr
            995                 1000                1005

Gly Glu Ile Glu Gln Tyr Ser Val Ser Ala Thr Tyr Glu Leu Gln Arg
    1010                1015                1020

Glu Asp Arg Ala Leu Val Asp Thr Leu Lys Phe Val Thr Gln Ala Glu
1025                1030                1035                1040

Gly Ala Lys Gln Thr Glu Ala Thr Met Thr Phe Lys Tyr Asn Arg Gln
                1045                1050                1055

Ser Met Thr Leu Ser Ser Glu Val Gln Ile Pro Asp Phe Asp Val Asp
                1060                1065                1070

Leu Gly Thr Ile Leu Arg Val Asn Asp Glu Ser Thr Glu Gly Lys Thr
            1075                1080                1085

Ser Tyr Arg Leu Thr Leu Asp Ile Gln Asn Lys Lys Ile Thr Glu Val
    1090                1095                1100

Ala Leu Met Gly His Leu Ser Cys Asp Thr Lys Glu Glu Arg Lys Ile
1105                1110                1115                1120

Lys Gly Val Ile Ser Ile Pro Arg Leu Gln Ala Glu Ala Arg Ser Glu
                1125                1130                1135

Ile Leu Ala His Trp Ser Pro Ala Lys Leu Leu Leu Gln Met Asp Ser
            1140                1145                1150

Ser Ala Thr Ala Tyr Gly Ser Thr Val Ser Lys Arg Val Ala Trp His
```

-continued

```
                1155                1160                1165
Tyr Asp Glu Lys Ile Glu Phe Glu Trp Asn Thr Gly Thr Asn Val
     1170                1175                1180

Asp Thr Lys Lys Met Thr Ser Asn Phe Pro Val Asp Leu Ser Asp Tyr
1185                1190                1195                1200

Pro Lys Ser Leu His Met Tyr Ala Asn Arg Leu Leu Asp His Arg Val
          1205                1210                1215

Pro Gln Thr Asp Met Thr Phe Arg His Val Gly Ser Lys Leu Ile Val
          1220                1225                1230

Ala Met Ser Ser Trp Leu Gln Lys Ala Ser Gly Ser Leu Pro Tyr Thr
          1235                1240                1245

Gln Thr Leu Gln Asp His Leu Asn Ser Leu Lys Glu Phe Asn Leu Gln
     1250                1255                1260

Asn Met Gly Leu Pro Asp Phe His Ile Pro Glu Asn Leu Phe Leu Lys
1265                1270                1275                1280

Ser Asp Gly Arg Val Lys Tyr Thr Leu Asn Lys Asn Ser Leu Lys Ile
          1285                1290                1295

Glu Ile Pro Leu Pro Phe Gly Gly Lys Ser Arg Asp Leu Lys Met
          1300                1305                1310

Leu Glu Thr Val Arg Thr Pro Ala Leu His Phe Lys Ser Val Gly Phe
     1315                1320                1325

His Leu Pro Ser Arg Glu Phe Gln Val Pro Thr Phe Thr Ile Pro Lys
     1330                1335                1340

Leu Tyr Gln Leu Gln Val Pro Leu Leu Gly Val Leu Asp Leu Ser Thr
1345                1350                1355                1360

Asn Val Tyr Ser Asn Leu Tyr Asn Trp Ser Ala Ser Tyr Ser Gly Gly
          1365                1370                1375

Asn Thr Ser Thr Asp His Phe Ser Leu Arg Ala Arg Tyr His Met Lys
          1380                1385                1390

Ala Asp Ser Val Val Asp Leu Leu Ser Tyr Asn Val Gln Gly Ser Gly
          1395                1400                1405

Glu Thr Thr Tyr Asp His Lys Asn Thr Phe Thr Leu Ser Cys Asp Gly
     1410                1415                1420

Ser Leu Arg His Lys Phe Leu Asp Ser Asn Ile Lys Phe Ser His Val
1425                1430                1435                1440

Glu Lys Leu Gly Asn Asn Pro Val Ser Lys Gly Leu Leu Ile Phe Asp
          1445                1450                1455

Ala Ser Ser Ser Trp Gly Pro Gln Met Ser Ala Ser Val His Leu Asp
          1460                1465                1470

Ser Lys Lys Lys Gln His Leu Phe Val Lys Glu Val Lys Ile Asp Gly
          1475                1480                1485

Gln Phe Arg Val Ser Ser Phe Tyr Ala Lys Gly Thr Tyr Gly Leu Ser
     1490                1495                1500

Cys Gln Arg Asp Pro Asn Thr Gly Arg Leu Asn Gly Glu Ser Asn Leu
1505                1510                1515                1520

Arg Phe Asn Ser Ser Tyr Leu Gln Gly Thr Asn Gln Ile Thr Gly Arg
          1525                1530                1535

Tyr Glu Asp Gly Thr Leu Ser Leu Thr Ser Thr Ser Asp Leu Gln Ser
          1540                1545                1550

Gly Ile Ile Lys Asn Thr Ala Ser Leu Lys Tyr Glu Asn Tyr Glu Leu
          1555                1560                1565

Thr Leu Lys Ser Asp Thr Asn Gly Lys Tyr Lys Asn Phe Ala Thr Ser
1570                1575                1580
```

-continued

```
Asn Lys Met Asp Met Thr Phe Ser Lys Gln Asn Ala Leu Leu Arg Ser
1585                1590                1595                1600

Glu Tyr Gln Ala Asp Tyr Glu Ser Leu Arg Phe Phe Ser Leu Leu Ser
1605                1610                1615

Gly Ser Leu Asn Ser His Gly Leu Glu Leu Asn Ala Asp Ile Leu Gly
            1620                1625                1630

Thr Asp Lys Ile Asn Ser Gly Ala His Lys Ala Thr Leu Arg Ile Gly
1635                1640                1645

Gln Asp Gly Ile Ser Thr Ser Ala Thr Thr Asn Leu Lys Cys Ser Leu
    1650                1655                1660

Leu Val Leu Glu Asn Glu Leu Asn Ala Glu Leu Gly Leu Ser Gly Ala
1665                1670                1675                1680

Ser Met Lys Leu Thr Thr Asn Gly Arg Phe Arg Glu His Asn Ala Lys
            1685                1690                1695

Phe Ser Leu Asp Gly Lys Ala Ala Leu Thr Glu Leu Ser Leu Gly Ser
                1700                1705                1710

Ala Tyr Gln Ala Met Ile Leu Gly Val Asp Ser Lys Asn Ile Phe Asn
    1715                1720                1725

Phe Lys Val Ser Gln Glu Gly Leu Lys Leu Ser Asn Asp Met Met Gly
            1730                1735                1740

Ser Tyr Ala Glu Met Lys Phe Asp His Thr Asn Ser Leu Asn Ile Ala
1745                1750                1755                1760

Gly Leu Ser Leu Asp Phe Ser Ser Lys Leu Asp Asn Ile Tyr Ser Ser
                1765                1770                1775

Asp Lys Phe Tyr Lys Gln Thr Val Asn Leu Gln Leu Gln Pro Tyr Ser
    1780                1785                1790

Leu Val Thr Thr Leu Asn Ser Asp Leu Lys Tyr Asn Ala Leu Asp Leu
            1795                1800                1805

Thr Asn Asn Gly Lys Leu Arg Leu Glu Pro Leu Lys Leu His Val Ala
    1810                1815                1820

Gly Asn Leu Lys Gly Ala Tyr Gln Asn Asn Glu Ile Lys His Ile Tyr
1825                1830                1835                1840

Ala Ile Ser Ser Ala Ala Leu Ser Ala Ser Tyr Lys Ala Asp Thr Val
            1845                1850                1855

Ala Lys Val Gln Gly Val Glu Phe Ser His Arg Leu Asn Thr Asp Ile
            1860                1865                1870

Ala Gly Leu Ala Ser Ala Ile Asp Met Ser Thr Asn Tyr Asn Ser Asp
            1875                1880                1885

Ser Leu His Phe Ser Asn Val Phe Arg Ser Val Met Ala Pro Phe Thr
    1890                1895                1900

Met Thr Ile Asp Ala His Thr Asn Gly Asn Gly Lys Leu Ala Leu Trp
1905                1910                1915                1920

Gly Glu His Thr Gly Gln Leu Tyr Ser Lys Phe Leu Leu Lys Ala Glu
            1925                1930                1935

Pro Leu Ala Phe Thr Phe Ser His Asp Tyr Lys Gly Ser Thr Ser His
            1940                1945                1950

His Leu Val Ser Arg Lys Ser Ile Ser Ala Ala Leu Glu His Lys Val
        1955                1960                1965

Ser Ala Leu Leu Thr Pro Ala Glu Gln Thr Gly Thr Trp Lys Leu Lys
    1970                1975                1980

Thr Gln Phe Asn Asn Asn Glu Tyr Ser Gln Asp Leu Asp Ala Tyr Asn
1985                1990                1995                2000
```

-continued

```
Thr Lys Asp Lys Ile Gly Val Glu Leu Thr Gly Arg Thr Leu Ala Asp
            2005                2010                2015

Leu Thr Leu Leu Asp Ser Pro Ile Lys Val Pro Leu Leu Ser Glu
        2020                2025                2030

Pro Ile Asn Ile Ile Asp Ala Leu Glu Met Arg Asp Ala Val Glu Lys
            2035                2040                2045

Pro Gln Glu Phe Thr Ile Val Ala Phe Val Lys Tyr Asp Lys Asn Gln
    2050                2055                2060

Asp Val His Ser Ile Asn Leu Pro Phe Phe Glu Thr Leu Gln Glu Tyr
2065                2070                2075                2080

Phe Glu Arg Asn Arg Gln Thr Ile Ile Val Leu Glu Asn Val Gln
            2085                2090                2095

Arg Asn Leu Lys His Ile Asn Ile Asp Gln Phe Val Arg Lys Tyr Arg
        2100                2105                2110

Ala Ala Leu Gly Lys Leu Pro Gln Gln Ala Asn Asp Tyr Leu Asn Ser
        2115                2120                2125

Phe Asn Trp Glu Arg Gln Val Ser His Ala Lys Glu Lys Leu Thr Ala
    2130                2135                2140

Leu Thr Lys Lys Tyr Arg Ile Thr Glu Asn Asp Ile Gln Ile Ala Leu
2145                2150                2155                2160

Asp Asp Ala Lys Ile Asn Phe Asn Glu Lys Leu Ser Gln Leu Gln Thr
            2165                2170                2175

Tyr Met Ile Gln Phe Asp Gln Tyr Ile Lys Asp Ser Tyr Asp Leu His
        2180                2185                2190

Asp Leu Lys Ile Ala Ile Ala Asn Ile Asp Glu Ile Ile Glu Lys
        2195                2200                2205

Leu Lys Ser Leu Asp Glu His Tyr His Ile Arg Val Asn Leu Val Lys
    2210                2215                2220

Thr Ile His Asp Leu His Leu Phe Ile Glu Asn Ile Asp Phe Asn Lys
2225                2230                2235                2240

Ser Gly Ser Ser Thr Ala Ser Trp Ile Gln Asn Val Asp Thr Lys Tyr
            2245                2250                2255

Gln Ile Arg Ile Gln Ile Gln Glu Lys Leu Gln Gln Leu Lys Arg His
        2260                2265                2270

Ile Gln Asn Ile Asp Ile Gln His Leu Ala Gly Lys Leu Lys Gln His
    2275                2280                2285

Ile Glu Ala Ile Asp Val Arg Val Leu Leu Asp Gln Leu Gly Thr Thr
    2290                2295                2300

Ile Ser Phe Glu Arg Ile Asn Asp Val Leu Glu His Val Lys His Phe
2305                2310                2315                2320

Val Ile Asn Leu Ile Gly Asp Phe Glu Val Ala Glu Lys Ile Asn Ala
            2325                2330                2335

Phe Arg Ala Lys Val His Glu Leu Ile Glu Arg Tyr Glu Val Asp Gln
        2340                2345                2350

Gln Ile Gln Val Leu Met Asp Lys Leu Val Glu Leu Ala His Gln Tyr
    2355                2360                2365

Lys Leu Lys Glu Thr Ile Gln Lys Leu Ser Asn Val Leu Gln Gln Val
    2370                2375                2380

Lys Ile Lys Asp Tyr Phe Glu Lys Leu Val Gly Phe Ile Asp Asp Ala
2385                2390                2395                2400

Val Lys Lys Leu Asn Glu Leu Ser Phe Lys Thr Phe Ile Glu Asp Val
            2405                2410                2415

Asn Lys Phe Leu Asp Met Leu Ile Lys Lys Leu Lys Ser Phe Asp Tyr
```

```
                  2420              2425              2430
        His Gln Phe Val Asp Glu Thr Asn Asp Lys Ile Arg Glu Val Thr Gln
                      2435              2440              2445

Arg Leu Asn Gly Glu Ile Gln Ala Leu Glu Leu Pro Gln Lys Ala Glu
            2450              2455              2460

Ala Leu Lys Leu Phe Leu Glu Glu Thr Lys Ala Thr Val Ala Val Tyr
        2465              2470              2475              2480

Leu Glu Ser Leu Gln Asp Thr Lys Ile Thr Leu Ile Ile Asn Trp Leu
                      2485              2490              2495

Gln Glu Ala Leu Ser Ser Ala Ser Leu Ala His Met Lys Ala Lys Phe
            2500              2505              2510

Arg Glu Thr Leu Glu Asp Thr Arg Asp Arg Met Tyr Gln Met Asp Ile
            2515              2520              2525

Gln Gln Glu Leu Gln Arg Tyr Leu Ser Leu Val Gly Gln Val Tyr Ser
            2530              2535              2540

Thr Leu Val Thr Tyr Ile Ser Asp Trp Trp Thr Leu Ala Ala Lys Asn
        2545              2550              2555              2560

Leu Thr Asp Phe Ala Glu Gln Tyr Ser Ile Gln Asp Trp Ala Lys Arg
                      2565              2570              2575

Met Lys Ala Leu Val Glu Gln Gly Phe Thr Val Pro Glu Ile Lys Thr
                      2580              2585              2590

Ile Leu Gly Thr Met Pro Ala Phe Glu Val Ser Leu Gln Ala Leu Gln
            2595              2600              2605

Lys Ala Thr Phe Gln Thr Pro Asp Phe Ile Val Pro Leu Thr Asp Leu
            2610              2615              2620

Arg Ile Pro Ser Val Gln Ile Asn Phe Lys Asp Leu Lys Asn Ile Lys
        2625              2630              2635              2640

Ile Pro Ser Arg Phe Ser Thr Pro Glu Phe Thr Ile Leu Asn Thr Phe
                      2645              2650              2655

His Ile Pro Ser Phe Thr Ile Asp Phe Val Glu Met Lys Val Lys Ile
                      2660              2665              2670

Ile Arg Thr Ile Asp Gln Met Leu Asn Ser Glu Leu Gln Trp Pro Val
            2675              2680              2685

Pro Asp Ile Tyr Leu Arg Asp Leu Lys Val Glu Asp Ile Pro Leu Ala
            2690              2695              2700

Arg Ile Thr Leu Pro Asp Phe Arg Leu Pro Glu Ile Ala Ile Pro Glu
        2705              2710              2715              2720

Phe Ile Ile Pro Thr Leu Asn Leu Asn Asp Phe Gln Val Pro Asp Leu
                      2725              2730              2735

His Ile Pro Glu Phe Gln Leu Pro His Ile Ser His Thr Ile Glu Val
                      2740              2745              2750

Pro Thr Phe Gly Lys Leu Tyr Ser Ile Leu Lys Ile Gln Ser Pro Leu
            2755              2760              2765

Phe Thr Leu Asp Ala Asn Ala Asp Ile Gly Asn Gly Thr Thr Ser Ala
            2770              2775              2780

Asn Glu Ala Gly Ile Ala Ala Ser Ile Thr Ala Lys Gly Glu Ser Lys
        2785              2790              2795              2800

Leu Glu Val Leu Asn Phe Asp Phe Gln Ala Asn Ala Gln Leu Ser Asn
                      2805              2810              2815

Pro Lys Ile Asn Pro Leu Ala Leu Lys Glu Ser Val Lys Phe Ser Ser
                      2820              2825              2830

Lys Tyr Leu Arg Thr Glu His Gly Ser Glu Met Leu Phe Phe Gly Asn
            2835              2840              2845
```

-continued

```
Ala Ile Glu Gly Lys Ser Asn Thr Val Ala Ser Leu His Thr Glu Lys
    2850                2855                2860
Asn Thr Leu Glu Leu Ser Asn Gly Val Ile Val Lys Ile Asn Asn Gln
2865                2870                2875                2880
Leu Thr Leu Asp Ser Asn Thr Lys Tyr Phe His Lys Leu Asn Ile Pro
            2885                2890                2895
Lys Leu Asp Phe Ser Ser Gln Ala Asp Leu Arg Asn Glu Ile Lys Thr
            2900                2905                2910
Leu Leu Lys Ala Gly His Ile Ala Trp Thr Ser Ser Gly Lys Gly Ser
            2915                2920                2925
Trp Lys Trp Ala Cys Pro Arg Phe Ser Asp Glu Gly Thr His Glu Ser
    2930                2935                2940
Gln Ile Ser Phe Thr Ile Glu Gly Pro Leu Thr Ser Phe Gly Leu Ser
2945                2950                2955                2960
Asn Lys Ile Asn Ser Lys His Leu Arg Val Asn Gln Asn Leu Val Tyr
            2965                2970                2975
Glu Ser Gly Ser Leu Asn Phe Ser Lys Leu Glu Ile Gln Ser Gln Val
            2980                2985                2990
Asp Ser Gln His Val Gly His Ser Val Leu Thr Ala Lys Gly Met Ala
            2995                3000                3005
Leu Phe Gly Glu Gly Lys Ala Glu Phe Thr Gly Arg His Asp Ala His
    3010                3015                3020
Leu Asn Gly Lys Val Ile Gly Thr Leu Lys Asn Ser Leu Phe Phe Ser
3025                3030                3035                3040
Ala Gln Pro Phe Glu Ile Thr Ala Ser Thr Asn Asn Glu Gly Asn Leu
            3045                3050                3055
Lys Val Arg Phe Pro Leu Arg Leu Thr Gly Lys Ile Asp Phe Leu Asn
            3060                3065                3070
Asn Tyr Ala Leu Phe Leu Ser Pro Ser Ala Gln Gln Ala Ser Trp Gln
            3075                3080                3085
Val Ser Ala Arg Phe Asn Gln Tyr Lys Tyr Asn Gln Asn Phe Ser Ala
    3090                3095                3100
Gly Asn Asn Glu Asn Ile Met Glu Ala His Val Gly Ile Asn Gly Glu
3105                3110                3115                3120
Ala Asn Leu Asp Phe Leu Asn Ile Pro Leu Thr Ile Pro Glu Met Arg
            3125                3130                3135
Leu Pro Tyr Thr Ile Ile Thr Thr Pro Pro Leu Lys Asp Phe Ser Leu
            3140                3145                3150
Trp Glu Lys Thr Gly Leu Lys Glu Phe Leu Lys Thr Thr Lys Gln Ser
            3155                3160                3165
Phe Asp Leu Ser Val Lys Ala Gln Tyr Lys Lys Asn Lys His Arg His
    3170                3175                3180
Ser Ile Thr Asn Pro Leu Ala Val Leu Cys Glu Phe Ile Ser Gln Ser
3185                3190                3195                3200
Ile Lys Ser Phe Asp Arg His Phe Glu Lys Asn Arg Asn Asn Ala Leu
            3205                3210                3215
Asp Phe Val Thr Lys Ser Tyr Asn Glu Thr Lys Ile Lys Phe Asp Lys
            3220                3225                3230
Tyr Lys Ala Glu Lys Ser His Asp Glu Leu Pro Arg Thr Phe Gln Ile
        3235                3240                3245
Pro Gly Tyr Thr Val Pro Val Val Asn Val Glu Val Ser Pro Phe Thr
    3250                3255                3260
```

-continued

```
Ile Glu Met Ser Ala Phe Gly Tyr Val Phe Pro Lys Ala Val Ser Met
3265                3270                3275                3280

Pro Ser Phe Ser Ile Leu Gly Ser Asp Val Arg Val Pro Ser Tyr Thr
            3285                3290                3295

Leu Ile Leu Pro Ser Leu Glu Leu Pro Val Leu His Val Pro Arg Asn
        3300                3305                3310

Leu Lys Leu Ser Leu Pro Asp Phe Lys Glu Leu Cys Thr Ile Ser His
    3315                3320                3325

Ile Phe Ile Pro Ala Met Gly Asn Ile Thr Tyr Asp Phe Ser Phe Lys
3330                3335                3340

Ser Ser Val Ile Thr Leu Asn Thr Asn Ala Glu Leu Phe Asn Gln Ser
3345                3350                3355                3360

Asp Ile Val Ala His Leu Leu Ser Ser Ser Ser Val Ile Asp Ala
            3365                3370                3375

Leu Gln Tyr Lys Leu Glu Gly Thr Thr Arg Leu Thr Arg Lys Arg Gly
        3380                3385                3390

Leu Lys Leu Ala Thr Ala Leu Ser Leu Ser Asn Lys Phe Val Glu Gly
    3395                3400                3405

Ser His Asn Ser Thr Val Ser Leu Thr Thr Lys Asn Met Glu Val Ser
    3410                3415                3420

Val Ala Thr Thr Thr Lys Ala Gln Ile Pro Ile Leu Arg Met Asn Phe
3425                3430                3435                3440

Lys Gln Glu Leu Asn Gly Asn Thr Lys Ser Lys Pro Thr Val Ser Ser
            3445                3450                3455

Ser Met Glu Phe Lys Tyr Asp Phe Asn Ser Ser Met Leu Tyr Ser Thr
            3460                3465                3470

Ala Lys Gly Ala Val Asp His Lys Leu Ser Leu Glu Ser Leu Thr Ser
        3475                3480                3485

Tyr Phe Ser Ile Glu Ser Ser Thr Lys Gly Asp Val Lys Gly Ser Val
    3490                3495                3500

Leu Ser Arg Glu Tyr Ser Gly Thr Ile Ala Ser Glu Ala Asn Thr Tyr
3505                3510                3515                3520

Leu Asn Ser Lys Ser Thr Arg Ser Ser Val Lys Leu Gln Gly Thr Ser
            3525                3530                3535

Lys Ile Asp Asp Ile Trp Asn Leu Glu Val Lys Glu Asn Phe Ala Gly
            3540                3545                3550

Glu Ala Thr Leu Gln Arg Ile Tyr Ser Leu Trp Glu His Ser Thr Lys
        3555                3560                3565

Asn His Leu Gln Leu Glu Gly Leu Phe Phe Thr Asn Gly Glu His Thr
    3570                3575                3580

Ser Lys Ala Thr Leu Glu Leu Ser Pro Trp Gln Met Ser Ala Leu Val
3585                3590                3595                3600

Gln Val His Ala Ser Gln Pro Ser Ser Phe His Asp Phe Pro Asp Leu
            3605                3610                3615

Gly Gln Glu Val Ala Leu Asn Ala Asn Thr Lys Asn Gln Lys Ile Arg
            3620                3625                3630

Trp Lys Asn Glu Val Arg Ile His Ser Gly Ser Phe Gln Ser Gln Val
        3635                3640                3645

Glu Leu Ser Asn Asp Gln Glu Lys Ala His Leu Asp Ile Ala Gly Ser
    3650                3655                3660

Leu Glu Gly His Leu Arg Phe Leu Lys Asn Ile Ile Leu Pro Val Tyr
3665                3670                3675                3680

Asp Lys Ser Leu Trp Asp Phe Leu Lys Leu Asp Val Thr Thr Ser Ile
```

-continued

```
                3685                3690                3695
Gly Arg Arg Gln His Leu Arg Val Ser Thr Ala Phe Val Tyr Thr Lys
                3700                3705                3710
Asn Pro Asn Gly Tyr Ser Phe Ser Ile Pro Val Lys Val Leu Ala Asp
            3715                3720                3725
Lys Phe Ile Ile Pro Gly Leu Lys Leu Asn Asp Leu Asn Ser Val Leu
        3730                3735                3740
Val Met Pro Thr Phe His Val Pro Phe Thr Asp Leu Gln Val Pro Ser
3745                3750                3755                3760
Cys Lys Leu Asp Phe Arg Glu Ile Gln Ile Tyr Lys Lys Leu Arg Thr
                3765                3770                3775
Ser Ser Phe Ala Leu Asn Leu Pro Thr Leu Pro Glu Val Lys Phe Pro
            3780                3785                3790
Glu Val Asp Val Leu Thr Lys Tyr Ser Gln Pro Glu Asp Ser Leu Ile
        3795                3800                3805
Pro Phe Phe Glu Ile Thr Val Pro Glu Ser Gln Leu Thr Val Ser Gln
    3810                3815                3820
Phe Thr Leu Pro Lys Ser Val Ser Asp Gly Ile Ala Ala Leu Asp Leu
3825                3830                3835                3840
Asn Ala Val Ala Asn Lys Ile Ala Asp Phe Glu Leu Pro Thr Ile Ile
                3845                3850                3855
Val Pro Glu Gln Thr Ile Glu Ile Pro Ser Ile Lys Phe Ser Val Pro
            3860                3865                3870
Ala Gly Ile Ala Ile Pro Ser Phe Gln Ala Leu Thr Ala Arg Phe Glu
        3875                3880                3885
Val Asp Ser Pro Val Tyr Asn Ala Thr Trp Ser Ala Ser Leu Lys Asn
    3890                3895                3900
Lys Ala Asp Tyr Val Glu Thr Val Leu Asp Ser Thr Cys Ser Ser Thr
3905                3910                3915                3920
Val Gln Phe Leu Glu Tyr Glu Leu Asn Val Leu Gly Thr His Lys Ile
                3925                3930                3935
Glu Asp Gly Thr Leu Ala Ser Lys Thr Lys Gly Thr Phe Ala His Arg
            3940                3945                3950
Asp Phe Ser Ala Glu Tyr Glu Glu Asp Gly Lys Tyr Glu Gly Leu Gln
        3955                3960                3965
Glu Trp Glu Gly Lys Ala His Leu Asn Ile Lys Ser Pro Ala Phe Thr
    3970                3975                3980
Asp Leu His Leu Arg Tyr Gln Lys Asp Lys Lys Gly Ile Ser Thr Ser
3985                3990                3995                4000
Ala Ala Ser Pro Ala Val Gly Thr Val Gly Met Asp Met Asp Glu Asp
                4005                4010                4015
Asp Asp Phe Ser Lys Trp Asn Phe Tyr Tyr Ser Pro Gln Ser Ser Pro
            4020                4025                4030
Asp Lys Lys Leu Thr Ile Phe Lys Thr Glu Leu Arg Val Arg Glu Ser
        4035                4040                4045
Asp Glu Glu Thr Gln Ile Lys Val Asn Trp Glu Glu Glu Ala Ala Ser
    4050                4055                4060
Gly Leu Leu Thr Ser Leu Lys Asp Asn Val Pro Lys Ala Thr Gly Val
4065                4070                4075                4080
Leu Tyr Asp Tyr Val Asn Lys Tyr His Trp Glu His Thr Gly Leu Thr
                4085                4090                4095
Leu Arg Glu Val Ser Ser Lys Leu Arg Arg Asn Leu Gln Asp His Ala
            4100                4105                4110
```

-continued

```
Glu Trp Val Tyr Gln Gly Ala Ile Arg Glu Ile Asp Asp Ile Asp Glu
    4115                4120                4125

Arg Phe Gln Lys Gly Ala Ser Gly Thr Thr Gly Thr Tyr Gln Glu Trp
    4130                4135                4140

Lys Asp Lys Ala Gln Asn Leu Tyr Gln Glu Leu Leu Thr Gln Glu Gly
4145                4150                4155                4160

Gln Ala Ser Phe Gln Gly Leu Lys Asp Asn Val Phe Asp Gly Leu Val
                4165                4170                4175

Arg Val Thr Gln Glu Phe His Met Lys Val Lys His Leu Ile Asp Ser
                4180                4185                4190

Leu Ile Asp Phe Leu Asn Phe Pro Arg Phe Gln Phe Pro Gly Lys Pro
    4195                4200                4205

Gly Ile Tyr Thr Arg Glu Glu Leu Cys Thr Met Phe Ile Arg Glu Val
    4210                4215                4220

Gly Thr Val Leu Ser Gln Val Tyr Ser Lys Val His Asn Gly Ser Glu
4225                4230                4235                4240

Ile Leu Phe Ser Tyr Phe Gln Asp Leu Val Ile Thr Leu Pro Phe Glu
                4245                4250                4255

Leu Arg Lys His Lys Leu Ile Asp Val Ile Ser Met Tyr Arg Glu Leu
                4260                4265                4270

Leu Lys Asp Leu Ser Lys Glu Ala Gln Glu Val Phe Lys Ala Ile Gln
    4275                4280                4285

Ser Leu Lys Thr Thr Glu Val Leu Arg Asn Leu Gln Asp Leu Leu Gln
    4290                4295                4300

Phe Ile Phe Gln Leu Ile Glu Asp Asn Ile Lys Gln Leu Lys Glu Met
4305                4310                4315                4320

Lys Phe Thr Tyr Leu Ile Asn Tyr Ile Gln Asp Glu Ile Asn Thr Ile
                4325                4330                4335

Phe Asn Asp Tyr Ile Pro Tyr Val Phe Lys Leu Leu Lys Glu Asn Leu
                4340                4345                4350

Cys Leu Asn Leu His Lys Phe Asn Glu Phe Ile Gln Asn Glu Leu Gln
    4355                4360                4365

Glu Ala Ser Gln Glu Leu Gln Gln Ile His Gln Tyr Ile Met Ala Leu
    4370                4375                4380

Arg Glu Glu Tyr Phe Asp Pro Ser Ile Val Gly Trp Thr Val Lys Tyr
4385                4390                4395                4400

Tyr Glu Leu Glu Glu Lys Ile Val Ser Leu Ile Lys Asn Leu Leu Val
                4405                4410                4415

Ala Leu Lys Asp Phe His Ser Glu Tyr Ile Val Ser Ala Ser Asn Phe
                4420                4425                4430

Thr Ser Gln Leu Ser Ser Gln Val Glu Gln Phe Leu His Arg Asn Ile
    4435                4440                4445

Gln Glu Tyr Leu Ser Ile Leu Thr Asp Pro Asp Gly Lys Gly Lys Glu
    4450                4455                4460

Lys Ile Ala Glu Leu Ser Ala Thr Ala Gln Glu Ile Ile Lys Ser Gln
4465                4470                4475                4480

Ala Ile Ala Thr Lys Lys Ile Ile Ser Asp Tyr His Gln Gln Phe Arg
                4485                4490                4495

Tyr Lys Leu Gln Asp Phe Ser Asp Gln Leu Ser Asp Tyr Tyr Glu Lys
                4500                4505                4510

Phe Ile Ala Glu Ser Lys Arg Leu Ile Asp Leu Ser Ile Gln Asn Tyr
    4515                4520                4525
```

```
His Thr Phe Leu Ile Tyr Ile Thr Glu Leu Leu Lys Lys Leu Gln Ser
    4530              4535              4540

Thr Thr Val Met Asn Pro Tyr Met Lys Leu Ala Pro Gly Glu Leu Thr
    4545              4550              4555              4560

Ile Ile Leu
```

(2) INFORMATION FOR SEQ ID NO: 2:

(i) SEQUENCE CHARACTERISTICS:
        (A) LENGTH: 14070 base pairs
        (B) TYPE: nucleic acid
        (C) STRANDEDNESS: single
        (D) TOPOLOGY: linear (xi) SEQUENCE DESCRIPTION: SEQ ID NO: 2:

```
GAGGAGCCCG CCCAGCCAGC CAGGGCCGCG AGGCCGAGGC CAGGCCGCAG CCCAGGAGCC      60

GCCCCACCGC AGCTGGCGAT GGACCCGCCG AGGCCCGCGC TGCTGGCGCT GCTGGCGCTG     120

CCTGCGCTGC TGCTGCTGCT GCTGGCGGGC GCCAGGGCCG AAGAGGAAAT GCTGGAAAAT     180

GTCAGCCTGG TCTGTCCAAA AGATGCGACC CGATTCAAGC ACCTCCGGAA GTACACATAC     240

AACTATGAGG CTGAGAGTTC CAGTGGAGTC CCTGGGACTG CTGATTCAAG AAGTGCCACC     300

AGGATCAACT GCAAGGTTGA GCTGGAGGTT CCCCAGCTCT GCAGCTTCAT CCTGAAGACC     360

AGCCAGTGCA TCCTGAAAGA GGTGTATGGC TTCAACCCTG AGGGCAAAGC CTTGCTGAAG     420

AAAACCAAGA ACTCTGAGGA GTTTGCTGCA GCCATGTCCA GTATGAGCT CAAGCTGGCC     480

ATTCCAGAAG GAAGCAGGT TTTCCTTTAC CCGGAGAAAG ATGAACCTAC TTACATCCTG     540

AACATCAAGA GGGGCATCAT TTCTGCCCTC CTGGTTCCCC AGAGACAGA AGAAGCCAAG     600

CAAGTGTTGT TTCTGGATAC CGTGTATGGA AACTGCTCCA CTCACTTTAC CGTCAAGACG     660

AGGAAGGGCA ATGTGGCAAC AGAAATATCC ACTGAAAGAG ACCTGGGGCA GTGTGATCGC     720

TTCAAGCCCA TCCGCACAGG CATCAGCCCA CTTGCTCTCA TCAAAGGCAT GACCCGCCCC     780

TTGTCAACTC TGATCAGCAG CAGCCAGTCC TGTCAGTACA CACTGGACGC TAAGAGGAAG     840

CATGTGGCAG AAGCCATCTG CAAGGAGCAA CACCTCTTCC TGCCTTTCTC CTACAAGAAT     900

AAGTATGGGA TGGTAGCACA AGTGACACAG ACTTTGAAAC TTGAAGACAC ACCAAAGATC     960

AACAGCCGCT TCTTTGGTGA AGGTACTAAG AAGATGGGCC TCGCATTTGA GAGCACCAAA    1020

TCCACATCAC CTCCAAAGCA GGCCGAAGCT GTTTTGAAGA CTGTCCAGGA ACTGAAAAAA    1080

CTAACCATCT CTGAGCAAAA TATCCAGAGA GCTAATCTCT TCAATAAGCT GGTTACTGAG    1140

CTGAGAGGCC TCAGTGATGA AGCAGTCACA TCTCTCTTGC ACAGCTGAT TGAGGTGTCC    1200

AGCCCCATCA CTTTACAAGC CTTGGTTCAG TGTGGACAGC CTCAGTGCTC CACTCACATC    1260

CTCCAGTGGC TGAAACGTGT GCATGCCAAC CCCCTTCTGA TAGATGTGGT CACCTACCTG    1320

GTGGCCCTGA TCCCCGAGCC CTCAGCACAG CAGCTGCGAG AGATCTTCAA CATGGCGAGG    1380

GATCAGCGCA GCCGAGCCAC CTTGTATGCG CTGAGCCACG CGGTCAACAA CTATCATAAG    1440

ACAAACCCTA CAGGGACCCA GGAGCTGCTG GACATTGCTA ATTACCTGAT GGAACAGATT    1500

CAAGATGACT GCACTGGGGA TGAAGATTAC ACCTATTTGA TTCTGCGGGT CATTGGAAAT    1560

ATGGGCCAAA CCATGGAGCA GTTAACTCCA GAACTCAAGT CTTCAATCCT GAAATGTGTC    1620

CAAAGTACAA AGCCATCACT GATGATCCAG AAAGCTGCCA TCCAGGCTCT GCGGAAAATG    1680

GAGCCTAAAG ACAAGGACCA GGAGGTTCTT CTTCAGACTT TCCTTGATGA TGCTTCTCCG    1740

GGAGATAAGC GACTGGCTGC CTATCTTATG TTGATGAGGA GTCCTTCACA GGCAGATATT    1800
```

```
AACAAAATTG TCCAAATTCT ACCATGGGAA CAGAATGAGC AAGTGAAGAA CTTTGTGGCT      1860

TCCCATATTG CCAATATCTT GAACTCAGAA GAATTGGATA TCCAAGATCT GAAAAAGTTA      1920

GTGAAAGAAG TTCTGAAAGA ATCTCAACTT CCAACTGTCA TGGACTTCAG AAAATTCTCT      1980

CGGAACTATC AACTCTACAA ATCTGTTTCT ATTCCATCAC TTGACCCAGC CTCAGCCAAA      2040

ATAGAAGGGA ATCTTATATT TGATCCAAAT AACTACCTTC CTAAAGAAAG CATGCTGAAA      2100

ACTACCCTCA CTGCCTTTGG ATTTGCTTCA GCTGACCTCA TCGAGATTGG CTTGGAAGGA      2160

AAAGGCTTTG AGCCAACATT GGAAGCTCTT TTTGGGAAGC AAGGATTTTT CCAGACAGTT      2220

GTCAACAAAG CTTTGTACTG GGTTAATGGT CAAGTTCCTG ATGGTGTCTC TAAGGTCTTA      2280

GTGGACCACT TTGGCTATAC CAAAGATGAT AAACATGAGC AGGATATGGT AAATGGAATA      2340

ATGCTCAGTG TTGAGAAGCT GATTAAAGAT TTGAAATCCA AGAAGTCCCC GGAAGCCAGA      2400

GCCTACCTCC GCATCTTGGG AGAGGAGCTT GGTTTTGCCA GTCTCCATGA CCTCCAGCTC      2460

CTGGGAAAGC TGCTTCTGAT GGGTGCCCGC ACTCTGCAGG GGATCCCCCA GATGATTGGA      2520

GAGGTCATCA GGAAGGGCTC AAAGAATGAC TTTTTTCTTC ACTACATCTT CATGGAGAAT      2580

GCCTTTGAAC TCCCCACTGG AGCTGGATTA CAGTTGCAAA TATCTTCATC TGGAGTCATT      2640

GCTCCCGGAG CCAAGGCTGG AGTAAAACTG GAAGTAGCCA ACATGCAGGC TGAACTGGTG      2700

GCAAAACCCT CCGTGTCTGT GGAGTTTGTG ACAAATATGG CATCATCAT TCCGGACTTC      2760

GCTAGGAGTG GGGTCCAGAT GAACACCAAC TTCTTCCACG AGTCGGGTCT GGAGGCTCAT      2820

GTTGCCCTAA AACCTGGGAA GCTGAAGTTT ATCATTCCTT CCCCAAAGAG ACCAGTCAAG      2880

CTGCTCAGTG GAGGCAACAC ATTACATTTG GTCTCTACCA CCAAAACGGA GGTGATCCCA      2940

CCTCTCATTG AGAACAGGCA GTCCTGGTCA GTTTGCAAGC AAGTCTTTCC TGGCCTGAAT      3000

TACTGCACCT CAGGCGCTTA CTCCAACGCC AGCTCCACAG ACTCCGCCTC CTACTATCCG      3060

CTGACCGGGG ACACCAGATT AGAGCTGGAA CTGAGGCCTA CAGGAGAGAT TGAGCAGTAT      3120

TCTGTCAGCG CAACCTATGA GCTCCAGAGA GAGGACAGAG CCTTGGTGGA TACCCTGAAG      3180

TTTGTAACTC AAGCAGAAGG TGCGAAGCAG ACTGAGGCTA CCATGACATT CAAATATAAT      3240

CGGCAGAGTA TGACCTTGTC CAGTGAAGTC CAAATTCCGG ATTTTGATGT TGACCTCGGA      3300

ACAATCCTCA GAGTTAATGA TGAATCTACT GAGGGCAAAA CGTCTTACAG ACTCACCCTG      3360

GACATTCAGA ACAAGAAAAT TACTGAGGTC GCCCTCATGG GCCACCTAAG TTGTGACACA      3420

AAGGAAGAAA GAAAAATCAA GGGTGTTATT TCCATACCCC GTTTGCAAGC AGAAGCCAGA      3480

AGTGAGATCC TCGCCCACTG GTCGCCTGCC AAACTGCTTC TCCAAATGGA CTCATCTGCT      3540

ACAGCTTATG GCTCCACAGT TTCCAAGAGG GTGGCATGGC ATTATGATGA AGAGAAGATT      3600

GAATTTGAAT GGAACACAGG CACCAATGTA GATACCAAAA AAATGACTTC CAATTTCCCT      3660

GTGGATCTCT CCGATTATCC TAAGAGCTTG CATATGTATG CTAATAGACT CCTGGATCAC      3720

AGAGTCCCTC AAACAGACAT GACTTTCCGG CACGTGGGTT CCAAATTAAT AGTTGCAATG      3780

AGCTCATGGC TTCAGAAGGC ATCTGGGAGT CTTCCTTATA CCCAGACTTT GCAAGACCAC      3840

CTCAATAGCC TGAAGGAGTT CAACCTCCAG AACATGGGAT TGCCAGACTT CCACATCCCA      3900

GAAACCTCT TCTTAAAAAG CGATGGCCGG GTCAAATATA CCTTGAACAA GAACAGTTTG      3960

AAAATTGAGA TTCCTTTGCC TTTTGGTGGC AAATCCTCCA GAGATCTAAA GATGTTAGAG      4020

ACTGTTAGGA CACCAGCCCT CCACTTCAAG TCTGTGGGAT CCATCTGCC ATCTCGAGAG      4080

TTCCAAGTCC CTACTTTTAC CATTCCCAAG TTGTATCAAC TGCAAGTGCC TCTCCTGGGT      4140

GTTCTAGACC TCTCCACGAA TGTCTACAGC AACTTGTACA CTGGTCCGC CTCCTACAGT      4200
```

-continued

```
GGTGGCAACA CCAGCACAGA CCATTTCAGC CTTCGGGCTC GTTACCACAT GAAGGCTGAC    4260

TCTGTGGTTG ACCTGCTTTC CTACAATGTG CAAGGATCTG GAGAAACAAC ATATGACCAC    4320

AAGAATACGT TCACACTATC ATGTGATGGG TCTCTACGCC ACAAATTTCT AGATTCGAAT    4380

ATCAAATTCA GTCATGTAGA AAAACTTGGA AACAACCCAG TCTCAAAAGG TTTACTAATA    4440

TTCGATGCAT CTAGTTCCTG GGACCACAG ATGTCTGCTT CAGTTCATTT GGACTCCAAA     4500

AAGAAACAGC ATTTGTTTGT CAAAGAAGTC AAGATTGATG GGCAGTTCAG AGTCTCTTCG    4560

TTCTATGCTA AAGGCACATA TGGCCTGTCT TGTCAGAGGG ATCCTAACAC TGGCCGGCTC    4620

AATGGAGAGT CCAACCTGAG GTTTAACTCC TCCTACCTCC AAGGCACCAA CCAGATAACA    4680

GGAAGATATG AAGATGGAAC CCTCTCCCTC ACCTCCACCT CTGATCTGCA AGTGGCATC    4740

ATTAAAAATA CTGCTTCCCT AAAGTATGAG AACTACGAGC TGACTTTAAA ATCTGACACC    4800

AATGGGAAGT ATAAGAACTT TGCCACTTCT AACAAGATGG ATATGACCTT CTCTAAGCAA    4860

AATGCACTGC TGCGTTCTGA ATATCAGGCT GATTACGAGT CATTGAGGTT CTTCAGCCTG    4920

CTTTCTGGAT CACTAAATTC CCATGGTCTT GAGTTAAATG CTGACATCTT AGGCACTGAC    4980

AAAATTAATA GTGGTGCTCA CAAGGCGACA CTAAGGATTG GCCAAGATGG AATATCTACC    5040

AGTGCAACGA CCAACTTGAA GTGTAGTCTC CTGGTGCTGG AGAATGAGCT GAATGCAGAG    5100

CTTGGCCTCT CTGGGCATC TATGAAATTA ACAACAAATG GCCGCTTCAG GGAACACAAT    5160

GCAAAATTCA GTCTGGATGG GAAAGCCGCC CTCACAGAGC TATCACTGGG AAGTGCTTAT    5220

CAGGCCATGA TTCTGGGTGT CGACAGCAAA AACATTTTCA ACTTCAAGGT CAGTCAAGAA    5280

GGACTTAAGC TCTCAAATGA CATGATGGGC TCATATGCTG AAATGAAATT TGACCACACA    5340

AACAGTCTGA ACATTGCAGG CTTATCACTG GACTTCTCTT CAAAACTTGA CAACATTTAC    5400

AGCTCTGACA AGTTTTATAA GCAAACTGTT AATTTACAGC TACAGCCCTA TTCTCTGGTA    5460

ACTACTTTAA ACAGTGACCT GAAATACAAT GCTCTGGATC TCACCAACAA TGGGAAACTA    5520

CGGCTAGAAC CCCTGAAGCT GCATGTGGCT GGTAACCTAA AAGGAGCCTA CCAAAATAAT    5580

GAAATAAAAC ACATCTATGC CATCTCTTCT GCTGCCTTAT CAGCAAGCTA TAAAGCAGAC    5640

ACTGTTGCTA AGGTTCAGGG TGTGGAGTTT AGCCATCGGC TCAACACAGA CATCGCTGGG    5700

CTGGCTTCAG CCATTGACAT GAGCACAAAC TATAATTCAG ACTCACTGCA TTTCAGCAAT    5760

GTCTTCCGTT CTGTAATGGC CCCGTTTACC ATGACCATCG ATGCACATAC AAATGGCAAT    5820

GGGAAACTCG CTCTCTGGGG AGAACATACT GGGCAGCTGT ATAGCAAATT CCTGTTGAAA    5880

GCAGAACCTC TGGCATTTAC TTTCTCTCAT GATTACAAAG GCTCCACAAG TCATCATCTC    5940

GTGTCTAGGA AAAGCATCAG TGCAGCTCTT GAACACAAAG TCAGTGCCCT GCTTACTCCA    6000

GCTGAGCAGA CAGGCACCTG GAAACTCAAG ACCCAATTTA ACAACAATGA ATACAGCCAG    6060

GACTTGGATG CTTACAACAC TAAAGATAAA ATTGGCGTGG AGCTTACTGG ACGAACTCTG    6120

GCTGACCTAA CTCTACTAGA CTCCCCAATT AAAGTGCCAC TTTTACTCAG TGAGCCCATC    6180

AATATCATTG ATGCTTTAGA GATGAGAGAT GCCGTTGAGA AGCCCAAGA ATTTACAATT    6240

GTTGCTTTTG TAAAGTATGA TAAAAACCAA GATGTTCACT CCATTAACCT CCCATTTTTT    6300

GAGACCTTGC AAGAATATTT TGAGAGGAAT CGACAAACCA TTATAGTTGT ACTGGAAAAC    6360

GTACAGAGAA ACCTGAAGCA CATCAATATT GATCAATTTG TAAGAAAATA CAGAGCAGCC    6420

CTGGGAAAAC TCCCACAGCA AGCTAATGAT TATCTGAATT CATTCAATTG GGAGAGACAA    6480

GTTTCACATG CCAAGGAGAA ACTGACTGCT CTCACAAAAA AGTATAGAAT TACAGAAAAT    6540
```

```
GATATACAAA TTGCATTAGA TGATGCCAAA ATCAACTTTA ATGAAAAACT ATCTCAACTG      6600

CAGACATATA TGATACAATT TGATCAGTAT ATTAAAGATA GTTATGATTT ACATGATTTG      6660

AAAATAGCTA TTGCTAATAT TATTGATGAA ATCATTGAAA AATTAAAAAG TCTTGATGAG      6720

CACTATCATA TCCGTGTAAA TTTAGTAAAA ACAATCCATG ATCTACATTT GTTTATTGAA      6780

AATATTGATT TTAACAAAAG TGGAAGTAGT ACTGCATCCT GGATTCAAAA TGTGGATACT      6840

AAGTACCAAA TCAGAATCCA GATACAAGAA AAACTGCAGC AGCTTAAGAG ACACATACAG      6900

AATATAGACA TCCAGCACCT AGCTGGAAAG TTAAAACAAC ACATTGAGGC TATTGATGTT      6960

AGAGTGCTTT TAGATCAATT GGGAACTACA ATTTCATTTG AAAGAATAAA TGATGTTCTT      7020

GAGCATGTCA AACACTTTGT TATAAATCTT ATTGGGGATT TTGAAGTAGC TGAGAAAATC      7080

AATGCCTTCA GAGCCAAAGT CCATGAGTTA ATCGAGAGGT ATGAAGTAGA CCAACAAATC      7140

CAGGTTTTAA TGGATAAATT AGTAGAGTTG GCCCACCAAT ACAAGTTGAA GGAGACTATT      7200

CAGAAGCTAA GCAATGTCCT ACAACAAGTT AAGATAAAAG ATTACTTTGA GAAATTGGTT      7260

GGATTTATTG ATGATGCTGT CAAGAAGCTT AATGAATTAT CTTTTAAAAC ATTCATTGAA      7320

GATGTTAACA AATTCCTTGA CATGTTGATA AAGAAATTAA AGTCATTTGA TTACCACCAG      7380

TTTGTAGATG AAACCAATGA CAAAATCCGT GAGGTGACTC AGAGACTCAA TGGTGAAATT      7440

CAGGCTCTGG AACTACCACA AAAAGCTGAA GCATTAAAAC TGTTTTTAGA GGAAACCAAG      7500

GCCACAGTTG CAGTGTATCT GGAAAGCCTA CAGGACACCA AAATAACCTT AATCATCAAT      7560

TGGTTACAGG AGGCTTTAAG TTCAGCATCT TTGGCTCACA TGAAGGCCAA ATTCCGAGAG      7620

ACTCTAGAAG ATACACGAGA CCGAATGTAT CAAATGGACA TTCAGCAGGA ACTTCAACGA      7680

TACCTGTCTC TGGTAGGCCA GGTTTATAGC ACACTTGTCA CCTACATTTC TGATTGGTGG      7740

ACTCTTGCTG CTAAGAACCT TACTGACTTT GCAGAGCAAT ATTCTATCCA AGATTGGGCT      7800

AAACGTATGA AAGCATTGGT AGAGCAAGGG TTCACTGTTC CTGAAATCAA GACCATCCTT      7860

GGGACCATGC CTGCCTTTGA AGTCAGTCTT CAGGCTCTTC AGAAAGCTAC CTTCCAGACA      7920

CCTGATTTTA TAGTCCCCCT AACAGATTTG AGGATTCCAT CAGTTCAGAT AAACTTCAAA      7980

GACTTAAAAA ATATAAAAAT CCCATCCAGG TTTTCCACAC CAGAATTTAC CATCCTTAAC      8040

ACCTTCCACA TTCCTTCCTT TACAATTGAC TTTGTAGAAA TGAAAGTAAA GATCATCAGA      8100

ACCATTGACC AGATGCTGAA CAGTGAGCTG CAGTGGCCCG TTCCAGATAT ATATCTCAGG      8160

GATCTGAAGG TGGAGGACAT TCCTCTAGCG AGAATCACCC TGCCAGACTT CCGTTTACCA      8220

GAAATCGCAA TTCCAGAATT CATAATCCCA ACTCTCAACC TTAATGATTT TCAAGTTCCT      8280

GACCTTCACA TACCAGAATT CCAGCTTCCC CACATCTCAC ACACAATTGA AGTACCTACT      8340

TTTGGCAAGC TATACAGTAT TCTGAAAATC CAATCTCCTC TTTTCACATT AGATGCAAAT      8400

GCTGACATAG GGAATGGAAC CACCTCAGCA AACGAAGCAG GTATCGCAGC TTCCATCACT      8460

GCCAAAGGAG AGTCCAAATT AGAAGTTCTC AATTTTGATT TTCAAGCAAA TGCACAACTC      8520

TCAAACCCTA AGATTAATCC GCTGGCTCTG AAGGAGTCAG TGAAGTTCTC CAGCAAGTAC      8580

CTGAGAACGG AGCATGGGAG TGAAATGCTG TTTTTTGGAA ATGCTATTGA GGGAAAATCA      8640

AACACAGTGG CAAGTTTACA CACAGAAAAA AATACACTGG AGCTTAGTAA TGGAGTGATT      8700

GTCAAGATAA ACAATCAGCT TACCCTGGAT AGCAACACTA ATACTTCCA CAAATTGAAC      8760

ATCCCCAAAC TGGACTTCTC TAGTCAGGCT GACCTGCGCA ACGAGATCAA GACACTGTTG      8820

AAAGCTGGCC ACATAGCATG GACTTCTTCT GGAAAAGGGT CATGGAAATG GGCCTGCCCC      8880

AGATTCTCAG ATGAGGGAAC ACATGAATCA CAAATTAGTT TCACCATAGA AGGACCCCTC      8940
```

-continued

```
ACTTCCTTTG GACTGTCCAA TAAGATCAAT AGCAAACACC TAAGAGTAAA CCAAAACTTG      9000
GTTTATGAAT CTGGCTCCCT CAACTTTTCT AAACTTGAAA TTCAATCACA AGTCGATTCC      9060
CAGCATGTGG GCCACAGTGT TCTAACTGCT AAAGGCATGG CACTGTTTGG AGAAGGGAAG      9120
GCAGAGTTTA CTGGGAGGCA TGATGCTCAT TTAAATGGAA AGGTTATTGG AACTTTGAAA      9180
AATTCTCTTT TCTTTTCAGC CCAGCCATTT GAGATCACGG CATCCACAAA CAATGAAGGG      9240
AATTTGAAAG TTCGTTTTCC ATTAAGGTTA ACAGGGAAGA TAGACTTCCT GAATAACTAT      9300
GCACTGTTTC TGAGTCCCAG TGCCCAGCAA GCAAGTTGGC AAGTAAGTGC TAGGTTCAAT      9360
CAGTATAAGT ACAACCAAAA TTTCTCTGCT GGAAACAACG AGAACATTAT GGAGGCCCAT      9420
GTAGGAATAA ATGGAGAAGC AAATCTGGAT TTCTTAAACA TTCCTTTAAC AATTCCTGAA      9480
ATGCGTCTAC CTTACACAAT AATCACAACT CCTCCACTGA AGATTTCTC TCTATGGGAA       9540
AAAACAGGCT TGAAGGAATT CTTGAAAACG ACAAAGCAAT CATTTGATTT AAGTGTAAAA      9600
GCTCAGTATA AGAAAAACAA ACACAGGCAT TCCATCACAA ATCCTTTGGC TGTGCTTTGT      9660
GAGTTTATCA GTCAGAGCAT CAAATCCTTT GACAGGCATT TTGAAAAAAA CAGAAACAAT      9720
GCATTAGATT TTGTCACCAA ATCCTATAAT GAAACAAAAA TTAAGTTTGA TAAGTACAAA      9780
GCTGAAAAAT CTCACGACGA GCTCCCCAGG ACCTTTCAAA TTCCTGGATA CACTGTTCCA      9840
GTTGTCAATG TTGAAGTGTC TCCATTCACC ATAGAGATGT CGGCATTCGG CTATGTGTTC      9900
CCAAAAGCAG TCAGCATGCC TAGTTTCTCC ATCCTAGGTT CTGACGTCCG TGTGCCTTCA      9960
TACACATTAA TCCTGCCATC ATTAGAGCTG CCAGTCCTTC ATGTCCCTAG AAATCTCAAG      10020
CTTTCTCTTC CAGATTTCAA GGAATTGTGT ACCATAAGCC ATATTTTTAT TCCTGCCATG      10080
GGCAATATTA CCTATGATTT CTCCTTTAAA TCAAGTGTCA TCACACTGAA TACCAATGCT      10140
GAACTTTTTA ACCAGTCAGA TATTGTTGCT CATCTCCTTT CTTCATCTTC ATCTGTCATT      10200
GATGCACTGC AGTACAAATT AGAGGGCACC ACAAGATTGA CAAGAAAAAG GGGATTGAAG      10260
TTAGCCACAG CTCTGTCTCT GAGCAACAAA TTTGTGGAGG GTAGTCATAA CAGTACTGTG      10320
AGCTTAACCA CGAAAAATAT GGAAGTGTCA GTGGCAACAA CCACAAAAGC CCAAATTCCA      10380
ATTTTGAGAA TGAATTTCAA GCAAGAACTT AATGGAAATA CCAAGTCAAA ACCTACTGTC      10440
TCTTCCTCCA TGGAATTTAA GTATGATTTC AATTCTTCAA TGCTGTACTC TACCGCTAAA      10500
GGAGCAGTTG ACCACAAGCT TAGCTTGGAA AGCCTCACCT CTTACTTTTC CATTGAGTCA      10560
TCTACCAAAG GAGATGTCAA GGGTTCGGTT CTTTCTCGGG AATATTCAGG AACTATTGCT      10620
AGTGAGGCCA ACACTTACTT GAATTCCAAG AGCACACGGT CTTCAGTGAA GCTGCAGGGC      10680
ACTTCCAAAA TTGATGATAT CTGGAACCTT GAAGTAAAAG AAAATTTTGC TGGAGAAGCC      10740
ACACTCCAAC GCATATATTC CCTCTGGGAG CACAGTACGA AAAACCACTT ACAGCTAGAG      10800
GGCCTCTTTT TCACCAACGG AGAACATACA AGCAAAGCCA CCCTGGAACT CTCTCCATGG      10860
CAAATGTCAG CTCTTGTTCA GGTCCATGCA AGTCAGCCCA GTTCCTTCCA TGATTTCCCT      10920
GACCTTGGCC AGGAAGTGGC CCTGAATGCT AACACTAAGA ACCAGAAGAT CAGATGGAAA      10980
AATGAAGTCC GGATTCATTC TGGGTCTTTC CAGAGCCAGG TCGAGCTTTC CAATGACCAA      11040
GAAAAGGCAC ACCTTGACAT TGCAGGATCC TTAGAAGGAC ACCTAAGGTT CCTCAAAAAT      11100
ATCATCCTAC CAGTCTATGA CAAGAGCTTA TGGGATTTCC TAAAGCTGGA TGTAACCACC      11160
AGCATTGGTA GGAGACAGCA TCTTCGTGTT TCAACTGCCT TTGTGTACAC CAAAAACCCC      11220
AATGGCTATT CATTCTCCAT CCCTGTAAAA GTTTTGGCTG ATAAATTCAT TATTCCTGGG      11280
```

```
CTGAAACTAA ATGATCTAAA TTCAGTTCTT GTCATGCCTA CGTTCCATGT CCCATTTACA    11340

GATCTTCAGG TTCCATCGTG CAAACTTGAC TTCAGAGAAA TACAAATCTA TAAGAAGCTG    11400

AGAACTTCAT CATTTGCCCT CAACCTACCA ACACTCCCCG AGGTAAAATT CCCTGAAGTT    11460

GATGTGTTAA CAAAATATTC TCAACCAGAA GACTCCTTGA TTCCCTTTTT TGAGATAACC    11520

GTGCCTGAAT CTCAGTTAAC TGTGTCCCAG TTCACGCTTC CAAAAAGTGT TTCAGATGGC    11580

ATTGCTGCTT TGGATCTAAA TGCAGTAGCC AACAAGATCG CAGACTTTGA GTTGCCCACC    11640

ATCATCGTGC CTGAGCAGAC CATTGAGATT CCCTCCATTA AGTTCTCTGT ACCTGCTGGA    11700

ATTGCCATTC CTTCCTTTCA AGCACTGACT GCACGCTTTG AGGTAGACTC TCCCGTGTAT    11760

AATGCCACTT GGAGTGCCAG TTTGAAAAAC AAAGCAGATT ATGTTGAAAC AGTCCTGGAT    11820

TCCACATGCA GCTCAACCGT ACAGTTCCTA GAATATGAAC TTAATGTTTT GGGAACACAC    11880

AAAATCGAAG ATGGTACGTT AGCCTCTAAG ACTAAAGGAA CATTTGCACA CCGTGACTTC    11940

AGTGCAGAAT ATGAAGAAGA TGGCAAATAT GAAGGACTTC AGGAATGGGA AGGAAAAGCG    12000

CACCTCAATA TCAAAAGCCC AGCGTTCACC GATCTCCATC TGCGCTACCA GAAAGACAAG    12060

AAAGGCATCT CCACCTCAGC AGCCTCCCCA GCCGTAGGCA CCGTGGGCAT GGATATGGAT    12120

GAAGATGACG ACTTTTCTAA ATGGAACTTC TACTACAGCC CTCAGTCCTC TCCAGATAAA    12180

AAACTCACCA TATTCAAAAC TGAGTTGAGG GTCCGGGAAT CTGATGAGGA AACTCAGATC    12240

AAAGTTAATT GGGAAGAAGA GGCAGCTTCT GGCTTGCTAA CCTCTCTGAA AGACAACGTG    12300

CCCAAGGCCA CAGGGGTCCT TTATGATTAT GTCAACAAGT ACCACTGGGA ACACACAGGG    12360

CTCACCCTGA GAGAAGTGTC TTCAAAGCTG AGAAGAAATC TGCAGGACCA TGCTGAGTGG    12420

GTTTATCAAG GGGCCATTAG GGAAATTGAT GATATCGACG AGAGGTTCCA GAAAGGAGCC    12480

AGTGGGACCA CTGGGACCTA CCAAGAGTGG AAGGACAAGG CCCAGAATCT GTACCAGGAA    12540

CTGTTGACTC AGGAAGGCCA AGCCAGTTTC CAGGACTCA AGGATAACGT GTTTGATGGC    12600

TTGGTACGAG TTACTCAAGA ATTCCATATG AAAGTCAAGC ATCTGATTGA CTCACTCATT    12660

GATTTTCTGA ACTTCCCCAG ATTCCAGTTT CCGGGGAAAC CTGGGATATA CACTAGGGAG    12720

GAACTTTGCA CTATGTTCAT AAGGGAGGTA GGGACGGTAC TGTCCCAGGT ATATTCGAAA    12780

GTCCATAATG GTTCAGAAAT ACTGTTTTCC TATTTCCAAG ACCTAGTGAT TACACTTCCT    12840

TTCGAGTTAA GGAAACATAA ACTAATAGAT GTAATCTCGA TGTATAGGGA ACTGTTGAAA    12900

GATTTATCAA AGAAGCCCA AGAGGTATTT AAAGCCATTC AGTCTCTCAA GACCACAGAG    12960

GTGCTACGTA ATCTTCAGGA CCTTTTACAA TTCATTTTCC AACTAATAGA AGATAACATT    13020

AAACAGCTGA AGAGATGAA ATTTACTTAT CTTATTAATT ATATCCAAGA TGAGATCAAC    13080

ACAATCTTCA ATGATTATAT CCCATATGTT TTTAAATTGT TGAAAGAAAA CCTATGCCTT    13140

AATCTTCATA AGTTCAATGA ATTTATTCAA AACGAGCTTC AGGAAGCTTC TCAAGAGTTA    13200

CAGCAGATCC ATCAATACAT TATGGCCCTT CGTGAAGAAT ATTTTGATCC AAGTATAGTT    13260

GGCTGGACAG TGAAATATTA TGAACTTGAA GAAAAGATAG TCAGTCTGAT CAAGAACCTG    13320

TTAGTTGCTC TTAAGGACTT CCATTCTGAA TATATTGTCA GTGCCTCTAA CTTTACTTCC    13380

CAACTCTCAA GTCAAGTTGA GCAATTTCTG CACAGAAATA TTCAGGAATA TCTTAGCATC    13440

CTTACCGATC CAGATGGAAA AGGGAAAGAG AAGATTGCAG AGCTTTCTGC CACTGCTCAG    13500

GAAATAATTA AAAGCCAGGC CATTGCGACG AAGAAAATAA TTTCTGATTA CCACCAGCAG    13560

TTTAGATATA AACTGCAAGA TTTTTCAGAC CAACTCTCTG ATTACTATGA AAAATTTATT    13620

GCTGAATCCA AAAGATTGAT TGACCTGTCC ATTCAAAACT ACCACACATT TCTGATATAC    13680
```

-continued

| | |
|---|---|
| ATCACGGAGT TACTGAAAAA GCTGCAATCA ACCACAGTCA TGAACCCCTA CATGAAGCTT | 13740 |
| GCTCCAGGAG AACTTACTAT CATCCTCTAA TTTTTTAAAA GAAATCTTCA TTTATTCTTC | 13800 |
| TTTTCCAATT GAACTTTCAC ATAGCACAGA AAAAATTCAA AATGCCTATA TTGATCAAAC | 13860 |
| CATACAGTGA GCCAGCCTTG CAGTAGGCAG TAGACTATAA GCAGAAGCAC ATATGAACTG | 13920 |
| GACCTGCACC AAAGCTGGCA CCAGGGCTCG GAAGGTCTCT GAACTCAGAA GGATGGCATT | 13980 |
| TTTTGCAAGT TAAAGAAAAT CAGGATCTGA GTTATTTTGC TAAACTTGGG GGAGGAGGAA | 14040 |
| CAAATAAATG GAGTCTTTAT TGTGTATCAT | 14070 |

(2) INFORMATION FOR SEQ ID NO: 3:

(i) SEQUENCE CHARACTERISTICS:
        (A) LENGTH: 3805 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: exon
        (B) LOCATION: 71...114
        (D) OTHER INFORMATION: Exon 1

(xi) SEQUENCE DESCRIPTION: SEQ ID NO: 3:

| | |
|---|---|
| CCTATCCCTG GGGGAGGGGG CGGGACAGGG GGAGCCCTAT AATTGGACAA GTCTGGGATC | 60 |
| CTTGAGTCCT ACTCAGCCCC AGCGGAGGTG AAGGACGTCC TTCCCCAGGA GCCGGTGAGA | 120 |
| AGCGCAGTCG GGGCACGGG GATGAGCTCA GGGGCCTCTA GAAAGAGCTG GGACCCTGGG | 180 |
| AAGCCCTGGC CTCCAGGTAG TCTCAGGAGA GCTACTCGGG GTCGGGCTTG GGGAGAGGAG | 240 |
| GAGCGGGGGT GAGGCAAGCA GCAGGGGACT GGACCTGGGA AGGGCTGGGC AGCAGAGACG | 300 |
| ACCCGACCCG CTAGAAGGTG GGGTGGGGAG AGCAGCTGGA CTGGGATGTA AGCCATAGCA | 360 |
| GGACTCCACG AGTTGTCACT ATCATTATCG AGCACCTACT GGGTGTCCCC AGTGTCCTCA | 420 |
| GATCTCCATA ACTGGGGAGC CAGGGGCAGC GACACGGTAG CTAGCCGTCG ATTGGAGAAC | 480 |
| TTTAAAATGA GGACTGAATT AGCTCATAAA TGGAACACGG CGCTTAACTG TGAGGTTGGA | 540 |
| GCTTAGAATG TGAAGGGAGA ATGAGGAATG CGAGACTGGG ACTGAGATGG AACCGGCGGT | 600 |
| GGGGAGGGGG TGGGGGATG GAATTTGAAC CCCGGGAGAG GAAGATGGAA TTTTCTATGG | 660 |
| AGGCCGACCT GGGGATGGGG AGATAAGAGA AGACCAGGAG GGAGTTAAAT AGGGAATGGG | 720 |
| TTGGGGCGG CTTGGTAAAT GTGCTGGGAT TAGGCTGTTG CAGATAATGC AACAAGGCTT | 780 |
| GGAAGGCTAA CCTGGGGTGA GGCCGGGTTG GGGGCGCTGG GGGTGGGAGG AGTCCTCACT | 840 |
| GGCGGTTGAT TGACAGTTTC TCCTTCCCCA GACTGGCCAA TCACAGGCAG GAAGATGAAG | 900 |
| GTTCTGTGGG CTGCGTTGCT GGTCACATTC CTGGCAGGTA TGGGGCGGG GCTTGCTCGG | 960 |
| TTCCCCCCGC TCCTCCCCCT CTCATCCTCA CCTCAACCTC CTGGCCCCAT TCAGACAGAC | 1020 |
| CCTGGGCCCC CTCTTCTGAG GCTTCTGTGC TGCTTCCTGG CTCTGAACAG CGATTTGACG | 1080 |
| CTCTCTGGGC CTCGGTTTCC CCCATCCTTG AGATAGGAGT TAGAAGTTGT TTTGTTGTTG | 1140 |
| TTGTTTGTTG TTGTTGTTTT GTTTTTTTGA GATGAAGTCT CGCTCTGTCG CCCAGGCTGG | 1200 |
| AGTGCAGTGG CGGGATCTCG GCTCACTGCA AGCTCCGCCT CCCAGGTCCA CGCCATTCTC | 1260 |
| CTGCCTCAGC CTCCCAAGTA GCTGGGACTA CAGGCACATG CCACCACACC CGACTAACTT | 1320 |
| TTTTGTATTT TCAGTAGAGA CGGGGTTTCA CCATGTTGGC CAGGCTGGTC TGGAACTCCT | 1380 |

```
GACCTCAGGT GATCTGCCCG TTTCGATCTC CCAAAGTGCT GGGATTACAG GCGTGAGCCA    1440

CCGCACCTGG CTGGGAGTTA GAGGTTTCTA ATGCATTGCA GGCAGATAGT GAATACCAGA    1500

CACGGGGCAG CTGTGATCTT TATTCTCCAT CACCCCCACA CAGCCCTGCC TGGGGCACAC    1560

AAGGACACTC AATACATGCT TTTCCGCTGG GCCGGTGGCT CACCCCTGTA ATCCCAGCAC    1620

TTTGGGAGGC CAAGGTGGGA GGATCACTTG AGCCCAGGAG TTCAACACCA GCCTGGGCAA    1680

CATAGTGAGA CCCTGTCTCT ACTAAAAATA CAAAAATTAG CCAGGCATGG TGCCACACAC    1740

CTGTGCTCTC AGCTACTCAG GAGGCTGAGG CAGGAGGATC GCTTGAGCCC AGAAGGTCAA    1800

GGTTGCAGTG AACCATGTTC AGGCCGCTGC ACTCCAGCCT GGGTGACAGA GCAAGACCCT    1860

GTTTATAAAT ACATAATGCT TTCCAAGTGA TTAAACCGAC TCCCCCCTCA CCCTGCCCAC    1920

CATGGCTCCA AGAAGCATT TGTGGAGCAC CTTCTGTGTG CCCCTAGGTA GCTAGATGCC    1980

TGGACGGGGT CAGAAGGACC CTGACCCGAC CTTGAACTTG TTCCACACAG GATGCCAGGC    2040

CAAGGTGGAG CAAGCGGTGG AGACAGAGCC GGAGCCCGAG CTGCGCCAGC AGACCGAGTG    2100

GCAGAGCGGC CAGCGCTGGG AACTGGCACT GGGTCGCTTT TGGGATTACC TGCGCTGGGT    2160

GCAGACACTG TCTGAGCAGG TGCAGGAGGA GCTGCTCAGC TCCCAGGTCA CCCAGGAACT    2220

GAGGTGAGTG TCCCCATCCT GGCCCTTGAC CCTCCTGGTG GGCGGCTATA CCTCCCCAGG    2280

TCCAGGTTTC ATTCTGCCCC TGTCGCTAAG TCTTGGGGGG CCTGGGTCTC TGCTGGTTCT    2340

AGCTTCCTCT TCCCATTTCT GACTCCTGGC TTTAGCTCTC TGGAATTCTC TCTCTCAGCT    2400

TTGTCTCTCT CTCTTCCCTT CTGACTCAGT CTCTCACACT CGTCCTGGCT CTGTCTCTGT    2460

CCTTCCCTAG CTCTTTTATA TAGAGACAGA GAGATGGGGT CTCACTGTGT TGCCCAGGCT    2520

GGTCTTGAAC TTCTGGGCTC AAGCGATCCT CCCGCCTCGG CCTCCCAAAG TGCTGGGATT    2580

AGAGGCATGA GCACCTTGCC CGGCCTCCTA GCTCCTTCTT CGTCTCTGCC TCTGCCCTCT    2640

GCATCTGCTC TCTGCATCTG TCTCTGTCTC CTTCTCTCGG CCTCTGCCCC GTTCCTTCTC    2700

TCCCTCTTGG GTCTCTCTGG CTCATCCCCA TCTCGCCCGC CCCATCCCAG CCCTTCTCCC    2760

CCGCCTCCCC ACTGTGCGAC ACCCTCCCGC CCTCTCGGCC GCAGGGCGCT GATGGACGAG    2820

ACCATGAAGG AGTTGAAGGC CTACAAATCG GAACTGGAGG AACAACTGAC CCCGGTGGCG    2880

GAGGAGACGC GGGCACGGCT GTCCAAGGAG CTGCAGGCGG CGCAGGCCCG GCTGGGCGCG    2940

GACATGGAGG ACGTGTGCGG CCGCCTGGTG CAGTACCGCG GCGAGGTGCA GGCCATGCTC    3000

GGCCAGAGCA CCGAGGAGCT GCGGGTGCGC CTCGCCTCCC ACCTGCGCAA GCTGCGTAAG    3060

CGGCTCCTCC GCGATGCCGA TGACCTGCAG AAGCGCCTGG CAGTGTACCA GGCCGGGGCC    3120

CGCGAGGGCG CCGAGCGCGG CCTCAGCGCC ATCCGCGAGC GCCTGGGGCC CCTGGTGGAA    3180

CAGGGCCGCG TGCGGGCCGC CACTGTGGGC TCCCTGGCCG GCCAGCCGCT ACAGGAGCGG    3240

GCCCAGGCCT GGGGCGAGCG GCTGCGCGCG CGGATGGAGG AGATGGGCAG CCGGACCCGC    3300

GACCGCCTGG ACGAGGTGAA GGAGCAGGTG CGGGAGGTGC GCGCCAAGCT GGAGGAGCAG    3360

GCCCAGCAGA TACGCCTGCA GGCCGAGGCC TTCCAGGCCC GCCTCAAGAG CTGGTTCGAG    3420

CCCCTGGTGG AAGACATGCA GCGCCAGTGG GCCGGGCTGG TGGAGAAGGT GCAGGCTGCC    3480

GTGGGCACCA GCGCCGCCCC TGTGCCCAGC GACAATCACT GAACGCCGAA GCCTGCAGCC    3540

ATGCGACCCC ACGCCACCCC GTGCCTCCTG CCTCCGCGCA GCCTGCAGCG GGAGACCCTG    3600

TCCCCGCCCC AGCCGTCCTC CTGGGGTGGA CCCTAGTTTA ATAAAGATTC ACCAAGTTTC    3660

ACGCATCTGC TGGCCTCCCC CTGTGATTTC CTCTAAGCCC CAGCCTCAGT TTCTCTTTCT    3720

GCCCACATAC TGCCACACAA TTCTCAGCCC CCTCCTCTCC ATCTGTGTCT GTGTGTATCT    3780
```

```
TTCTCTCTGC CCTTTTTTTT TTTTT                                              3805

(2) INFORMATION FOR SEQ ID NO: 4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 4:

AGTCTGGATG GGTAAGCCGC CCTCA                                                25

(2) INFORMATION FOR SEQ ID NO: 5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 5:

CTGGGCTGGC TTAAGCCATT GACAT                                                25

(2) INFORMATION FOR SEQ ID NO: 6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 6:

GCTCTCTGGG GATAACATAC TGGGC                                                25

(2) INFORMATION FOR SEQ ID NO: 7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 7:

GATGCCGTTG AGTAGCCCCA AGAAT                                                25

(2) INFORMATION FOR SEQ ID NO: 8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 8:

GAGAGGAATC GATAAACCAT TATAG                                                25
```

(2) INFORMATION FOR SEQ ID NO: 9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 9:

TGTAAGAAAA TAAAGAGCAG CCCTG                              25

(2) INFORMATION FOR SEQ ID NO: 10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 10:

GCAGCCCTGG GATAACTCCC ACAGC                              25

(2) INFORMATION FOR SEQ ID NO: 11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 11:

GCAAGCTAAT GATTAGCTGA ATTCATTCAA T                        31

(2) INFORMATION FOR SEQ ID NO: 12:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 12:

CAAGTTTCAC ATGCCTAGGA GAAACTGACT G                        31

(2) INFORMATION FOR SEQ ID NO: 13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 13:

ATATACAAAT TGCATGAGAT GATGCCAAAA T                        31

(2) INFORMATION FOR SEQ ID NO: 14:

(i) SEQUENCE CHARACTERISTICS:
        (A) LENGTH: 31 base pairs (B) TYPE: nucleic acid
          (C) STRANDEDNESS: single
          (D) TOPOLOGY: linear (ii) MOLECULE TYPE: Other (xi) SEQUENCE DESCRIPTION: SEQ ID NO: 14:

AAACTATCTC AACTGTAGAC ATATATGATA C                                               31

(2) INFORMATION FOR SEQ ID NO: 15:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (ii) MOLECULE TYPE: Other (xi) SEQUENCE DESCRIPTION: SEQ ID NO: 15:

GCTAATATTA TTGATTAAAT CATTGAAATT A                                               31

(2) INFORMATION FOR SEQ ID NO: 16:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: Other (xi) SEQUENCE DESCRIPTION: SEQ ID NO: 16:

TGATGAGCAC TAGCATATCC GTGTA                                                      25

(2) INFORMATION FOR SEQ ID NO: 17:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: Other (xi) SEQUENCE DESCRIPTION: SEQ ID NO: 17:

CTGCAGCAGC TTTAGAGACA CATAC                                                      25

(2) INFORMATION FOR SEQ ID NO: 18:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: Other (xi) SEQUENCE DESCRIPTION: SEQ ID NO: 18:

AACAGTGAGC TGTAGTGGCC CGTTC                                                      25

(2) INFORMATION FOR SEQ ID NO: 19:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: Other (xi) SEQUENCE DESCRIPTION: SEQ ID NO: 19:

CAGACTTCCG TTAACCAGAA ATCGC                                              25

(2) INFORMATION FOR SEQ ID NO: 20:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: Other (xi) SEQUENCE DESCRIPTION: SEQ ID NO: 20:

AAAGGGTCAT GGTAATGGGC CTGCC                                              25

(2) INFORMATION FOR SEQ ID NO: 21:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: Other (xi) SEQUENCE DESCRIPTION: SEQ ID NO: 21:

ACATATATGA TATAATTTGA TCAGT                                              25

(2) INFORMATION FOR SEQ ID NO: 22:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: Other (xi) SEQUENCE DESCRIPTION: SEQ ID NO: 22:

ATGGAGGACG TGTGCGGCCG CCTGG                                              25

(2) INFORMATION FOR SEQ ID NO: 23:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: Other (xi) SEQUENCE DESCRIPTION: SEQ ID NO: 23:

GACCTGCAGA AGTGCCTGGC AGTGT                                              25

(2) INFORMATION FOR SEQ ID NO: 24:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: Other (xi) SEQUENCE DESCRIPTION: SEQ ID NO: 24:

GACCTGCAGA AGCGCCTGGC AGTGT                                              25

(2) INFORMATION FOR SEQ ID NO: 25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 25:

TAAGGTCAGG AGTTTGAGAC CAGCC                                              25

(2) INFORMATION FOR SEQ ID NO: 26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 26:

AGUCUGGAUG GGTAAGCCGC CCUCA                                              25

(2) INFORMATION FOR SEQ ID NO: 27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 27:

CTCGGAGAGC CCCCTCGCA                                                     19

(2) INFORMATION FOR SEQ ID NO: 28:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 28:

CAAGGAGATA GTGGGGAC                                                      19

(2) INFORMATION FOR SEQ ID NO: 29:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 29:

ACCATCGACG AGAAAGGGA                                                     19

(2) INFORMATION FOR SEQ ID NO: 30:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: Other (xi) SEQUENCE DESCRIPTION: SEQ ID NO: 30:

TTTGGACAGC GTCCATACT                                                19

(2) INFORMATION FOR SEQ ID NO: 31:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 31:

TGCCTCGCCC AGGTCCTGG                                                19

(2) INFORMATION FOR SEQ ID NO: 32:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 32:

CCCACTGCCA GGTATGGGC                                                19

(2) INFORMATION FOR SEQ ID NO: 33:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 33:

AAAGATTCAT GTGAAGGAGA TAGTGGGGGA CCCCATGTT                           39

(2) INFORMATION FOR SEQ ID NO: 34:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

Lys Asp Ser Cys Glu Gly Asp Ser Gly Gly Pro His Val
 1               5                  10

(2) INFORMATION FOR SEQ ID NO: 35:

(i) SEQUENCE CHARACTERISTICS:
        (A) LENGTH: 39 base pairs (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 35:

AAAGATTCAT GTGAAGGAGA TCGTGGGGGA CCCCATGTT                    39

(2) INFORMATION FOR SEQ ID NO: 36:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 36:

GGGGTCCCCC ACGATCTCCT TCACATTTTU GUGAAGGAGA TCGTGGGGGA CCCCGCGCGT    60

TTTCGCGC                                                             68

(2) INFORMATION FOR SEQ ID NO: 37:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 37:

TGTGAAGGAG ATCGTGGGGG ACCCCTTTTG GGGUCCCCCA CGATCUCCUU CACAGCGCGT    60

TTTCGCGC                                                             68

(2) INFORMATION FOR SEQ ID NO: 38:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 38:

TGTGAAGGAG ATCGTGGGGG ACCCCTTTTG GGGUCCCCCA CGATCUCCUU CACAGCGCGT    60

TTTCGCGC                                                             68

(2) INFORMATION FOR SEQ ID NO: 39:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 39:

TGTCAAGGAG ATCGTGGGGG ACCCCTTTTG GGGUCCCCCA CGATCUCCUU GACAGCGCGT    60

TTTCGCGC                                                             68

(2) INFORMATION FOR SEQ ID NO: 40:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 40:

CATTGCTGAC AAGGAATACA CGAAC                                  25

(2) INFORMATION FOR SEQ ID NO: 41:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 41:

ATTTGCCTTT CATTGCACAC TCTTC                                  25

(2) INFORMATION FOR SEQ ID NO: 42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 42:

ATTGCCTTGC TGGAACTGGA TAAC                                   24

(2) INFORMATION FOR SEQ ID NO: 43:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 43:

TTGCCTTTCA TTGCACATTC TTCAC                                  25

(2) INFORMATION FOR SEQ ID NO: 44:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 44:

AAGGAGATAG TGGGGGA                                              17

(2) INFORMATION FOR SEQ ID NO: 45:

(i) SEQUENCE CHARACTERISTICS:
        (A) LENGTH: 17 base pairs (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 45:

AAGGAGATCG TGGGGGA                                                    17

(2) INFORMATION FOR SEQ ID NO: 46:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 46:

AAGGAGATAG TGGGGGA                                                    17

(2) INFORMATION FOR SEQ ID NO: 47:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 47:

AAGGAGATCG TGGGGGA                                                    17

(2) INFORMATION FOR SEQ ID NO: 48:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 48:

ATTGCCTTGC TGGAACTGGA TAAAC                                           25

(2) INFORMATION FOR SEQ ID NO: 49:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 49:

TTGCCTTTCA TTGCACATTC TTCAC                                           25

(2) INFORMATION FOR SEQ ID NO: 50:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 50:

AAGGAGATAG TGGGGGA                                                      17

(2) INFORMATION FOR SEQ ID NO: 51:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO: 51:

AAGGAGATCG TGGGGGA                                                      17

(2) INFORMATION FOR SEQ ID NO: 52:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO: 52:

GTTGACCGAG CCACATGCCT TAG                                               23

(2) INFORMATION FOR SEQ ID NO: 53:

(i) SEQUENCE CHARACTERISTICS:
            (A) LENGTH: 68 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO: 53:

CTGGGCTGGC TTAAGCCATT GACATUUUUA UGUCAAUGGC UUAAGCCAGC CCAGGCGCGU       60

UUUCGCGC                                                                68

(2) INFORMATION FOR SEQ ID NO: 54:

(i) SEQUENCE CHARACTERISTICS:
            (A) LENGTH: 88 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO: 54:

GACAAGTTTC ACATGCCTAG GAGAAACTGA CTGCTUUUUA GCAGUCAGUU UCUCCTAGGC       60

AUGUGAAACU UGUCGCGCGU UUUCGCGC                                          88

(2) INFORMATION FOR SEQ ID NO: 55:

(i) SEQUENCE CHARACTERISTICS:
            (A) LENGTH: 76 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO: 55:

CCCTGAATGT CCTGGAAATG ACTGCCGATT TTTAUCTTCA GUCATTTCCA GGACAUUCAG    60

GGGCGCGTTT TCGCGC    76

(2) INFORMATION FOR SEQ ID NO: 56:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 56:

TAAGTTTCTT AACTGGGATT ATTAGCTGGG GTTTTCCCCA GCTAATAATC CCAGTTAAGA    60

AACUUAGCGC GTTTTCGCGC    80

(2) INFORMATION FOR SEQ ID NO: 57:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 57:

GTTTCTTAAC TGGGATTATT AGCTGTTTTC AGCUAATAAT CCCAGUUAAG AAACGCGCGT    60

TTTCGCGC    68

(2) INFORMATION FOR SEQ ID NO: 58:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 58:

TAAGTTTCTT AACTGGGATT ATTAGCTGGG GUUUUCCCCA GCUAAUAAUC CCAGUUAAGA    60

AACUUAGCGC GUUUUCGCGC    80

(2) INFORMATION FOR SEQ ID NO: 59:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 59:

TAAGTTTCTT AACTGGGATT ATTAGCTGGG GUUUUCCCCA GCUAAUAAUC UCAGUUAAGA    60

AACUUAGCGC GUUUUCGCGC    80

(2) INFORMATION FOR SEQ ID NO: 60:

(i) SEQUENCE CHARACTERISTICS:
    (A) LENGTH: 14 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 60:

Met Lys Val Leu Trp Ala Ala Leu Leu Val Thr Phe Leu Ala
1               5                   10

(2) INFORMATION FOR SEQ ID NO: 61:

(i) SEQUENCE CHARACTERISTICS:
        (A) LENGTH: 69 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 61:

Gly Cys Gln Ala Lys Val Glu Glu Ala Val Glu Thr Glu Pro Glu Pro
1               5                   10                  15

Glu Pro Glu Leu Arg Gln Gln Thr Glu Trp Gln Ser Gly Gln Arg Trp
                20                  25                  30

Glu Leu Ala Leu Gly Arg Phe Trp Asp Tyr Asp Tyr Leu Arg Trp Val
            35                  40                  45

Gln Thr Leu Ser Glu Gln Val Gln Glu Leu Leu Ser Ser Gln Val
        50                  55                  60

Thr Gln Glu Leu Arg
65

(2) INFORMATION FOR SEQ ID NO: 62:

(i) SEQUENCE CHARACTERISTICS:
        (A) LENGTH: 239 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 62:

ala leu met asp glu thr met lys glu leu lys ala tyr lys ser glu
1               5                   10                  15 leu glu glu gln leu thr Pro val ala glu glu thr arg ala arg leu
                20                  25                  30 ser lys glu leu gln ala ala gln ala arg leu gly ala asp met glu
            35                  40                  45 asp Val cys gly arg leu val gln tyr arg gly glu val gln ala met
        50                  55                  60 leu gly gln ser thr glu glu leu arg val arg leu ala ser his leu
65                  70                  75                  80 arg lys leu arg lys arg leu leu arg asp ala asp asp leu gln
                85                  90                  95 lys arg leu ala val tyr gln ala gln ala arg glu gly ala glu arg
            100                 105                 110 gly lys ser ala ile arg glu arg leu gly pro leu val glu gln gly
        115                 120                 125 arg val arg ala ala thr val gly ser leu ala gly gln pro leu gln

-continued

```
                 130              135              140
glu arg ala gln ala trp gly glu arg leu arg ala arg met glu Glu
145                 150                 155                 160 met gly ser arg thr arg asp arg leu asn glu val lys glu gln val
            165             170                 175 ala glu val arg ala lys leu glu gln ala Gln gln ile arg leu
            180             185                 190 gln ala glu ala phe gln ala arg leu lys ser trp phe ala ala glu
        195                 200                 205 pro leu val glu asp met gln arg gln trp ala gly leu val glu lys
        210             215                 220 val glu val gly thr ser ala ala pro val pro ser asp asn his
225                 230             235
```

What is claimed is:

1. A composition comprising:
 a) a recombinagenic oligonucleobase, which comprises a first and a second homologous region, which regions are homologous with a target gene of a mammal and a heterologous region, which is heterologous with the target gene and which contains an alteration disposed between the first and the second homologous region;
 b) an aqueous carrier; and
 c) a macromolecular carrier, which comprises a ligand for a clathrin-coated pit receptor, wherein the macromolecular carrier is selected from the group consisting of:
  (i) an aqueous-cored lipid vesicle, wherein the aqueous core contains the oligonucleobase,
  (ii) a lipid nanosphere, which comprises a lipophilic salt of the oligonucleobase, and
  (iii) a polycation having an average molecular weight of between 500 daltons and 1.3 Md wherein the polycation forms a salt with the oligonucleobase.

2. The composition of claim 1, in which the aqueous-cored lipid vesicle is a negatively charged, aqueous-cored lipid vesicle.

3. The composition of claim 1, in which the polycation is a branched chain polyethylenimine.

4. The composition of claim 1, in which the polycation is a linear polyethylenimine.

5. The composition of claim 1, in which the aqueous-cored lipid vesicle comprises a fusigenic F-protein.

6. The composition of claim 1, in which:
 a) the first and the second homologous region are together at least 16 and not more than 60 nucleobases in length; and
 b) the heterologous region is at least 1 and not more than 20 nucleobases in length.

7. The composition of claim 1, in which the ligand for the clathrin-coated pit receptor is a ligand for a receptor selected from the group consisting of the transferrin receptor, nicotinic acid receptor, carnitine receptor, insulin receptor and insulin like growth factor-1 receptor.

8. A method of treating a disease caused by a mutated nucleotide sequence in a target gene in a cell in a mammalian subject comprising administering to the mammalian subject a composition comprising:
 a) a recombinagenic oligonucleobase, which comprises a first and a second homologous region, which regions are homologous with a target gene of a mammal, and a heterologous region, which is heterologous with the target gene and which contains an alteration, disposed between the first and the second homologous region;
 b) an aqueous carrier; and
 c) a macromolecular carrier selected from the group consisting of:
  (i) an aqueous-cored lipid vesicle, wherein the aqueous core contains the oligonucleobase,
  (ii) a lipid nanosphere, which comprises a lipophilic salt of the oligonucleobase, and
  (iii) a polycation having an average molecular weight of between 500 daltons and 1.3 Md wherein the polycation forms a salt with the oligonucleobase,
wherein the macromolecular carrier further comprises a ligand for a clathrin-coated pit receptor, in an amount effective to alter the nucleotide sequence of the target gene in a number of cells in the subject to ameliorate the disease caused by the mutated sequence.

9. The composition of claim 2, in which the aqueous-cored lipid vesicle comprises dioleoylphosphatidylcholine and dioleoylphosphatidylserine.

10. The composition of claim 9, in which the aqueous-cored lipid vesicle further comprises a cerebroside.

11. The composition of claim 6, in which the recombinagenic oligonucleobase comprises at least 15 deoxynucleotides that are Watson-Crick base paired with 2'-Substituted Ribonucleotides.

12. The composition of claim 11, in which the 2'-Substituted Ribonucleotides are independently selected from the group consisting of 2'-methoxy-ribonucleotides, 2'-allyloxy-ribonucleotides, 2'-methoxyethoxy-ribonucleotides and 2'-fluoro-ribonucleotides.

13. The composition of claim 7, in which the clathrin-coated pit receptor is the asialoglycoprotein receptor.

14. The composition of claim 13, in which the ligand for the asialogylcoprotein receptor comprises a moiety selected from the group consisting of lactose, galactose, and N-acetylgalactosamine, and in which the sequence of the oligonucleobase comprises the sequence of a contiguous 16 nucleotide fragment of a mammalian gene that encodes a product selected from the group consisting of α1-antitrypsin, coagulation factor IX, uridinediphosphoglucuronate glucuronosyltransferase, glucocerebrosidase, glucose-6-phosphatase, low density lipoprotein receptor, ornithine transcarbamylase and phenylalanine hydroxylase, or the complement of the fragment.

15. A method of altering the nucleotide sequence of a target gene in a cell of a subject mammal comprising administering to the subject mammal the composition of claim 1 in an amount sufficient to alter the nucleotide sequence of the target gene in the cell of the subject mammal.

16. The method of claim 15, in which the cell is a liver cell.

17. The method of claim 15, in which:
   a) the first and the second homologous region are together at least 16 and not more than 60 nucleobases in length; and
   b) the heterologous region is at least 1 and not more than 20 nucleobases in length.

18. The composition of claim 1, in which the clathrin-coated pit receptor is the asialoglycoprotein receptor.

19. The method of claim 8, which further comprises the steps of determining the phenotypic effect of the altered target genes in the subject and subsequently increasing or decreasing said phenotypic effect by adjusting the number of said altered target genes in the subject.

20. The method of claim 8, which the cell is a hepatocyte.

21. The method of claim 18, in which:
   a) the first and the second homologous region are together at least 16 and not more than 60 nucleobases in length; and
   b) the heterologous region is at least 1 and not more than 20 nucleobases in length.

22. The method of claim 8, in which the target gene is an allele of a mammalian gene that encodes a product selected from the group consisting of α1-antitrypsin, coagulation factor IX, uridinediphosphoglucuronate glucuronosyltransferase, glucocerebrosidase, glucose-6-phosphatase, low density lipoprotein receptor, ornithine transcarbamylase and phenylalanine hydroxylase.

23. The method of claim 8 wherein the mammalian subject is a human.

24. A method of reducing LDL in the blood of a mammalian subject comprising administering to the mammalian subject a composition comprising:
   a) a recombinagenic oligonucleobase, which comprises a first and a second homologous region, which homologous regions each have a nucleotide sequence of at least 10 contiguous nucleobases from nucleotides 4342–11913 of the ApoB gene (SEO ID NO:2), and a heterologous region, which is heterologous with the ApoB gene and which contains an alteration, disposed between the first and the second homologous region;
   b) an aqueous carrier; and
   c) a macromolecular carrier selected from the group consisting of:
      (i) an aqueous-cored lipid vesicle, wherein the aqueous core contains the oligonucleobase,
      (ii) a lipid nanosphere, which comprises a lipophilic salt of the oligonucleobase, and
      (iii) a polycation having an average molecular weight of between 500 daltons and 1.3 Md wherein the polycation forms a salt with the oligonucleobase,
   wherein the macromolecular carrier further comprises a ligand for a clathrin-coated pit receptor, in an amount effective to alter the nucleotide sequence of the ApoB gene in a number of cells in the subject to reduce LDL levels in the blood of the subject.

25. The method of claim 24, which further comprises the steps of determining the effect of the alteration of the ApoB genes on the level of LDL in the blood of the subject and subsequently adjusting the number of altered ApoB genes in the subject.

26. The method of claim 24, in which the altered gene encodes a protein consisting of at least 1841 amino acids and not more than 2975 amino acids.

27. The method of claim 24 wherein the mammalian subject is a human.

28. The method of claim 26, in which the altered gene encodes a protein consisting of a fragment of SEQ ID NO:1 which fragment consists of at least amino acids 1–1841 and not more than amino acids 1–2975 of SEQ ID NO:1.

29. A composition for the modification of a human ApoB gene comprising:
   a) a recombinagenic oligonucleobase, which comprises a first and a second homologous region, which homologous regions each have a nucleotide sequence of at least 8 nucleobases and together are at least 20 nucleobases in length and which homologous regions are each homologous with a fragment consisting of nucleotides 5649–9051 of the ApoB gene (SEQ ID NO:2), and a heterologous region, which is heterologous with the ApoB gene and which contains an alteration, disposed between the first and the second homologous region:
   b) an aqueous carrier; and
   c) a macromolecular carrier selected from the group consisting of:
      (i) an aqueous-cored lipid vesicle, wherein the aqueous core contains the oligonucleobase,
      (ii) a lipid nanosphere, which comprises a lipophilic salt of the oligonucleobase, and
      (iii) a polycation having an average molecular weight of between 500 daltons and 1.3 Md wherein the polycation forms a salt with the oligonucleobase,
   wherein the macromolecular carrier further comprises a ligand for a clathrin-coated pit receptor.

30. The composition of claim 29 in which the first and the second homologous regions each comprise at least 3 contiguous nucleobase-pairs of hybrid-duplex.

31. The composition of claim 29, in which the sum of the lengths of the first and second homologous regions is not more than 60 nucleobases in length.

32. The composition of claim 29, in which the homologous regions together comprise between 9 and 25 nucleobase pairs of hybrid-duplex.

33. The composition of claim 29, in which the GC fraction of each homologous region is at least 33%.

34. The composition of claim 29, in which the GC fraction of each homologous region is at least 50%.

35. The composition of claim 29, in which the sequence of the oligonucleobase comprises the sequence of at least a 21 nucleobase fragment of any one of the sequences depicted in SEQ ID NOS:4–20, or the complement thereof.

36. The composition of claim 29, in which the sequence of the oligonucleobase comprises the sequence of at least a 25 nucleobase fragment of any one of the sequences depicted in SEQ ID NOS:4–20, or the complement thereof.

* * * * *